(12) United States Patent
Gasper et al.

(10) Patent No.: US 8,881,945 B2
(45) Date of Patent: Nov. 11, 2014

(54) SPRAY DISPENSER

(71) Applicant: S.C. Johnson & Son, Inc., Racine, WI (US)

(72) Inventors: Thomas P. Gasper, Germantown, WI (US); Christopher S. Hoppe, Milwaukee, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 22 days.

(21) Appl. No.: 13/623,001

(22) Filed: Sep. 19, 2012

(65) Prior Publication Data

US 2013/0068783 A1  Mar. 21, 2013

Related U.S. Application Data

(60) Provisional application No. 61/536,453, filed on Sep. 19, 2011.

(51) Int. Cl.
| | |
|---|---|
| *B67B 7/00* | (2006.01) |
| *A61L 9/14* | (2006.01) |
| *A01M 1/20* | (2006.01) |
| *B65D 83/26* | (2006.01) |
| *A61L 9/12* | (2006.01) |
| *B65D 83/38* | (2006.01) |
| *B65D 83/68* | (2006.01) |

(52) U.S. Cl.
CPC ............... *A61L 9/14* (2013.01); *A01M 1/2038* (2013.01); *B65D 83/262* (2013.01); *A61L 9/125* (2013.01); *A61L 2209/111* (2013.01); *B65D 83/386* (2013.01); *B65D 83/68* (2013.01)
USPC .................. 222/1; 222/63; 222/639

(58) Field of Classification Search
CPC ...... B65D 83/26; B65D 83/262; B65D 83/68; B65D 83/386; B05B 9/0861; B05B 9/0866; B05B 12/04; A47K 5/1217; A61L 2209/111; A61L 9/125; A61L 9/14; A01M 1/2038
USPC ............ 222/52, 63, 333, 129, 131–148, 641, 222/642, 645–652; 239/332, 333
See application file for complete search history.

(56) References Cited

U.S. PATENT DOCUMENTS

| | | |
|---|---|---|
| 2,991,912 A | 7/1961 | Thomas et al. |
| 3,214,062 A | 10/1965 | Mahon |

(Continued)

FOREIGN PATENT DOCUMENTS

| | | |
|---|---|---|
| DE | 202009008674 U1 | 10/2009 |
| DE | 202010005686 A1 | 1/2011 |

(Continued)

OTHER PUBLICATIONS

PCT/US2012/056052 International Search Report dated Mar. 20, 2013.

*Primary Examiner* — Lien Ngo

(57) ABSTRACT

A method of operating a dispensing system includes the step of alternating between active and lockout modes within a first timing sequence, wherein during the active mode at least one sensor is active to detect sensory input, and whereupon detection of the sensory input results in product being released from a first container, and wherein during a lockout mode product is not released from the first container. The method further includes the step of alternating between active and lockout modes within a second timing sequence, wherein during the active period at least one sensor is active to detect sensory input, and whereupon detection of the sensory input results in fluid being released from a second container, and wherein during a lockout mode fluid is not released from the second container. The expiration of the first timing sequence, and the initiation of the second timing sequence, occurs from at least one of the lapsing of a time interval, sensory input, and manual input from a user.

20 Claims, 60 Drawing Sheets

(56) References Cited

U.S. PATENT DOCUMENTS

| | | |
|---|---|---|
| 3,369,697 A | 2/1968 | Glucksman et al. |
| 3,398,863 A | 8/1968 | Kolodziej |
| 3,610,471 A | 10/1971 | Werner |
| 3,677,441 A | 7/1972 | Nixon, Jr. et al. |
| 3,779,425 A | 12/1973 | Werner |
| 3,856,443 A | 12/1974 | Salvi |
| 3,952,916 A | 4/1976 | Phillips |
| 3,980,205 A | 9/1976 | Smart |
| 4,004,715 A | 1/1977 | Williams et al. |
| 4,063,664 A | 12/1977 | Meetze, Jr. |
| 4,184,612 A | 1/1980 | Freyre |
| 4,238,055 A | 12/1980 | Staar |
| 4,836,420 A | 6/1989 | Kromrey |
| 4,916,762 A | 4/1990 | Shaw |
| 5,022,557 A | 6/1991 | Turner |
| 5,349,945 A | 9/1994 | Wass et al. |
| RE34,847 E | 2/1995 | Muderlak et al. |
| 5,695,091 A | 12/1997 | Winings et al. |
| 5,699,243 A | 12/1997 | Eckel et al. |
| 5,946,209 A | 8/1999 | Eckel et al. |
| 6,026,987 A | 2/2000 | Burnett et al. |
| 6,036,108 A | 3/2000 | Chen |
| 6,039,212 A | 3/2000 | Singh |
| 6,142,339 A | 11/2000 | Blacker et al. |
| 6,151,529 A | 11/2000 | Batko |
| 6,161,724 A | 12/2000 | Blacker et al. |
| 6,196,218 B1 | 3/2001 | Voges |
| 6,216,925 B1 | 4/2001 | Garon |
| 6,254,065 B1 * | 7/2001 | Ehrensperger et al. .......... 261/26 |
| 6,267,297 B1 | 7/2001 | Contadini et al. |
| 6,394,310 B1 | 5/2002 | Muderlak et al. |
| 6,461,325 B1 | 10/2002 | Delmotte et al. |
| 6,499,900 B1 | 12/2002 | Brozell |
| 6,517,009 B2 | 2/2003 | Yahav |
| 6,529,446 B1 | 3/2003 | de la Huerga |
| 6,540,155 B1 | 4/2003 | Yahav |
| 6,554,203 B2 | 4/2003 | Hess et al. |
| 6,610,254 B1 | 8/2003 | Furner et al. |
| 6,619,562 B2 | 9/2003 | Hamaguchi et al. |
| 6,644,507 B2 | 11/2003 | Borut et al. |
| 6,672,129 B1 | 1/2004 | Frederickson et al. |
| 6,712,287 B1 | 3/2004 | Le Pesant et al. |
| 6,739,479 B2 | 5/2004 | Contadini et al. |
| 6,769,580 B2 | 8/2004 | Muderlak et al. |
| 6,790,408 B2 | 9/2004 | Whitby et al. |
| 6,834,847 B2 | 12/2004 | Bartsch et al. |
| 6,877,636 B2 | 4/2005 | Speckhart et al. |
| 6,889,872 B2 | 5/2005 | Herman et al. |
| 6,903,654 B2 | 6/2005 | Hansen et al. |
| 6,929,154 B2 | 8/2005 | Grey et al. |
| 6,948,192 B2 | 9/2005 | Hipponsteel |
| 6,968,982 B1 | 11/2005 | Burns |
| 6,981,499 B2 | 1/2006 | Anderson et al. |
| 7,021,499 B2 | 4/2006 | Hansen et al. |
| 7,160,515 B2 | 1/2007 | Murdell et al. |
| 7,188,485 B2 | 3/2007 | Szpekman |
| 7,207,500 B2 | 4/2007 | Hudson et al. |
| 7,222,760 B1 | 5/2007 | Tsay |
| 7,265,673 B2 | 9/2007 | Teller |
| 7,306,167 B2 | 12/2007 | Colarusso et al. |
| 7,308,790 B1 | 12/2007 | Bennett et al. |
| 7,320,418 B2 | 1/2008 | Sassoon |
| 7,344,123 B2 | 3/2008 | Pankhurst et al. |
| 7,398,013 B2 | 7/2008 | He et al. |
| 7,407,065 B2 | 8/2008 | Hooks et al. |
| 7,437,930 B2 | 10/2008 | Lasserre et al. |
| 7,461,650 B1 | 12/2008 | Rand |
| 7,469,844 B2 * | 12/2008 | Conway et al. ............ 239/102.2 |
| 7,481,380 B2 | 1/2009 | Kvietok et al. |
| 7,497,354 B2 | 3/2009 | Decottignies et al. |
| 7,509,955 B2 | 3/2009 | Cole et al. |
| 7,538,473 B2 | 5/2009 | Blandino et al. |
| 7,556,210 B2 | 7/2009 | Mandell et al. |
| 7,597,099 B2 | 10/2009 | Jones et al. |
| 7,611,253 B2 | 11/2009 | Chien |
| 7,628,339 B2 | 12/2009 | Ivri et al. |
| 7,654,416 B2 | 2/2010 | Buining et al. |
| 7,670,479 B2 | 3/2010 | Arett et al. |
| 7,673,820 B2 | 3/2010 | Ivri et al. |
| 7,686,191 B1 | 3/2010 | Burns |
| 7,687,744 B2 | 3/2010 | Walter et al. |
| 7,690,530 B2 | 4/2010 | Schneider et al. |
| 7,735,694 B2 | 6/2010 | Brown et al. |
| 7,739,479 B2 | 6/2010 | Bordes et al. |
| 7,740,395 B2 | 6/2010 | Samuel et al. |
| 7,762,714 B2 | 7/2010 | Freeman et al. |
| 7,766,194 B2 | 8/2010 | Boll et al. |
| 7,798,420 B2 | 9/2010 | Lind et al. |
| 7,798,424 B2 | 9/2010 | Lin |
| 7,837,065 B2 | 11/2010 | Furner et al. |
| 7,871,020 B2 | 1/2011 | Nelson et al. |
| 7,893,829 B2 | 2/2011 | Sipinski et al. |
| 7,909,209 B2 | 3/2011 | Reynolds et al. |
| 7,930,068 B2 | 4/2011 | Robert et al. |
| 7,954,667 B2 | 6/2011 | Furner et al. |
| 7,979,723 B2 | 7/2011 | Dooley et al. |
| 7,995,295 B2 | 8/2011 | Chen |
| 8,051,282 B2 | 11/2011 | Sipinski et al. |
| 8,052,934 B2 | 11/2011 | Manne |
| 8,061,562 B2 | 11/2011 | Carpenter et al. |
| 8,074,836 B2 | 12/2011 | Reynolds et al. |
| 8,074,970 B2 | 12/2011 | Pankhurst et al. |
| 8,091,734 B2 | 1/2012 | Furner et al. |
| 8,170,405 B2 | 5/2012 | Harris |
| 8,224,481 B2 | 7/2012 | Bylsma et al. |
| 8,302,812 B2 | 11/2012 | Reynolds |
| 8,342,363 B2 | 1/2013 | Carpenter et al. |
| 8,357,114 B2 | 1/2013 | Poutiatine et al. |
| 8,360,273 B2 | 1/2013 | Reinsel et al. |
| 2005/0234402 A1 | 10/2005 | Collins et al. |
| 2006/0086824 A1 | 4/2006 | Pearce et al. |
| 2007/0235555 A1 | 10/2007 | Helf et al. |
| 2007/0289993 A1 * | 12/2007 | Nanda ............................. 222/39 |
| 2008/0210772 A1 | 9/2008 | Pearce et al. |
| 2008/0272148 A1 | 11/2008 | Malik et al. |
| 2008/0277411 A1 | 11/2008 | Beland et al. |
| 2008/0290113 A1 | 11/2008 | Helf et al. |
| 2009/0020560 A1 | 1/2009 | Kraus |
| 2009/0045218 A1 | 2/2009 | Helf et al. |
| 2009/0045219 A1 | 2/2009 | Helf et al. |
| 2009/0045220 A1 | 2/2009 | Helf et al. |
| 2009/0117012 A1 | 5/2009 | Bankers et al. |
| 2009/0185951 A1 | 7/2009 | Litten-Brown et al. |
| 2009/0218413 A1 | 9/2009 | Withers |
| 2009/0294471 A1 | 12/2009 | Paige |
| 2009/0302056 A1 | 12/2009 | Butler |
| 2009/0314849 A1 | 12/2009 | Litten-Brown et al. |
| 2010/0025427 A1 | 2/2010 | Chiou et al. |
| 2010/0031982 A1 * | 2/2010 | Hornsby et al. .......... 134/169 R |
| 2010/0037512 A1 | 2/2010 | Durand |
| 2010/0038379 A1 | 2/2010 | Butler et al. |
| 2010/0044468 A1 | 2/2010 | Granger et al. |
| 2010/0059602 A1 | 3/2010 | Chiou et al. |
| 2010/0071121 A1 * | 3/2010 | Kissner et al. .................... 4/223 |
| 2010/0221143 A1 | 9/2010 | Broncano Atencia et al. |
| 2010/0226818 A1 | 9/2010 | Miyagi et al. |
| 2010/0237108 A1 | 9/2010 | Anderson et al. |
| 2010/0252574 A1 | 10/2010 | Busin |
| 2010/0266266 A1 | 10/2010 | Garcia Fabrega et al. |
| 2010/0272599 A1 | 10/2010 | Broncano Atencia et al. |
| 2010/0320239 A1 | 12/2010 | Sordo et al. |
| 2011/0030681 A1 | 2/2011 | De Vries et al. |
| 2011/0073675 A1 | 3/2011 | Wolosuk |
| 2011/0076185 A1 | 3/2011 | Hammond et al. |
| 2011/0089260 A1 | 4/2011 | Van Roemburg |
| 2011/0095044 A1 | 4/2011 | Sipinski |
| 2011/0125318 A1 | 5/2011 | Dunn |
| 2011/0200488 A1 | 8/2011 | Cennini et al. |

(56) References Cited

U.S. PATENT DOCUMENTS

| | | |
|---|---|---|
| 2011/0278322 A1 | 11/2011 | Reynolds et al. |
| 2012/0091209 A1 | 4/2012 | Hotaling et al. |

FOREIGN PATENT DOCUMENTS

| | | |
|---|---|---|
| DE | 102010020508 A1 | 2/2011 |
| DE | 202010014615 U1 | 2/2011 |
| EP | 0719234 B1 | 7/1996 |
| EP | 1194351 A1 | 4/2002 |
| EP | 1240480 A1 | 9/2002 |
| EP | 1370304 A1 | 12/2003 |
| EP | 1547505 A1 | 6/2005 |
| EP | 1645294 A2 | 4/2006 |
| EP | 1675657 A1 | 7/2006 |
| EP | 1695720 A1 | 8/2006 |
| EP | 1771358 A1 | 4/2007 |
| EP | 1824760 A1 | 8/2007 |
| EP | 1844795 A1 | 10/2007 |
| EP | 1848649 A1 | 10/2007 |
| EP | 1848650 A1 | 10/2007 |
| EP | 1874657 A1 | 1/2008 |
| EP | 1976775 A1 | 10/2008 |
| EP | 2041000 A1 | 4/2009 |
| EP | 2143575 A1 | 1/2010 |
| EP | 2187977 A2 | 5/2010 |
| EP | 2190489 A2 | 6/2010 |
| EP | 2200751 A1 | 6/2010 |
| EP | 2204092 A1 | 7/2010 |
| EP | 2207734 A1 | 7/2010 |
| FR | 2036157 | 12/1970 |
| WO | 03098971 A1 | 11/2003 |
| WO | 2004093927 A1 | 11/2004 |
| WO | 2004093929 A2 | 11/2004 |
| WO | WO2007146332 A2 | 12/2007 |
| WO | 2008149065 A1 | 12/2008 |
| WO | WO 2008/149064 | * 12/2008 ...... 222/39 |
| WO | WO 2008/149066 | * 12/2008 ...... 222/39 |
| WO | WO2009103738 A1 | 8/2009 |
| WO | WO2009130927 A1 | 10/2009 |
| WO | WO2009151213 A1 | 12/2009 |
| WO | WO2010030629 A1 | 3/2010 |
| WO | WO2010039621 A1 | 4/2010 |
| WO | WO2010101455 A2 | 9/2010 |
| WO | WO2010130891 A1 | 11/2010 |
| WO | WO2010145038 A1 | 12/2010 |
| WO | 2011045620 A1 | 4/2011 |

\* cited by examiner

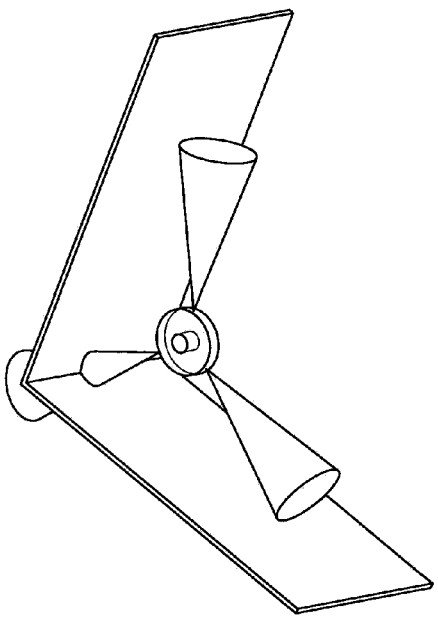
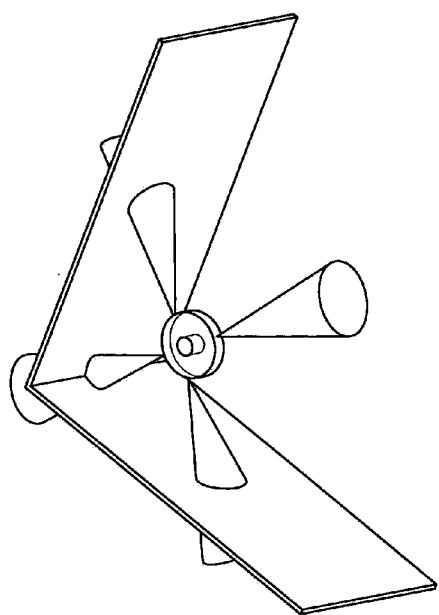
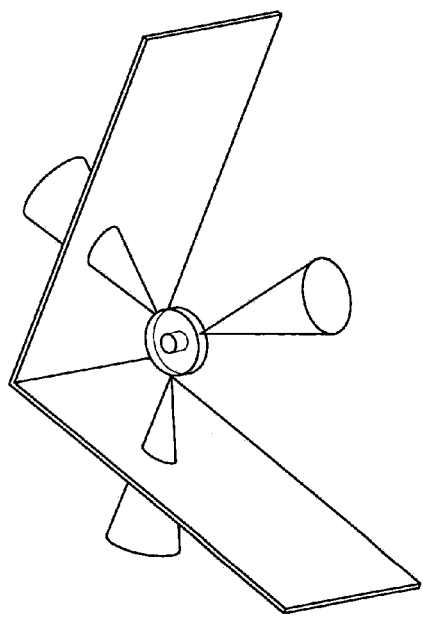
FIG. 29A
FIG. 29B
FIG. 29C

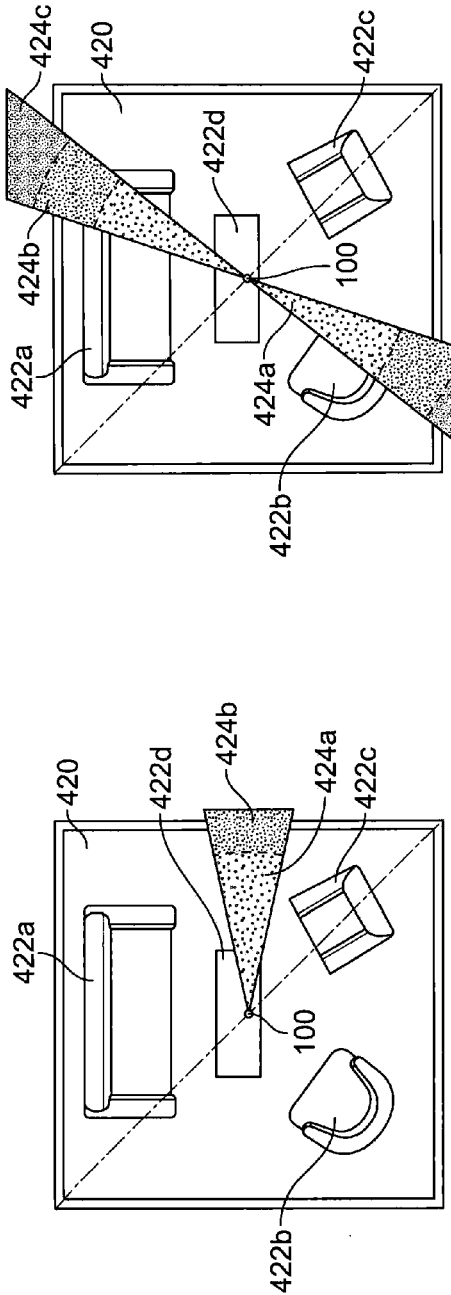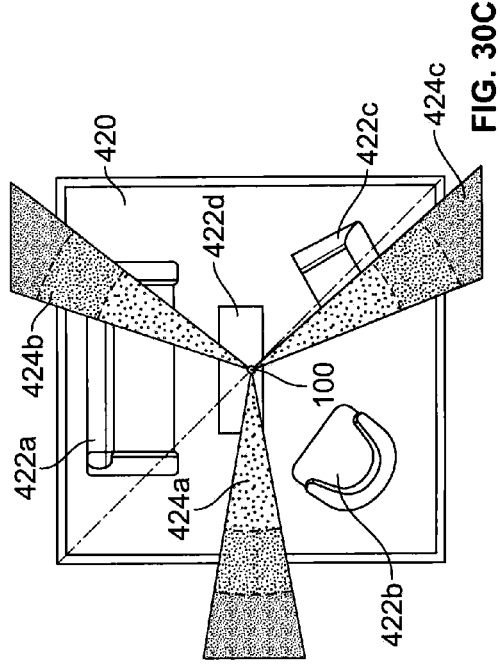
FIG. 30A
FIG. 30B
FIG. 30C

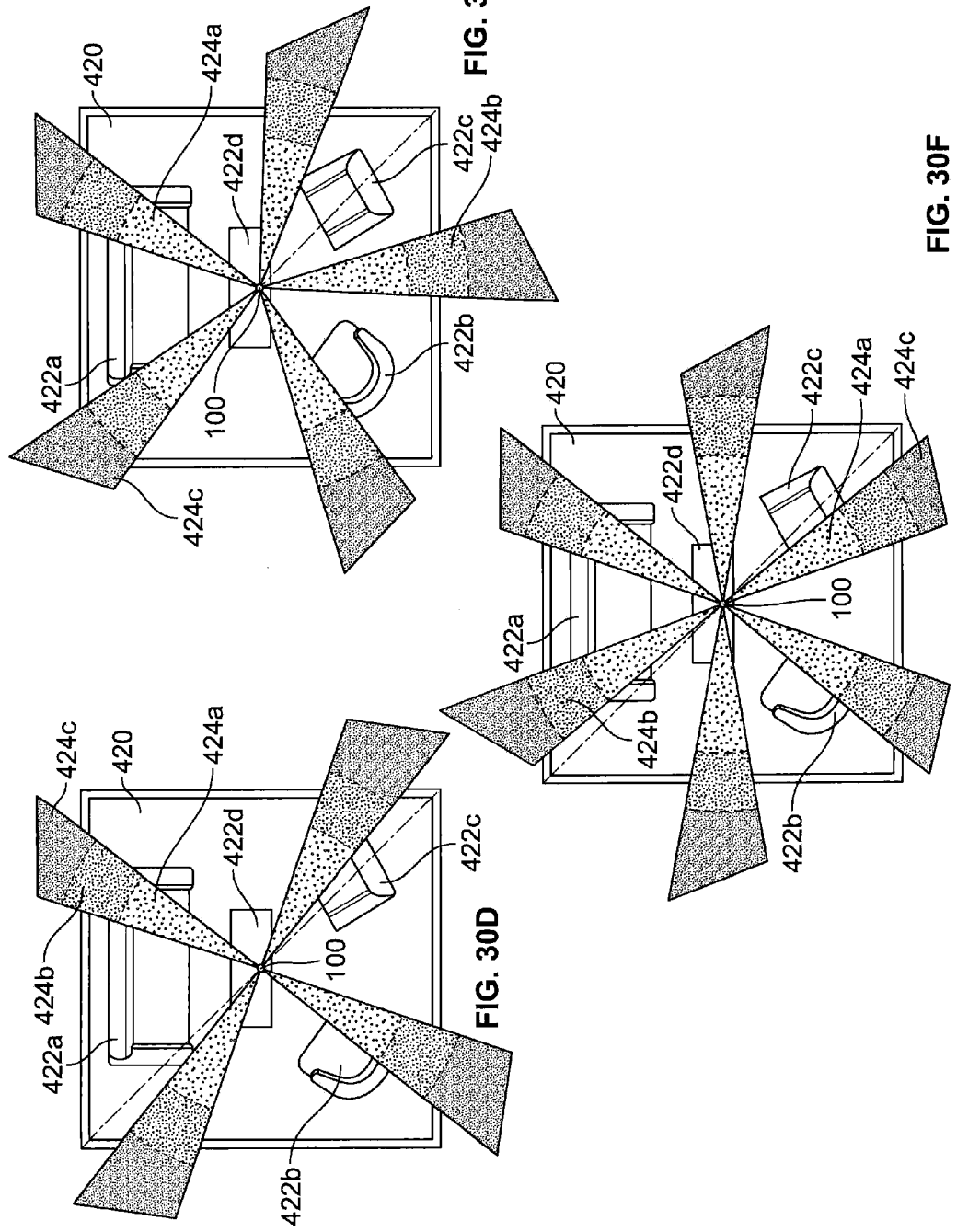

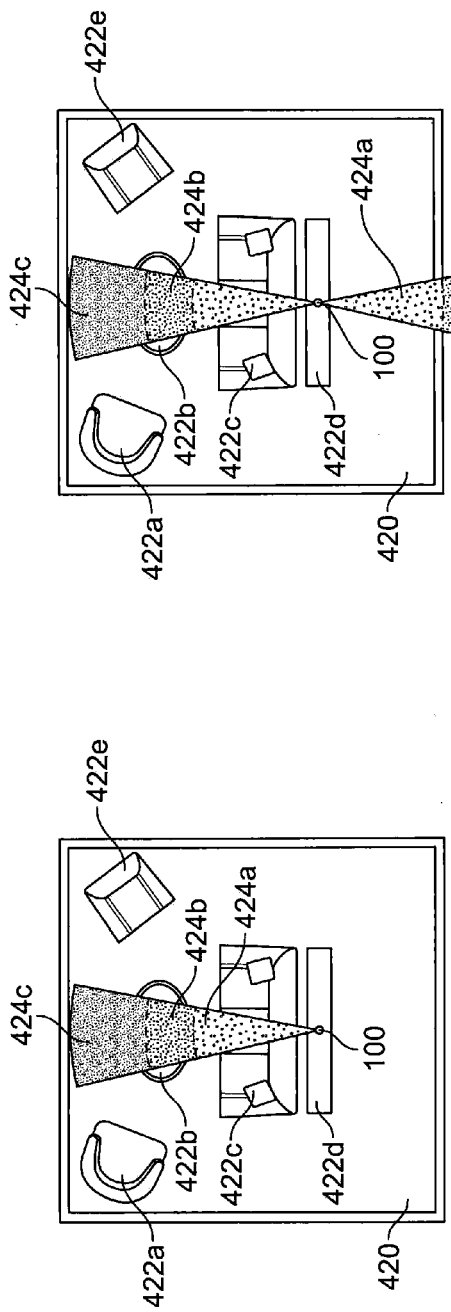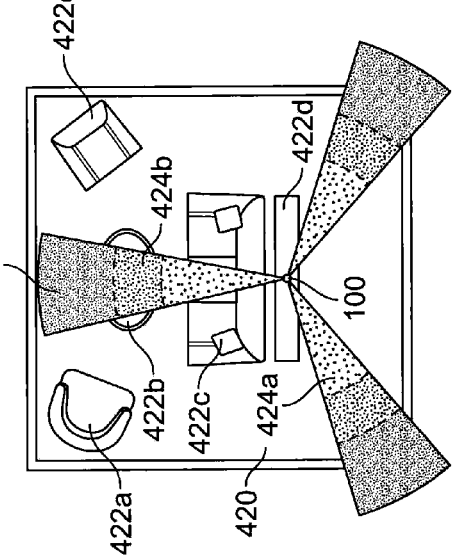

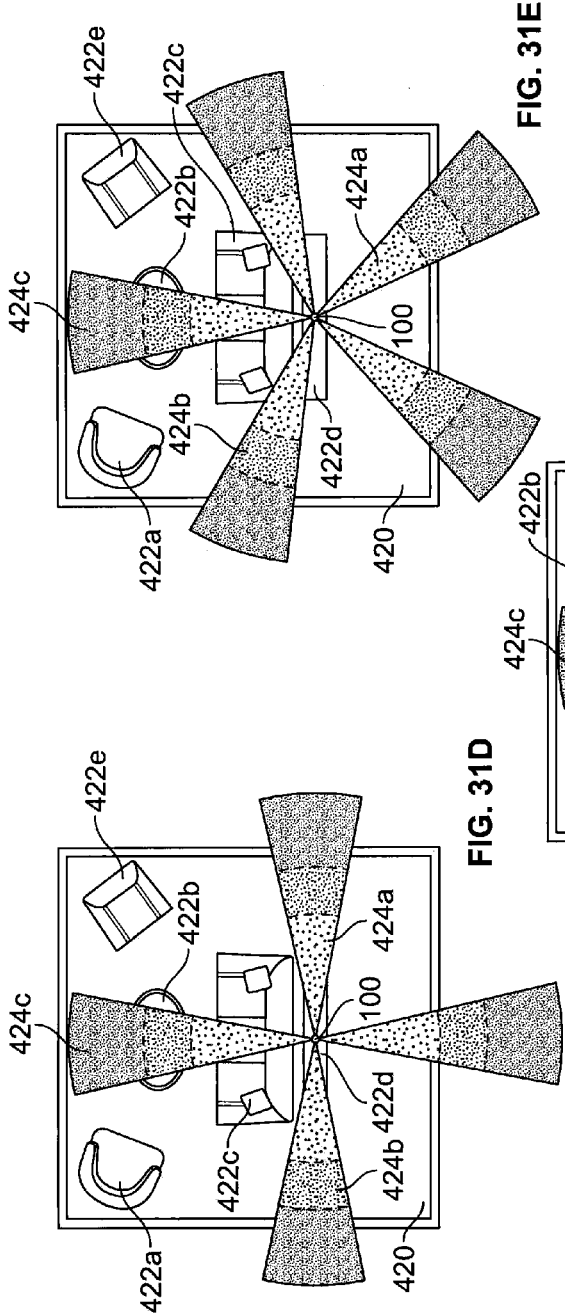
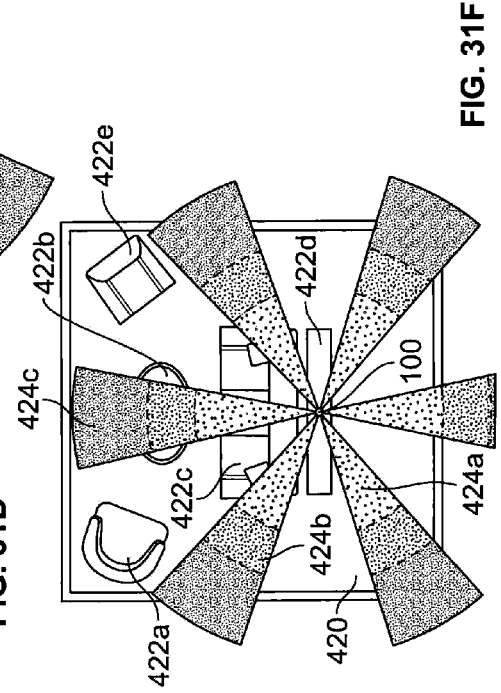

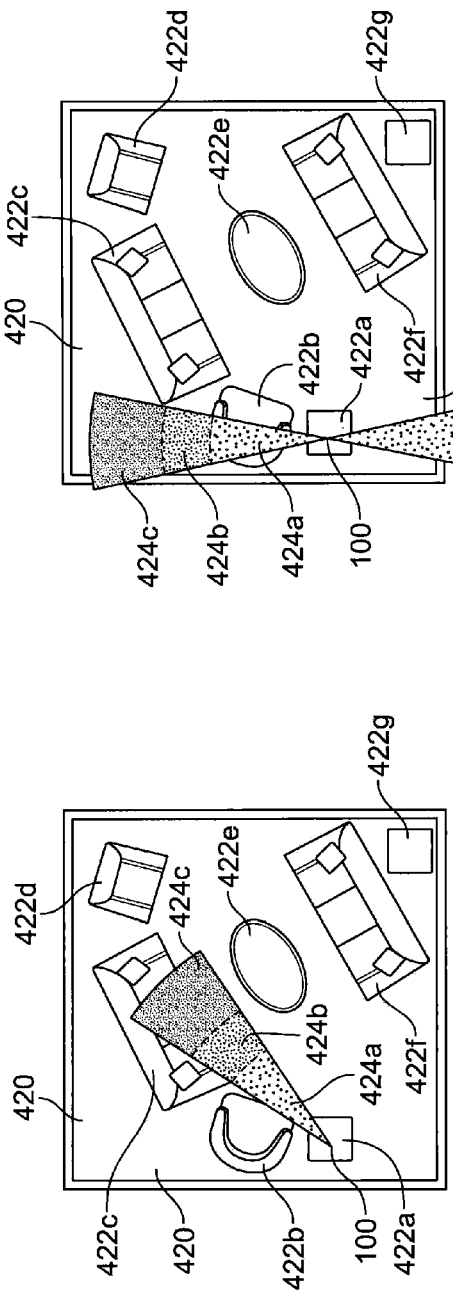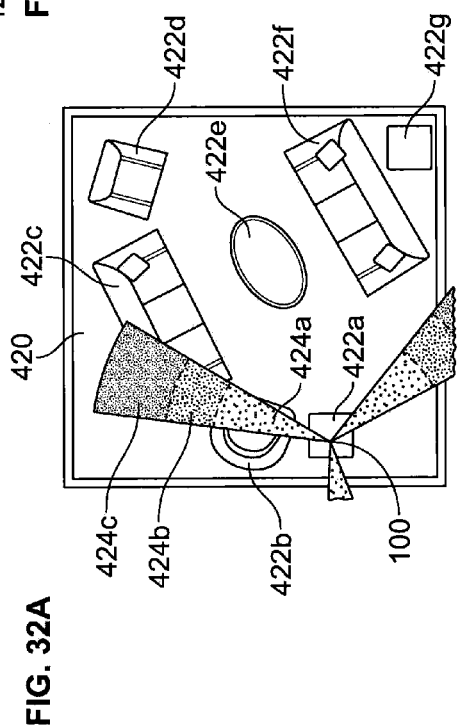
FIG. 32A
FIG. 32B
FIG. 32C

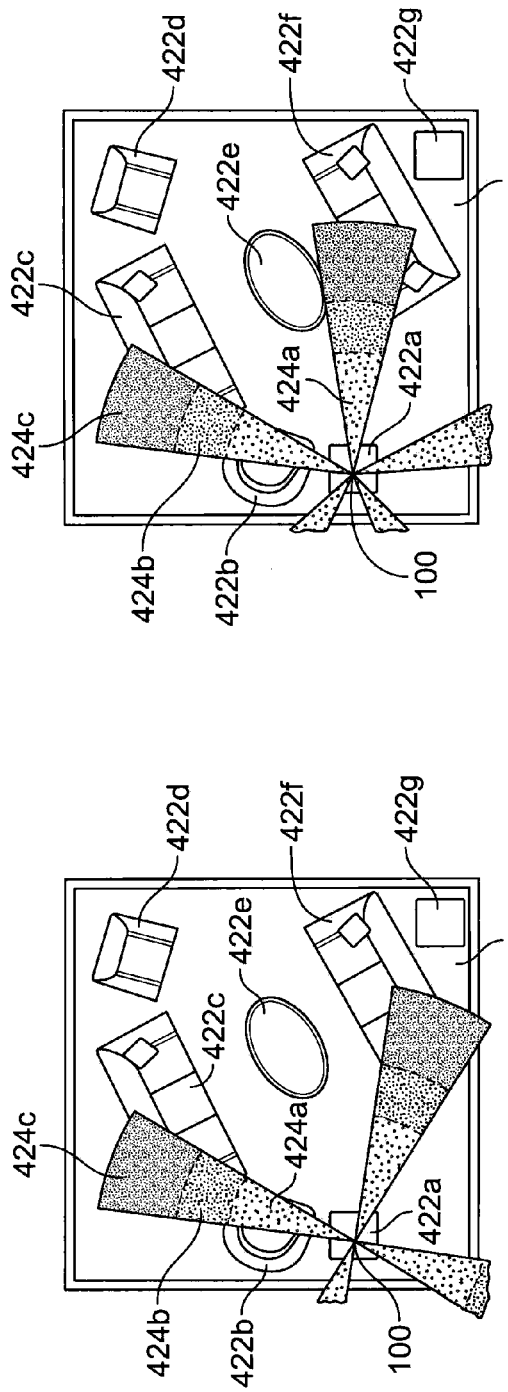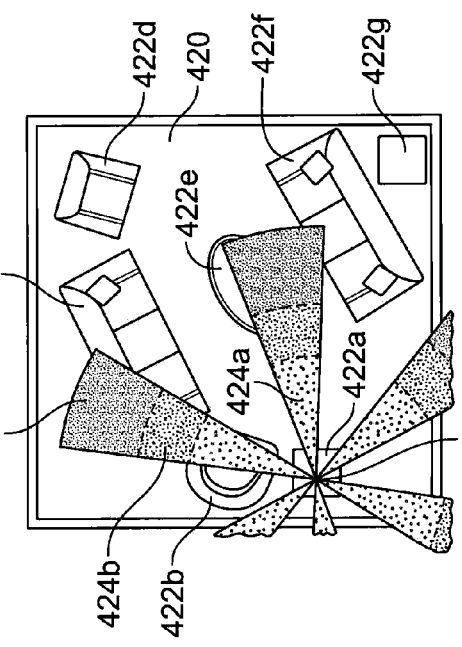
FIG. 32D
FIG. 32E
FIG. 32F

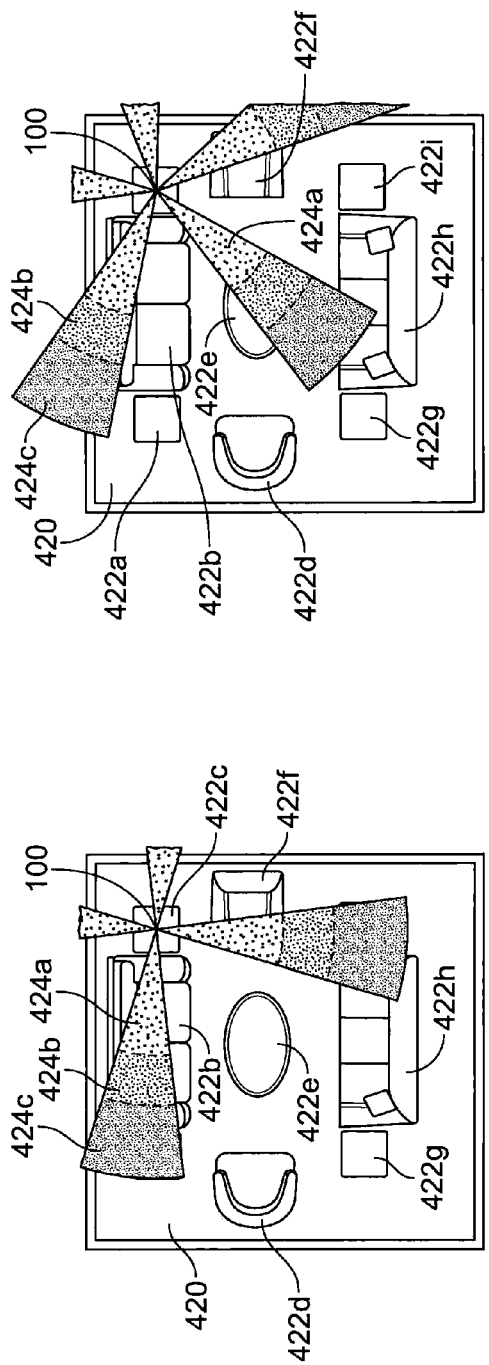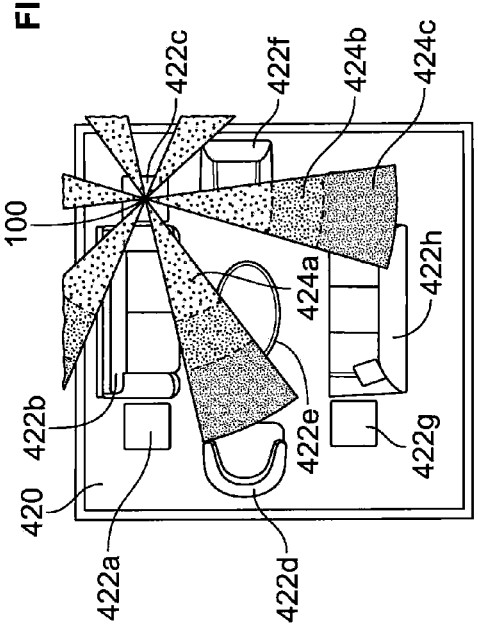

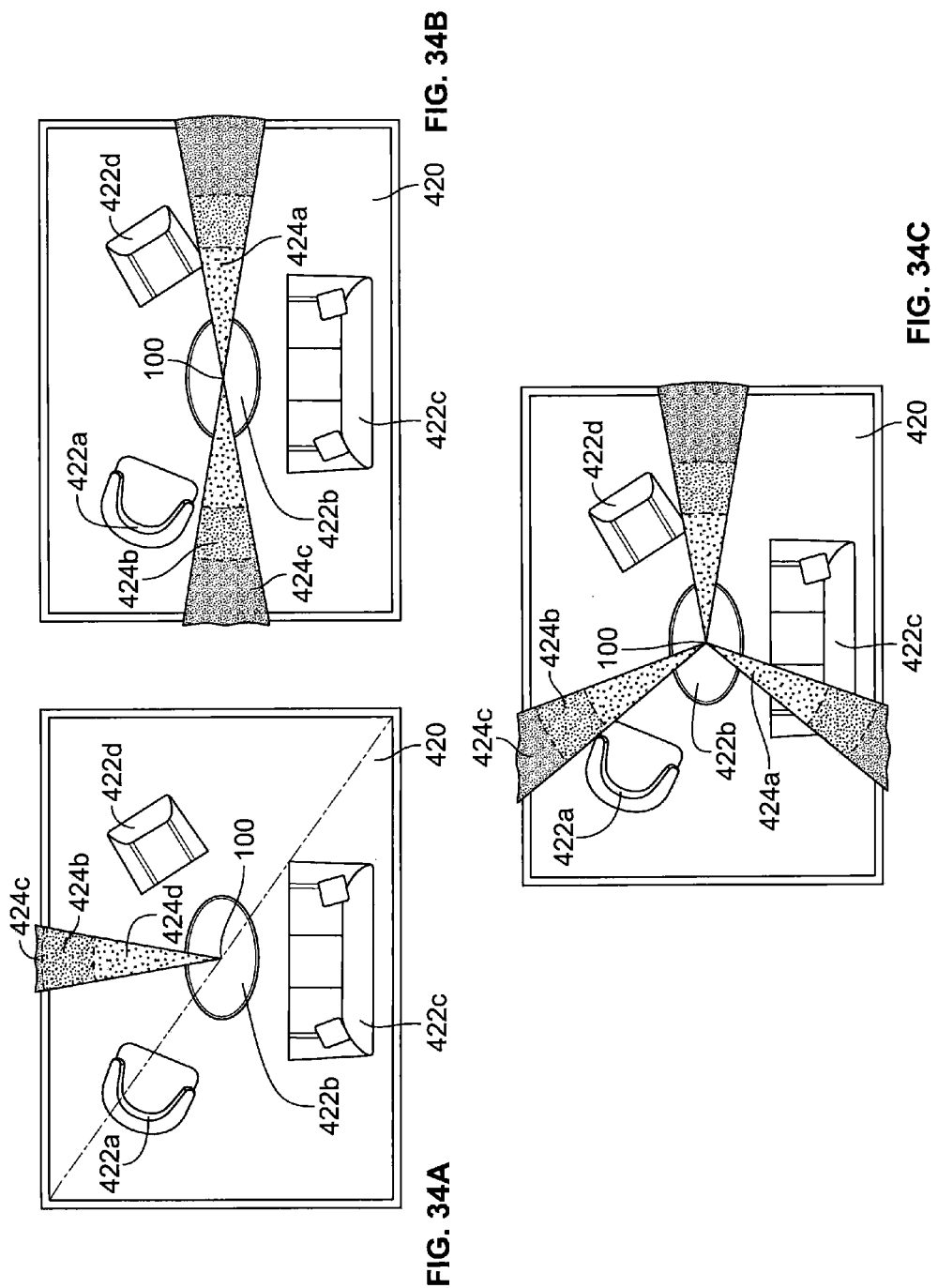

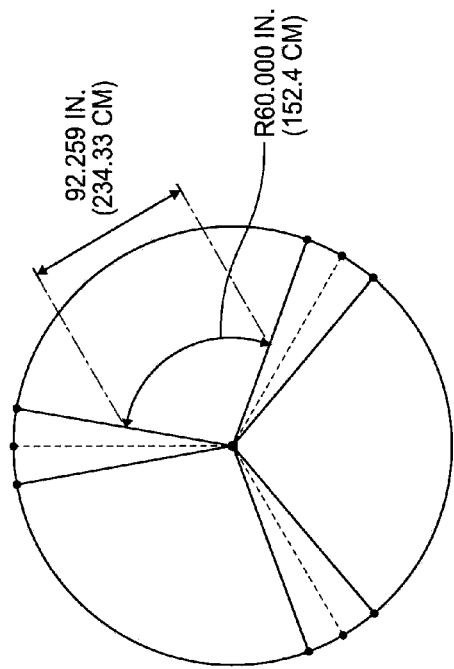
FIG. 35A
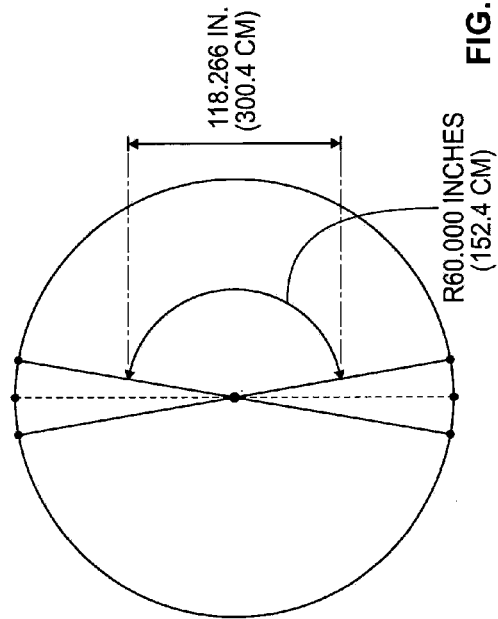
FIG. 35B
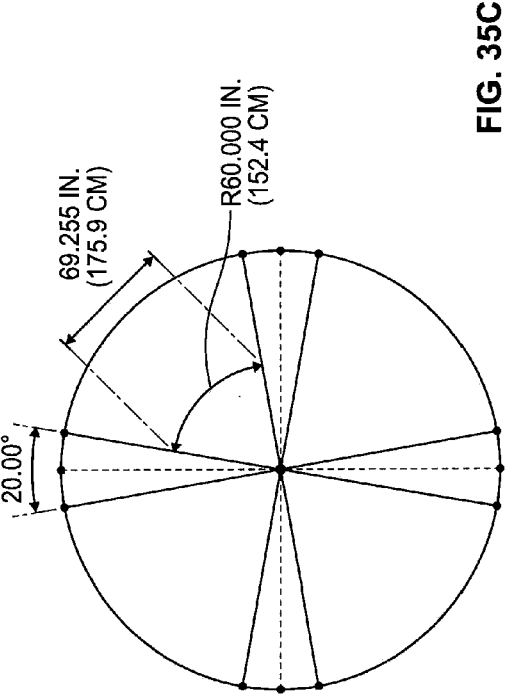
FIG. 35C
FIG. 35D

|  | GAP (CM) | GAP REDUCTION (CM) |
|---|---|---|
| 2 SENSORS | 300.36CM |  |
| 3 SENSORS | 234.32CM | 66.04CM |
| 4 SENSORS | 175.90CM | 58.42CM |
| 5 SENSORS | 134.80CM | 41.09CM |
| 6 SENSORS | 105.41CM | 29.4CM |

|  | GAP (IN.) | GAP REDUCTION (IN.) |
|---|---|---|
| 2 SENSORS | 118.25 |  |
| 3 SENSORS | 92.25 | 26 |
| 4 SENSORS | 69.25 | 23 |
| 5 SENSORS | 53.072 | 16.178 |
| 6 SENSORS | 41.5 | 11.572 |

SPRAY DISPENSER

CROSS REFERENCE TO RELATED APPLICATIONS

This application claims the benefit of U.S. Provisional Patent Application No. 61/536,453, filed Sep. 19, 2011.

REFERENCE REGARDING FEDERALLY SPONSORED RESEARCH OR DEVELOPMENT

Not applicable.

SEQUENTIAL LISTING

Not applicable.

BACKGROUND OF THE INVENTION

1. Field of the Invention

The present invention relates generally to a dispensing system for dispensing a fluid or product from a spray device, and more particularly, to a method and apparatus for discharging a product through a nozzle of an aerosol container from a dispensing system.

2. Description of the Background of the Invention

Aerosol containers are commonly used to store and dispense a product such as air freshening agents, deodorants, insecticides, germicides, decongestants, perfumes, or any other known products suitable for dispersal in the form of particles or droplets suspended within a gas. The product is forced from the aerosol container through an aerosol valve by a hydrocarbon or non-hydrocarbon propellant, or another compressed gas. Typical aerosol containers comprise a body with an opening at a top end thereof. A mounting cup is crimped to the opening of the container to seal the top end of the body to prevent leakage of the product or the propellant. The mounting cup is generally circular in geometry and may include an outer wall that extends upwardly from a base of the mounting cup to connect to the area of crimping. A pedestal also extends upwardly from a central portion of the base of the mounting cup. A valve assembly connected to the aerosol container includes a valve stem, a valve body, and a valve spring. The valve stem extends through the pedestal, wherein a distal end extends upwardly away from the pedestal and a proximal end is disposed within the valve body. The valve body is secured within an inner side of the mounting cup and a dip tube may be attached to the valve body. The dip tube extends downwardly into an interior of the body of the container. The distal end of the valve stem is axially depressed along a longitudinal axis thereof to open the valve assembly and thereby discharge the product through the valve assembly. In other aerosol containers, the valve stem is tilted or displaced in a direction transverse to the longitudinal axis of the container to radially actuate the valve stem. When the valve assembly is opened, a pressure differential between the container interior and the atmosphere forces the contents of the container out through an orifice of the valve stem.

To facilitate their use in various circumstances, the aerosol containers are often provided with one or more actuators. The actuators are configured to depress the valve stem of the aerosol container to release product, in some cases, through the actuator. Depending upon the application, the actuators can be manual or automated. Manual actuators include overcaps, buttons, levers, or triggers that, when depressed or otherwise activated, cause product to be dispensed from the aerosol container. Alternatively, the actuators can be operated by machinery residing within a housing that contains the aerosol container or that is otherwise attached thereto. In an automated dispensing system, for example, a motor may be coupled to an actuator that is configured to dispense product from an aerosol container. In that case, a timer may be connected to a motor that, in accordance with a predefined schedule, causes the motor to operate the actuator to dispense product. These mechanisms can be configured to dispense product into a particular volume, for example, to ensure that a certain quantity of freshening agents, deodorants, or insecticides are dispensed into a room containing the dispensing system.

Many conventional dispensing systems are only configured to contain a single product or fluid container and are, therefore, only capable of dispensing a single product. In the case of fragrance-dispensing systems, the constant dispensing of a single fragrance can quickly become tiresome for a user, particularly as the desire for a specific fragrance may vary throughout the day, or from day-to-day. Additionally, the constant dispensing of a single fragrance can lead to fragrance fatigue or habituation causing the user to realize a reduced benefit from the dispensed fragrance. In other applications, where the dispensers are used for the distribution of insecticides or germicides, the constant distribution of the same product or chemical may actually defeat the purpose of the system by promoting the development of resistant insects or germs. Additionally, a dispenser having only a single product container will require more regular refilling and is more likely to run out of product, resulting in regular periods of time during which the dispenser cannot operate and requiring regular user maintenance and attention. Accordingly, in many dispensing systems it is advantageous to provide the capability of dispensing more than one product.

A different problem associated with prior art automated dispensing systems is that they often dispense products when it is of little benefit to a user. If the system is configured to dispense product at regular intervals, and has no capability to detect the presence of an individual, for example, the system will continue to dispense product even when individuals are not present and cannot benefit from the product. This can be extremely wasteful.

Some conventional systems include a single motion sensor, and are configured to dispense product only when they detect movement (implying the presence of an individual or other suitable target) using that single motion detector. The accuracy of those systems, though, can be limited by the configuration of their motion detection systems. Because the motion detection systems of these dispensers have a specific field of vision, if a target does not happen to pass through that field of vision, or if the field of vision of the single motion detector is blocked by an obscuring structure, the individual will not be detected and the product will not be dispensed. For example, if a conventional dispenser having a single motion detector is positioned in a corner of a room, the motion sensor could become oriented toward one of the walls. In that case, at least a portion of the sensor's field of vision could become blocked by one of the room's walls, thereby diminishing the effectiveness of the motion sensor. As such, a single motion sensor arrangement forces the user to adjust the orientation and placement of the dispenser to optimize the sensing area, which may result in the dispenser being positioned in a location that does not conform with the overall design aesthetics of the room.

Another common drawback associated with prior art devices is the difficulty with which an aerosol container or batteries are loaded into or removed from the housing. To ensure that the actuating system incorporated into the housing is able to operate the valve assembly connected to the aerosol container, after the housing is closed, the container must be accurately positioned within the housing. If the actuator is not positioned correctly, the actuator may be incapable of operating the valve assembly to cause product to be dispensed, or may even damage the container. Conversely, and equally important, if the actuator is not accurately positioned, the actuator may be incapable of releasing the valve assembly to stop the dispensing of product, or the product may be partially released from the container because the container is not seated properly and the valve may be partially blocked. Similarly, if the batteries are not correctly positioned within the housing, the batteries may be incapable of enabling power to the device.

In conventional housings, the aerosol containers are often secured by a clamping system wherein a door or hinged portion of the housing is closed over the aerosol container to lock the container into position within the housing. These securing systems often allow a user to close the housing even if the container is not positioned accurately within the housing. Sometimes, when attempting to close the housing, a user may simply force the housing closed, possibly damaging the aerosol container and other components of the dispensing system.

SUMMARY OF THE INVENTION

According to one aspect of the invention, a dispensing system includes a housing adapted to retain at least two product or fluid-dispensing containers. The housing further includes a motion or other detecting system having a field of vision that extends about a perimeter of the dispensing system. The housing is adapted to dispense a product from at least one of the at least two aerosol containers in response to the detection of a parameter by at least one sensor.

According to a second aspect of the invention, a method of operating a dispensing system includes the step of alternating between active and lockout modes within a first timing sequence, wherein during the active mode at least one sensor is active to detect sensory input, and whereupon detection of the sensory input results in product being released from a first container, and wherein during a lockout mode product is not released from the first container. The method further includes the step of alternating between active and lockout modes within a second timing sequence, wherein during the active mode at least one sensor is active to detect sensory input, and whereupon detection of the sensory input results in product being released from a second container, and wherein during a lockout mode product is not released from the second container. The expiration of the first timing sequence, and the initiation of the second timing sequence, occurs from at least one of the lapsing of a time interval, sensory input, and manual input from a user.

According to another aspect of the invention, a method of operating a dispensing system includes the step of activating at least one sensor during a first timing sequences to detect sensory input, whereupon detection of the sensory input results in the release of product from a first container. The method further includes the step of activating a button, wherein actuation of the button for a duration of <a time period "T" results in no release of product, and wherein the depression of the button for a duration ≥T results in the release of product.

According to a further aspect of the invention, a dispenser includes a housing adapted to receive a first and second container therein and at least one sensor is associated with the housing. The dispenser provides for alternating between active and lockout modes within first and second timing sequences. The dispenser provides for alternating between active and lockout modes within first and second timing sequences. During the active mode sensory input from the at least one sensor results in product being released from the first or second container, respectively, and during a lockout mode product is not released from the first or second container, respectively.

According to a further aspect of the invention, a dispenser includes a housing adapted to receive first and second containers therein and an actuator drive system for selectively releasing product from the first and second containers. The actuator drive system includes first and second armatures for activation of the first and second containers, respectively.

According to a still further aspect of the invention, a dispenser includes a housing adapted to receive at least one container therein and a button disposed on the housing. The button comprises a top plate provided on a top end of the housing and includes at least one opening extending therethrough.

According to another aspect of the invention, a dispenser includes a housing having an aperture adapted to receive a container therein; and a pushbutton disposed on the housing. The button is a top plate of the housing and comprises about 25% to about 100% of the total viewable surface area of the housing when viewed from above.

According to another aspect of the invention, a spray dispenser includes a housing adapted to receive first and second containers and an actuator drive system for selectively releasing product from the two containers. The actuator drive system includes a motor, a drive train, and first and second actuator arms. Activation of the motor in a first direction causes the first actuator arm to activate the first container and activation of the motor in a second direction causes the second actuator arm to activate the second container.

According to a further aspect of the invention, a dispenser includes a housing for placement in a space, wherein the housing is adapted to receive at least one container having a material therein for emission into the space in response to at least one of a manual actuation and sensory input. At least three sensors are distributed around a perimeter of the housing for the detection of sensory input. In one embodiment, the at least 3 sensors are distributed around the perimeter such that if the housing is placed near an obstruction that blocks two of the at least three sensors, at least one of the remaining sensors is capable of detecting sensory input. In another embodiment, the space is a room having at least one corner of a wall that defines a right angle obstruction. In this embodiment, at least one of the at least three sensors is capable of dispensing sensory input if the housing is disposed adjacent the corner.

According to a still further aspect of the invention, a dispenser includes a housing adapted to receive at least one container therein and a plurality of sensors provided about a perimeter of the housing, wherein each sensor has a field of view in which the sensor may detect sensory input. A total viewing field of 360 degrees is provided about the housing. The sum of a field of view of the sensors about the total viewing field is at least between 20%-100% thereof. In one embodiment, the plurality of sensors are radially spaced from a longitudinal axis of the housing on the same plane. In a different embodiment, the housing has a geometric shape about the plane the plurality of sensors are provided on that is one of a square, rectangle, polygon, circle, and oval.

According to another aspect of the invention, a dispenser includes a housing adapted to receive at least one container therein and a plurality of sensors provided about a perimeter of the housing, wherein each of the sensors has a field of view to detect sensory input. At least one sensory gap exists between at least two of the plurality of sensors in which sensory input is not detected. In one embodiment, the plurality of sensors includes 3 sensors positioned about the perimeter of the housing, wherein if an additional sensor were provided about the perimeter of the housing the percentage reduction in the sensory gaps would be less than 25%. In a different embodiment, the plurality of sensors includes 4 sensors positioned about the perimeter of the housing, wherein if an additional sensor were provided about the perimeter of the housing the percentage reduction in the sensory gaps would be less than 20%.

According to another aspect of the invention, a method of operating a dispensing system includes the steps of providing a power source to a dispenser adapted to receive first and second containers therein and entering an active mode, wherein a sensor is activated to detect the presence of motion within a sensory path thereof. The method further includes the step of inquiring about the presence of the first and second containers upon the detection of motion by the sensor. If no container is present a dispensing operation is not undertaken, if one of the first or second containers is present a dispensing operation is undertaken with the present container, and if both the first and second containers are present the dispenser inquires about the current time period.

According to a still further aspect of the invention, a spray dispenser includes a housing having an aperture adapted to receive a container therein and a container detection arm, wherein the container detection arm includes a lever that extends into the aperture. Insertion of a container within the aperture causes flexure of the lever to contact a switch, thereby providing a signal to a controller of the presence of a container within the aperture. The housing further includes a second aperture adapted to receive a second container and a second container detection arm that includes a lever extending into the second aperture, wherein insertion of a container within the second aperture causes flexure of the lever to contact a second switch, thereby providing a signal to the controller of the presence of the second container within the second aperture.

According to another aspect of the invention a spray dispenser includes a housing adapted to receive a container therein, wherein the housing includes a plurality of apertures and a plurality of sensors disposed within the apertures, wherein the sensors detect a signal in a space around the housing. The apertures are not viewable by a user having a line of sight within X feet from one of the apertures and Y feet above one of the apertures.

According to a further aspect of the invention, a spray dispenser includes a housing adapted to receive a container therein, wherein the housing includes a sidewall and a fin disposed on the sidewall. A plurality of apertures are disposed in a lower face of the fin and the lower face of the fin defines a plane located at not less than 66 degrees from a longitudinal axis of the housing.

According to a still further aspect of the invention, a spray dispenser includes a housing having a plurality of apertures disposed therein and a plurality of sensors disposed within the apertures. The housing further includes an overhang portion disposed above the apertures having a length and a height above the bottom of the aperture, and a ration of the height to the length exceeds 2.17.

BRIEF DESCRIPTION OF THE DRAWINGS

FIGS. 29A-29F illustrate various sensing parameters based on the use of varying numbers of sensors;

FIGS. 30A-30F are overhead illustrations of a conventional 12 ft×12 ft (3.66 m×3.66 m) room illustrating the coverage area of dispensers 100 having different numbers of motion sensors;

FIGS. 31A-31F are overhead illustrations of a conventional 16 ft×16 ft (4.88 m×4.88 m) room illustrating the coverage area of dispensers 100 having different numbers of motion sensors with the room being in a first arrangement;

FIGS. 32A-32F are overhead illustrations of a conventional 16 ft×16 ft (4.88 m×4.88 m) room illustrating the coverage area of dispensers 100 having different numbers of motion sensors with the room being in a second arrangement;

FIGS. 33A-33F are overhead illustrations of a conventional 16 ft×16 ft (4.88 m×4.88 m) room illustrating the coverage area of dispensers 100 having different numbers of motion sensors with the room being in a third arrangement;

FIGS. 34A-34F are overhead illustrations of a conventional 18 ft×13 ft (5.49 m×5.49 m) room illustrating the coverage area of dispensers 100 having different numbers of motion sensors;

FIGS. 35A-35E are schematic illustrations showing fields of view for dispenser 100 having 2, 3, 4, 5, and 6 sensors, respectively;

DETAILED DESCRIPTION OF THE DRAWINGS

FIGS. 1-5 depict one embodiment of a dispenser 100. The dispenser 100 generally comprises a housing 102. The dispenser 100 is configured to discharge product from one or more containers disposed within the housing 102 upon the occurrence of a particular condition. The condition could be the manual activation of the dispenser 100 or the automatic activation of the device in response to an elapsed time interval or signal from a sensor, such as a motion sensor or other types of sensors as later discussed. The product dispensed may include a fragrance, insecticide, or other product disposed within a carrier liquid, a deodorizing liquid, or the like. For example, the fluid may comprise OUST™, an air and carpet sanitizes for household, commercial, and institutional use, or GLADE®, a household deodorant, both sold by S.C. Johnson and Son, Inc., of Racine, Wis. The fluid may also comprise other actives, such as sanitizers, air and/or fabric fresheners, cleaners, odor eliminators, mold or mildew inhibitors, insect repellents, and the like, or that have aromatherapeutic properties. The fluid alternatively comprises any fluid known to those skilled in the art that can be dispensed from a container, such as those suitable for dispersal in the form of particles or droplets suspended within a gas. The dispenser 100 is therefore adapted to dispense any number of different fluid or product formulations. In embodiments that utilize more than one container, the fluid or product within the containers may be the same, similar, or different.

Figure 1:
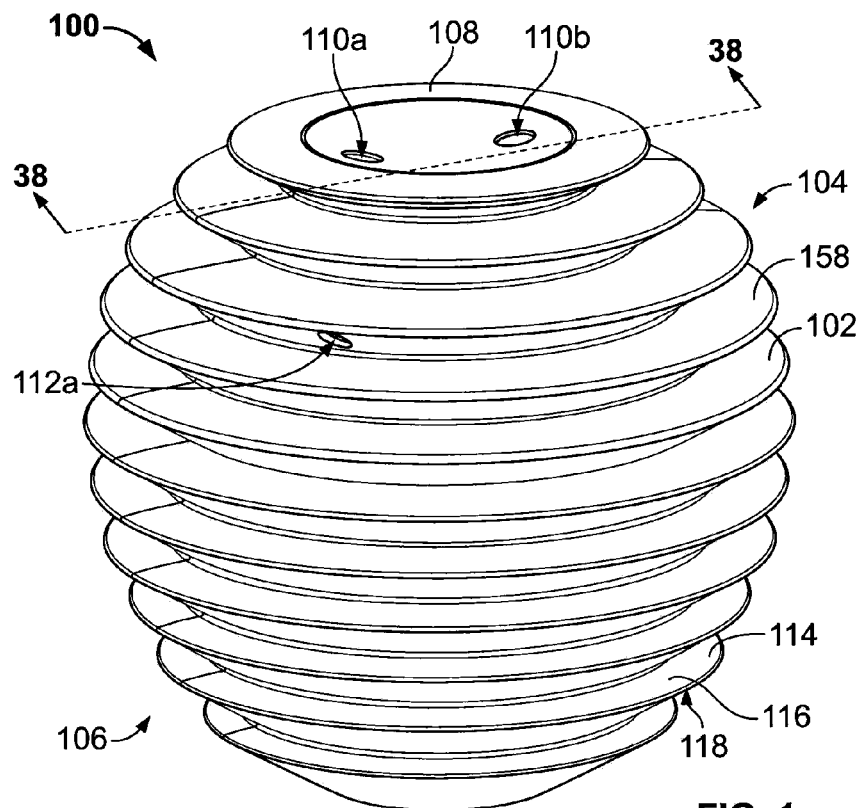
FIG. 1 is an isometric view of one embodiment of a housing for a dispenser.

Turning to FIG. 1, the housing 102 generally has the shape of a prolate spheroid truncated at upper and lower portions thereof. In other implementations, though, the outward geometry of dispenser 100 may have any appropriate shape for housing the contents of dispenser 100, while being relatively stable when placed upon a flat, horizontal surface. Possible shapes include cubes or boxes, pyramids (or other polyhedrons), or other three-dimensional shapes being configured to stand upon a flat surface.

In the present embodiment the housing is separated into a top section 104 and a bottom section 106, which are joinable to form the housing 102. The top section includes a circular top plate 108 that functions as a button for activation of the dispenser 100, which will be described with greater particularly hereinbelow. The top plate 108 includes a generally planar peripheral edge and a central concave depression. In one embodiment, the top plate 108 has a total surface area of approximately 5.9 square inches (38.06 square cm). In that case, when viewed from above, the viewable surface of the top plate 108 comprises approximately 34% of the total viewable surface area of the housing 102. In other embodiments, the top plate 108 comprises about 25% to about 100% of the total viewable surface area. In another embodiment, the top plate 108 comprises about 50% to about 100% of the total viewable surface area. In yet another embodiment, the top plate 108 comprises about 75% to about 100% of the total viewable surface area. Openings 110a, 110b are provided within the central depression. The top section 104 also includes four apertures 112 equidistantly spaced within a sidewall 113 of the housing 102, which act as ports for four sensors disposed within the housing 102. The bottom section 106 includes a generally planar bottom portion for supporting the dispenser 100 on a support surface.

The housing 102 may be constructed from any suitable material, such as plastic, metal, glass, or combinations thereof. Additionally, the materials may include combinations of manufactured, natural, and recycled or reclaimed materials. In some cases, the materials are selected from, or include manufactured materials configured to approximate, naturally occurring substances, such as wood, stone, paper, or rock, or combinations thereof. Any such materials can be selected based upon their having a natural looking appearance and/or a natural feeling to the touch. By incorporating natural materials, or analogs of natural materials, the dispenser 100 can be made to look more appropriate for placement in an outdoors location, such as in a sun room or on a balcony, or can complement the look and feel of existing natural objects within the home.

In the present embodiment, the sidewall of the housing 102 includes a plurality of fins 114 extending radially therefrom. Each fin 114 has an upper face 116 with a slightly convex configuration (see, for example, FIG. 6), which projects horizontally away from the sidewall 113 of the dispenser 100. A lower face 118 of each fin 114 is generally planar and also extends outwardly from the sidewall 113 of the housing 102 at an angle of approximately 45 degrees with respect to the upper face 116. In other embodiments one or more of the fins 114 may have upper and lower faces 116, 118 with curved or planar surfaces that may be provided at any angle with respect to one another. For example, the fins 114 may be rounded and curvilinear or may comprise relatively planar structures having a low surface profile. In some embodiments, the fins 114 provide a user with an improved gripping surface when lifting, moving, or opening the dispenser 100. In other embodiments, the housing 102 may be provided with other radially or non-radially extending projections or may comprise no projections.

Figure 2:
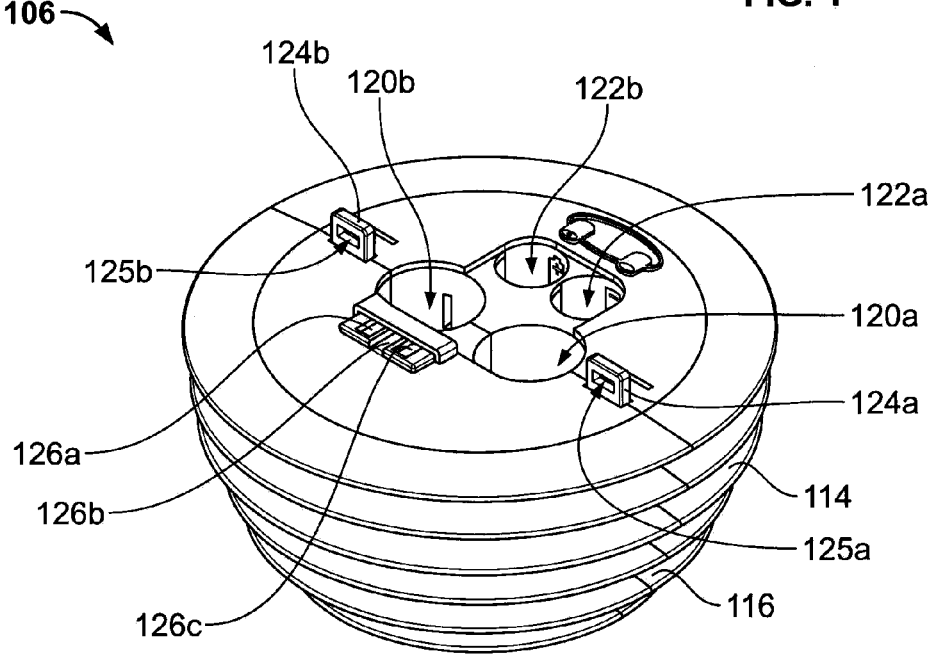
FIG. 2 is an isometric view of a bottom section of the housing of FIG. 1.

FIG. 2 depicts the bottom section 106 of the housing 102. The bottom section 106 includes a number of apertures for receiving containers and batteries. In the present embodiment, the bottom section 106 includes two apertures 120a, 120b that are each sized to receive at least a portion of a container. Apertures 120a, 120b have a generally circular configuration to match the outer geometry of a conventional aerosol container or other conventional fluid or product container. The apertures 120a, 120b are preferably sized to allow containers to be easily placed therein and subsequently removed by a user who may replace the container with a refill.

The bottom section 106, as depicted in FIG. 2, also includes apertures 122a, 122b, which are sized to receive batteries or other power units for providing electrical energy to one or more of the components of the dispenser 100. As such, the size of the apertures 122a, 122b can be adjusted depending upon the dimensions of the batteries used to power the dispenser 100. Where a different number of batteries are necessary for powering the system, the number and size of the apertures 122 may be adjusted to hold an appropriate number of batteries. In one embodiment, the apertures 122a, 122b are sized to receive at least a portion of an AA-sized battery. Electrical contacts are provided at the bottom of each aperture 122a, 122b for placement in contact with corresponding contacts of a battery when a battery is disposed therein. In some cases, when the dispenser 100 is powered via an external power source, such as an external power adapter, the apertures 122a, 122b may be omitted or supplemented by such external power source.

FIG. 2 further depicts the bottom section 106 as having locking tabs 124a, 124b. The locking tabs 124a, 124b are adapted to couple the bottom section 106 to the top section 104, which will be described in greater detail hereinbelow. As shown in the embodiment of FIG. 2, the locking tabs 124 may comprise a generally rectangular structure with a rectangular aperture 125 or window extending therethrough. In other embodiments, the locking tabs 124 may comprise structures having different shapes defining differently shaped apertures. The apertures 125 are sized to receive and couple with corresponding locking mechanisms on the top section 104.

The top surface of the bottom section 106 of the dispenser 100 is relatively clear of other obstructions and mechanical elements so as to not confuse the user during the refilling of the containers 150 and the batteries 152. Additionally, the design of the bottom section 106 makes the dispenser 100 look less like a mechanical device and more like a décor item. Having the device be considered more of a décor item makes the user more likely to position the device in a prominent position within a living space, which consequently improves the performance of the dispenser 100 within that living space.

Electrical connectors 126a, 126b, 126c are disposed on the bottom section 106 and are placed in electrical connection with one or more components disposed within the bottom section 106, such as an actuator drive system and a mode selector switch, which are each described in more detail below.

Figure 3:
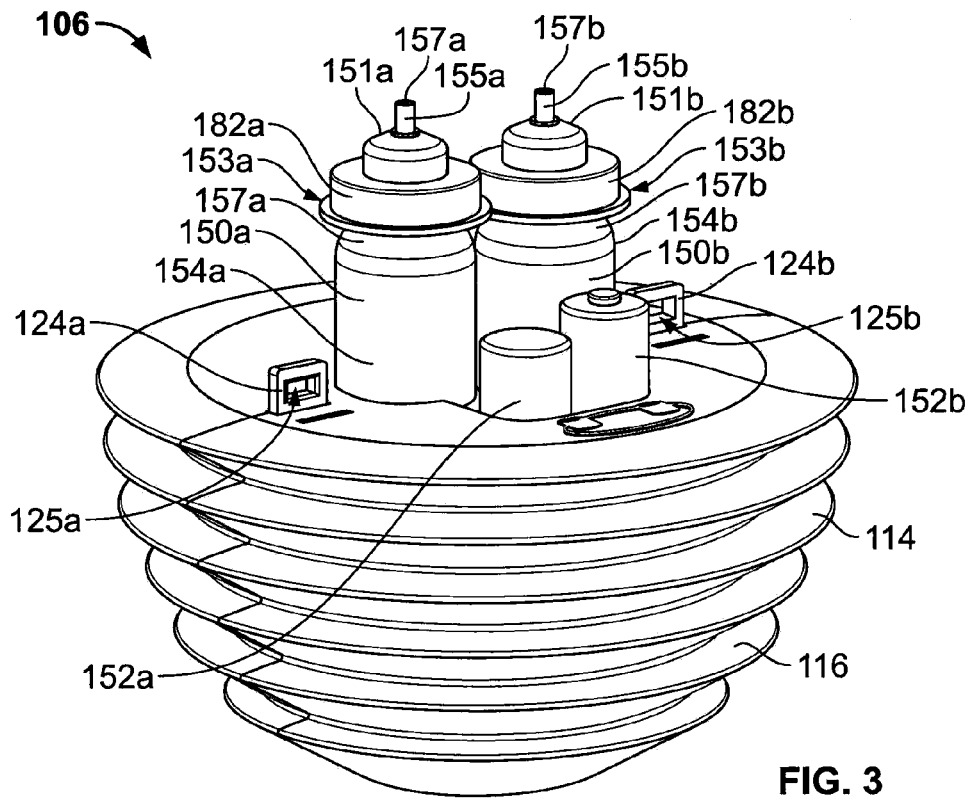
FIG. 3 is an isometric view of the bottom section of FIG. 2, further including two aerosol containers and two batteries.

FIG. 3 depicts the bottom section 106 of the housing 102 as further including several containers and batteries inserted therein. Specifically, containers 150a, 150b, which may be conventional aerosol containers, are inserted into the apertures 120a, 120b (shown in FIG. 2), respectively. The containers 150a, 150b are inserted so as to orient the valve assemblies thereof upwards and away from the bottom section 106 of the housing 102. After insertion of the containers 150a, 150b, a portion of each container is exposed to allow for a user to grasp each container and remove same from the bottom section 106. In one embodiment, the containers 150a and 150b extend outwardly from the bottom section 106 by at least 1.27 cm, in light of the fact that the average finger width is 1.27 cm, which allows the user to more easily grip the containers.

Similarly, batteries 152a, 152b are inserted into the apertures 122a, 122b, respectively. Upon insertion, the batteries 152 are oriented so as to establish the appropriate electrical interconnections with terminals disposed at the bottom of the apertures 122a, 122b. This arrangement simplifies the installation or replacement of the batteries 152 as the batteries 152 are not locked into place and can be easily gripped and removed by the user. In one implementation, after insertion into the apertures 122a and 122b of the bottom section 106, the batteries 152 are exposed by more than 50% and can be easily gripped by the user and removed. The user can then easily drop new batteries in the apertures 122a and 122b to replace the batteries 152 as the batteries do not need to be snapped or otherwise affixed into place.

In the present embodiment, the containers 150a, 150b are containers configured to dispense product using a propellant such as a hydrocarbon or non-hydrocarbon propellant. Non-hydrocarbon propellants may include, but are not limited to, compressed gasses, including, for example, compressed air, nitrogen, nitrous oxide, inert gases, carbon dioxide, etc., and mixtures thereof. In other embodiments, the containers 150a, 150b may include—type sprayer containers or any other product dispensing containers. The containers 150a, 150b may include any appropriate activation mechanism, such as valves, delivery tubes and/or nozzles, or combinations thereof. The valves may have various different configurations such as tilt valves, axial valves, or metered valve systems.

The containers 150a, 150b may also comprise any size and volume known to those skilled in the art. In one embodiment, one or more of the containers 150a, 150b may comprise a small container, such as a mini-aerosol container sold by S.C. Johnson and Son, Inc., of Racine, Wis., which has a capacity of 12.2 g of product. Other example capacities for one or more of the containers 150a and 150b include 22.7 g and 175 g, though other capacities may be utilized. For example, it is contemplated that an aerosol or non-aerosolized container may have a capacity between about 5 g to about 300 g. Embodiments using smaller containers allow for a more compact implementation of the dispenser 100. Additionally, the smaller containers are easier to manage and drop into their respective apertures within the bottom section 106 of the dispenser 100. Accordingly, the smaller contains may be easier for a user to manage during replacement and/or installation.

Figure 6:
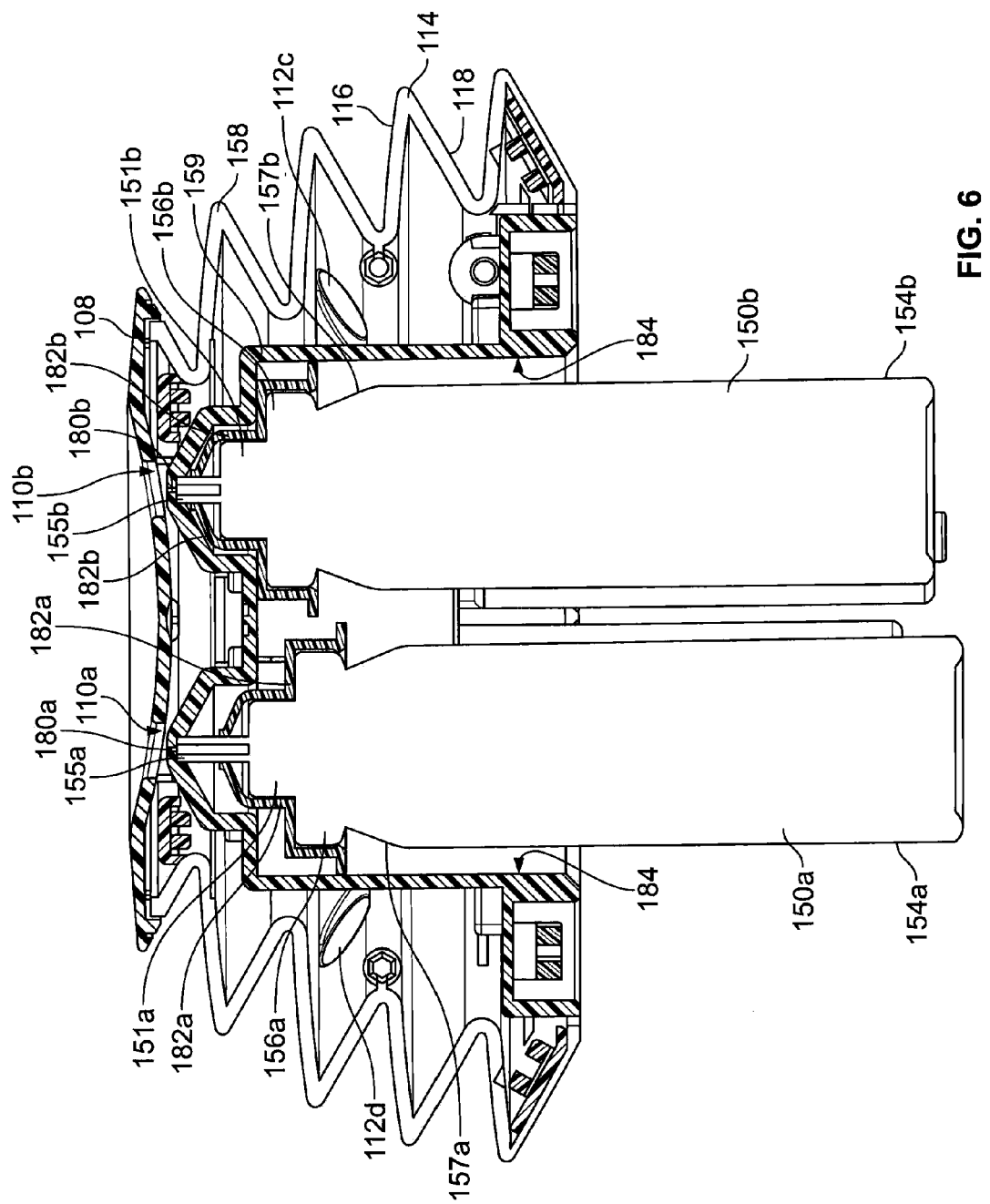
FIG. 6 is a partial section view of the top section of the housing of FIG. 5 with portions behind the plane of section removed for purposes of clarity.

In one embodiment, the containers 150a, 150b are aerosol containers comprising bodies 154a, 154b with mounting cups 156a, 156b crimped to a top end thereof (see FIG. 6). The mounting cups 156a, 156b are generally cylindrical in shape and include an outer wall that extends circumferentially therearound. In the present embodiment a plastic sheath or hat surrounds portions of the mounting cup's 156a, 156b. Necks 157a, 157b of the containers 150a, 150b are disposed below the mounting cups 156a, 156b, wherein the necks 157a, 157b are angled inwardly with respect to the mounting cups 156a, 156b and the remaining area of the bodies 154a, 154b. Pedestals 151a, 151b extend upwardly from a central portion of the mounting cups 156a, 156b. Valve assemblies 153 are provided within the containers 150a, 150b and include a valve stem 155a, 155b, wherein a distal end of the valve stem 155a, 155b extends through the pedestal 151a, 151b. When the distal end of the valve stem 155a, 155b is depressed, the valve assembly 153a, 153b is opened and the contents of the container 150a, 150b are discharged through the valve stem 155a, 155b. The contents of the containers 150a, 150b may be discharged in a continuous or metered dose. Further, the discharging of the contents of the container 150a, 150b may be effected in any number of ways, e.g., a discharge comprising a partial metered dose, a discharge through a partial opening of the valve assembly 153a, 153b, multiple consecutive discharges, etc.

Figure 4:
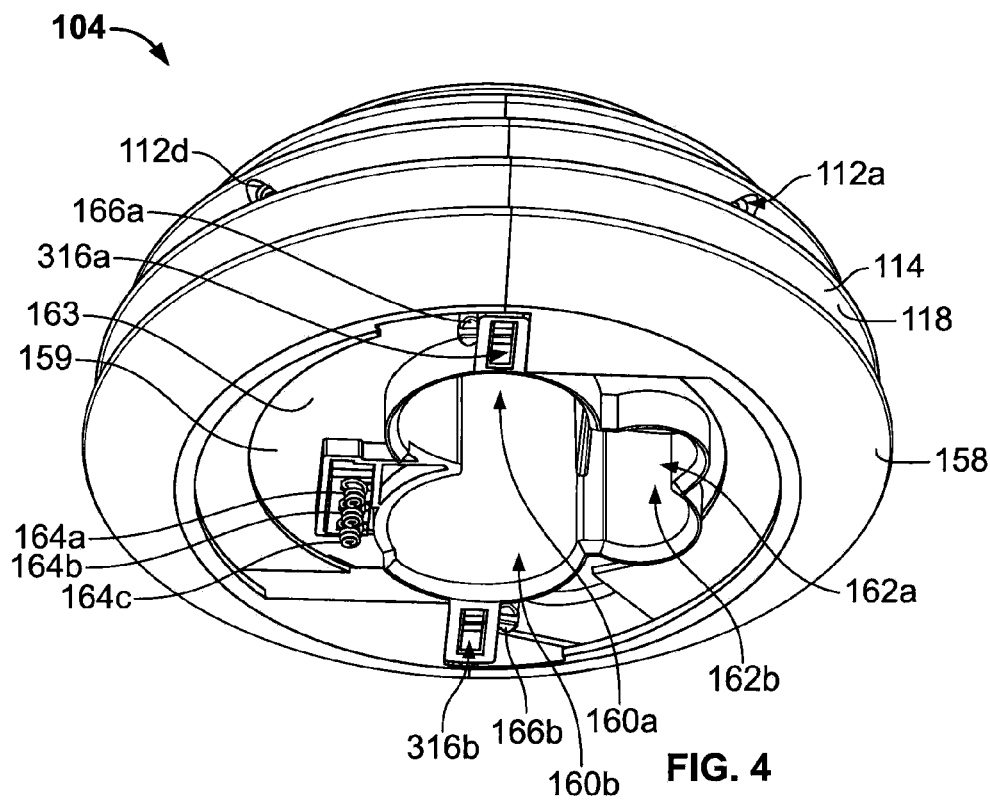
FIG. 4 is a bottom isometric view of a top section of the housing of FIG. 1.
Figure 5:
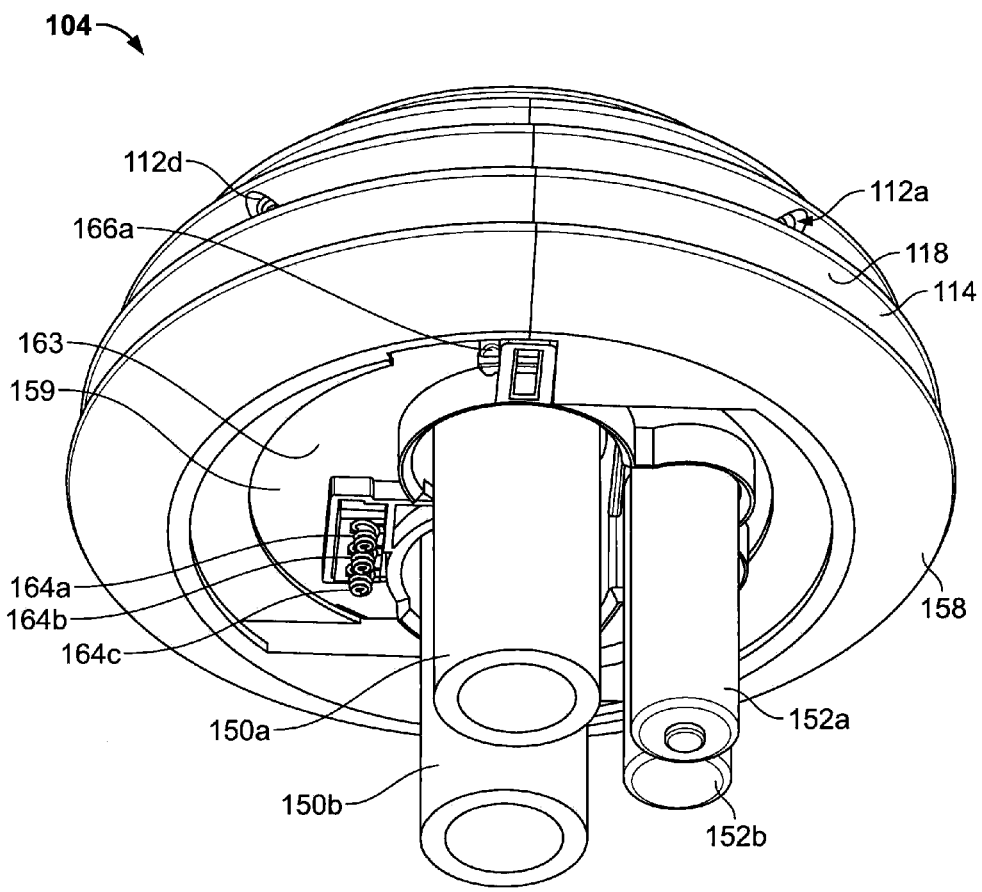
FIG. 5 is an isometric view of the top section of FIG. 4, further including two aerosol containers and two batteries.

FIGS. 4 and 5 show the top section 104 of the housing 102. With respect to FIG. 5, the containers 150a, 150b and the batteries 152a, 152b are shown in their operational state as if the top section 104 were connected to the bottom section 106, as further described below. The top section 104 includes an upper sidewall 158 configured to house the components of the top section 104, including the PCB or substrate housing the device's controller, the optical sensors of the motion-detecting system and the components of the top plate 108, which may function as a manual control button for the dispenser 100. A cap assembly 159 is also mounted within and retained by the top section 104 and is configured to rotate within the upper sidewall 158.

With respect to FIG. 4, the cap assembly 159 is shown to include two apertures 160a, 160b, which are sized to receive at least a portion of one of the containers 150a, 150b, respectively. The apertures 160a, 160b are preferably sized to allow the containers to slide into and out of the apertures 160a, 160b. When the top section 104 is connected to the bottom section 106 of the housing 102, the apertures 160a, 160b are positioned over the apertures 120a, 120b (shown in FIG. 2). The apertures 160a, 160b are sized to receive a portion of each container 150a, 150b that projects from the apertures 120a, 120b within the bottom section 106. For example, FIG. 3 depicts portions of the containers 150a, 150b extending upwardly from the bottom section 106 and FIG. 5 depicts the placement of the containers 150a, 150b within the top section 104 as if the top and bottom sections were combined.

The cap assembly 159 also includes apertures 162a, 162b, which are sized to receive a top portion of the batteries 152a, 152b, respectively. When the top section 104 is connected to the bottom section 106, the apertures 122a, 122b (shown in FIG. 2) are aligned with the apertures 162a, 162b, respectively.

Turning again to FIG. 4, the apertures 160a, 160b and 162a, 162b are circumscribed by a raised wall that extends from a bottom surface 163 of the cap assembly 159. Also, as shown in FIG. 4, the various apertures 160a, 160b and 162a, 162b may be formed within the cap assembly 159 so as to be coextensive with one another. In the example implementation shown in FIG. 4, the apertures 160a, 160b and 162a, 162b do not define independent and separate recesses within the cap assembly 159. Instead, the apertures 160a, 160b and 162a, 162b are formed so as to define a single, combined aperture including different regions that are each configured to receive either an aerosol container or a battery. In other implementations, though, the apertures 160a, 160b, 162a, and 162b may each define independent and separate recesses within the cap assembly 159. In still other implementations, different combinations of the apertures 160a, 160b, 162a, and 162b may be combined with one another, for example, to facilitate manufacturing processes or use by a user (for example, insertion of containers or batteries therein). Each region of the combined apertures 160a, 160b and 162a, 162b comprises an outer wall having a curvature configured to approximately match a portion of an outer surface of either the container 150a, 150b or the battery 152a, 152b to be disposed therein.

Three spring contacts 164a, 164b, 164c are provided on the bottom surface 163 of the cap assembly 159 to allow for an electrical connection to be formed between the top section 104 and the bottom section 106 of the housing 102. Each one of spring contacts 164a, 164b, 164c comprises a conductive spring that is configured to contact one of the electrical connectors 126a, 126b, 126c mounted on a top surface of the bottom section 106 (shown in FIG. 2) when the top section 104 is connected to the bottom section 106. Electrical interconnects (not shown) are formed between the spring portion of spring contacts 164a-c and a controller disposed within the top section 104 to place the controller in communication with the components of the bottom section 106. This arrangement allows for the separation of electrical functionality between the top section 104 and the bottom section 106 of the dispenser 100. As such, the motion sensing system may be disposed within the top section 104 to allow for higher visibility of the surroundings of the dispenser 100, while the actuator drive system may reside in the bottom section 106 to provide for more stability of the dispenser 100.

Locking members 166a, 166b are provided adjacent the bottom surface 163 of the top section 104. Each of the locking members 166a, 166b is sized to couple with one of the locking tabs 124a, 124b on the bottom section 106 when the top section 104 is connected thereto. The interaction between the locking members 166a, 166b and the locking tabs 124a, 124b is discussed in detail below.

With reference now to FIG. 6, the cap assembly 159 is shown to incorporate nozzles 180a, 180b positioned in fluid communication with the valve stems 155a, 155b of the containers 150a, 150b to facilitate product dispersal therefrom. Because the nozzles 180a, 180b are integrated into the cap assembly 159, it is not necessary to incorporate a secondary nozzle into each of the containers 150a, 150b to ensure appropriate product dispersal from each container.

In a preferred embodiment, the containers 150a, 150b are provided with a sheath 182a, 182b or hat that extends over portions of the containers. In the present embodiment, the sheathes 182a, 182b generally conform to and extend around the mounting cups 156a, 156b, the pedestals 151a, 151b, and portions of the valve stems 155a, 155b. Inner walls 184 defining the apertures 160a, 160b of the cap assembly 159 are configured to conform to the outer surface of the containers 150a, 150b, including the sheaths 182a, 182b of the present embodiment. Accordingly, as the containers 150a, 150b are inserted into the apertures 160a, 160b, the inner walls 184 constrain the movement of the containers 150a, 150b to ensure that the containers 150a, 150b are positioned in a manner that their corresponding valve stems 155a, 155b are in fluid communication with the nozzles 180a, 180b of the cap assembly 159.

In the present arrangement, as the containers 150a, 150b are pressed farther into the apertures 160a, 160b of the cap assembly 159 the surfaces defining the nozzles 180a, 180b depress the valve stems 155a, 155b to cause a valve assembly of the container 150a, 150b to open, thereby allowing the contents of the container 150a, 150b to be discharged through the valve stems 155a, 155b of the containers 150a, 150b and through the nozzles 180a, 180b of the cap assembly 159. Accordingly, to discharge the contents of either container 150a, 150b, the container is pressed upwardly into the container's respective aperture 160a, 160b of the cap assembly 159. Depending upon the method of discharging product from the container 150a, 150b, the valve stem 155a, 155b of the container may become seated within surfaces defining the opening of the nozzle 180a, 180b during actuation. Alternatively, the valve stem 155a, 155b may be seated within a shallow peripheral recess surrounding the opening of nozzles 180a, 180b. Depending upon the implementation, the valve stems 155a, 155b may always be slightly seated within the opening or recess of the nozzle 180a, 180b in an actuated or non-actuated state to provide proper alignment. In some embodiments, the valve stems 155a, 155b may already be slightly pre-loaded to assist in the actuation process.

Figure 7:
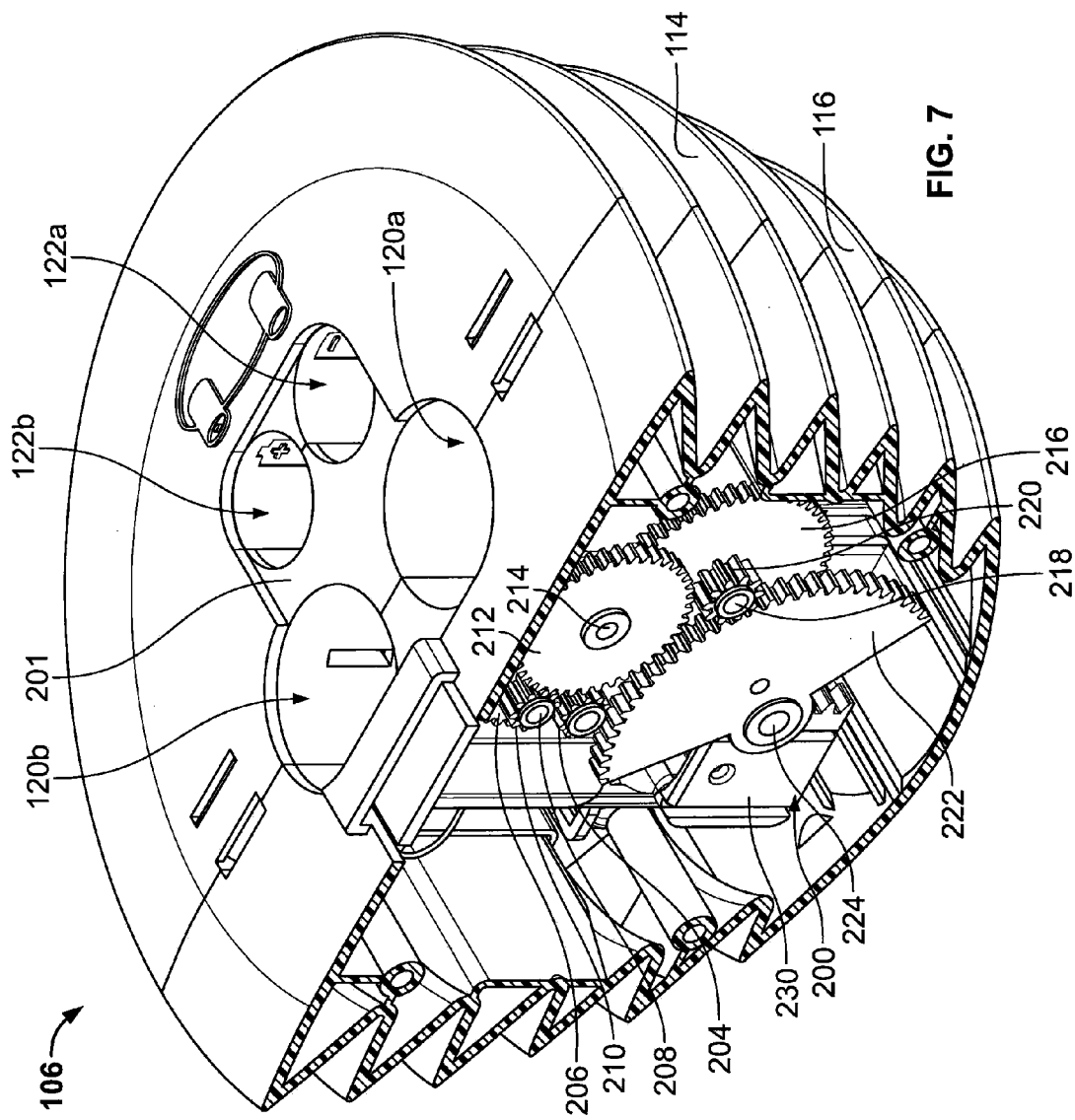
FIG. 7 is a partial, isometric sectional view of the bottom section of the housing shown in FIG. 2.
Figure 8:
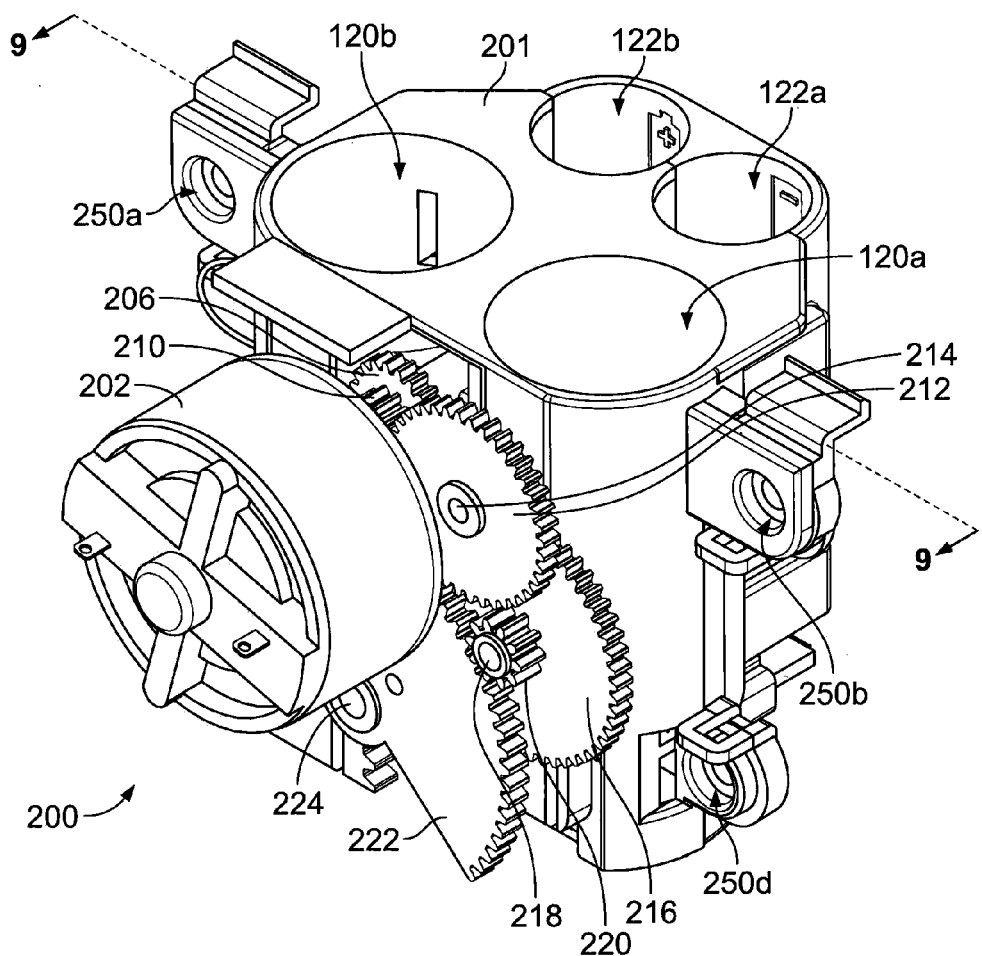
FIG. 8 is an isometric view of an actuator drive system and a housing.
Figure 9:
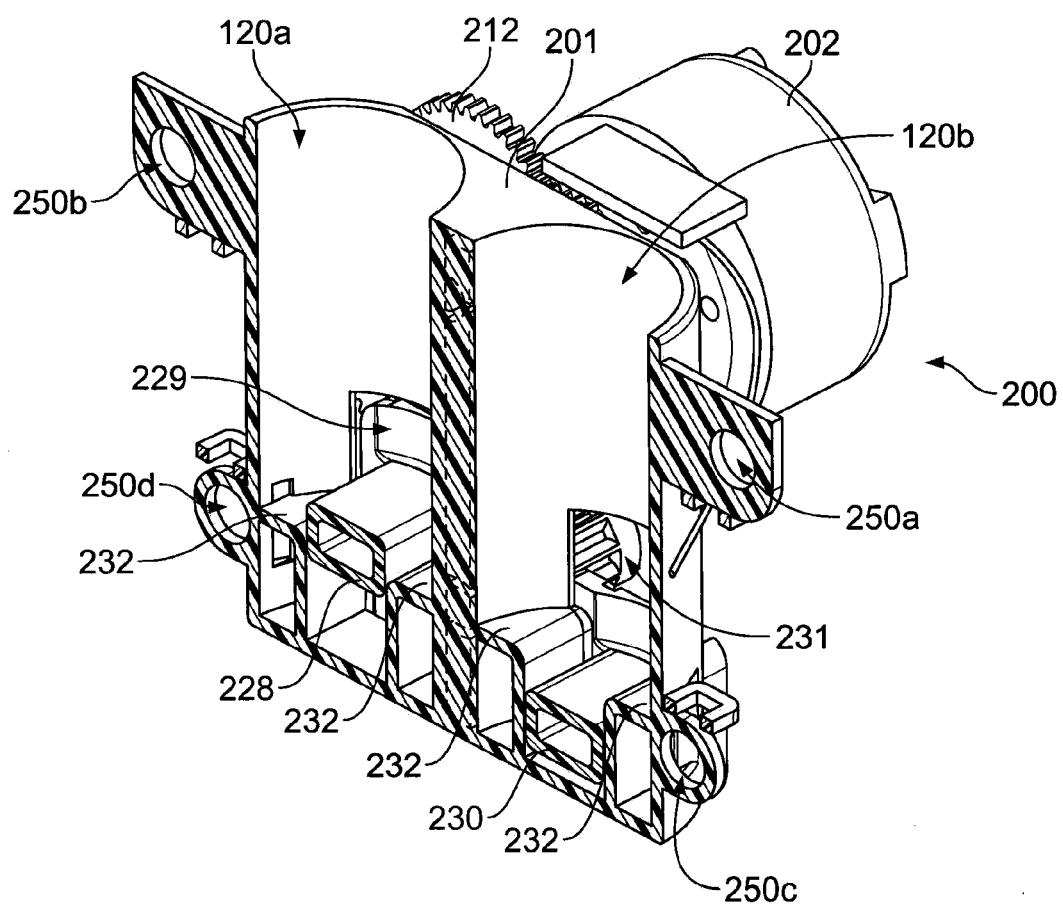
FIG. 9 is a cross sectional view of the actuator drive system and housing taken along the line 9-9 of FIG. 8.

An actuator drive system is used to selectively discharge product from either of the containers 150a, 150b. FIGS. 7-9 illustrate one embodiment of an actuator drive system 200 of the dispenser 100. The actuator system 200 is mounted within the bottom section 106 of the housing 102 and is controlled by electronic control signals received by a controller disposed within the top section 104 of the housing 102. With specific reference to FIG. 7, a view similar to that of FIG. 2 is shown, except that a portion of the sidewall covering the bottom section 106, a gear plate 252 (shown in FIGS. 10A and 10B), and the locking tabs 124a, 124b have been removed to better show the actuator drive system 200 contained therein FIG. 8 shows the actuator drive system 200 and a housing 201 for the apertures 120a, 120b and 122a, 122b with the remaining portions of the sidewall removed for purposes of clarity.

The actuator drive system 200 includes a number of gears that are coupled to an electric motor 202 for manipulating the actuator drive system 200. The motor 202 is, in turn, controlled by a controller located in the top section 104 of the housing 102 that controls the motor 202 based upon a current mode of operation of the dispenser 100 and the status of one or more sensors and user interfaces such as buttons or toggle switches. Depending upon the system implementation, the drive system may incorporate any suitable number of gears having appropriate numbers of teeth. As such, the gear ratios of the drive system may be adjusted, for example, based upon a strength of the connected motor, or power consumption considerations. Referring to FIGS. 7-9, the drive motor 202 (not shown in FIG. 7) is coupled to a drive gear 204. Teeth of the drive gear 204 engage with teeth of a gear 206, which is configured to rotate about an axle 208. The gear 206 is fixed to a smaller gear 210 that is also configured to rotate about axle 208. The teeth of the gear 210 engage with the teeth of a gear 212, which is configured to rotate about axle 214. The gear 212 is fixed to a gear 215 (shown on FIG. 12) that is configured to rotate about the axle 214. Teeth of the gear 215 engage with the teeth of a gear 216, which is configured to rotate about an axle 218. The gear 216 is fixed to a gear 220 that is configured to rotate about an axle 218. Teeth of the gear 220 engage with teeth of a gear 222 that is configured to rotate about an axle 224. As shown in FIG. 7, the geometry of the gear 222 may comprise a sector of a larger circular gear. In that case, the size of the gear 222 and the number of teeth thereon are selected to allow the actuator drive system 200 to operate while ensuring that the teeth of gear 222 are consistently engaged with the teeth of the gear 220. The gear 222 is fixed to a smaller gear 226 (see FIGS. 11-14 and 16), which is configured to rotate about the axle 224. The gear 226 engages with teeth formed along inner walls of armatures 228 and 230 (see elements 234 and 236, respectively, in FIGS. 11-17) in a rack and pinion arrangement. Accordingly, as the gear 226 rotates in a first direction, the armature 228 is raised while the armature 230 is lowered. Conversely, as the gear 226 rotates in the opposite direction, the armature 228 is lowered while the armature 230 is raised. As illustrated in FIG. 9, both of the armatures 228 and 230 penetrate into the volume defined by the apertures 120a, 120b through windows 229 and 231, respectively.

For purposes of better understanding the present actuator drive system 200 an example of the operation of same will be given. In the present example, the motor 202 rotates the drive gear 204 in a clockwise direction. The clockwise rotation of the drive gear 204 causes the gears 206 and 210 to rotate in a counter-clockwise direction about the axle 208. The counter-clockwise rotation of the gear 210 causes the gear 212 and the small gear 215 fixed to the gear 212 to rotate in a clockwise direction about the axle 214. The clockwise rotation of the gear 215 fixed to the gear 212 causes the gears 216 and 220 to rotate in a counter-clockwise direction about the axle 218. The counter-clockwise rotation of the gear 220 causes the gears 222 and 226 to rotate in a clockwise direction about the axle 224. The clockwise rotation of the gear 226 causes the armature 228 to be lowered within its aperture 120b of the bottom section 106, while the armature 230 is raised within its aperture 120a. Conversely, if the motor 202 rotates the drive gear 204 in a counter-clockwise direction, the armature 228 will be raised, while the armature 230 is lowered by an equal distance. By raising or lowering each of the armatures 228 and 230, as described below, the motor 202 (and the connected controller) can control a position of the containers 150a, 150b within the apertures 120a, 120b (and, consequently, the apertures 160a, 160b) and can cause product to be dispensed from either of the containers 150a, 150b by raising the desired container until the container's valve stem 155*a*, 155*b* contacts the nozzle 180*a*, 180*b* of the cap assembly 159 (see FIG. 6).

Turning to FIGS. 8 and 9, connection apertures 250*a*, 250*b*, 250*c*, 250*d* are provided for mounting the actuator drive system 200 to the housing 201 containing the apertures 120*a*, 120*b*. In other implementations, the connection apertures 250 may be replaced by snap-fit or quick-release connections allowing the actuator drive system 200 to be quickly connected to the housing 201. The installation of the actuator drive system 200 within the bottom section 106 of the housing 102 provides significant advantages over prior art systems. Namely, such a dispenser is provided with a lower center of gravity because a significant portion of the weight of the dispenser 100 is within the bottom section 106. Further, placement of a portion of the containers 150*a*, 150*b* and the batteries 152*a*, 152*b* into the bottom section 106 also assists in moving the center of gravity of the dispenser 100 downwardly within the housing 102. An increased center of gravity within the bottom section 106 as compared to the top section 104 provides for greater stability and reduces the chance of inadvertent tipping of the dispenser 100. In addition to providing greater stability, by locating the center of gravity of the dispenser 100 within the lower section 106, the user is provided with a tactile feature by which to identify the correct up/down orientation of the dispenser 100 as the weighting distribution provides ready cues as to how to orient (and thereby open) the device. The weighting of the bottom section 106 provides a similar and recognizable feeling to the dispenser 100 as that of objects commonly found in consumers' homes, such as jars, bottles, or other products that have a lid removed via a twisting action. The distribution of weight within the dispenser 100 also provides additional value to the user by allowing the user to recognize that the dispenser 100 is not hollow, thereby giving the dispenser 100 a high-quality feel.

Figure 10A:
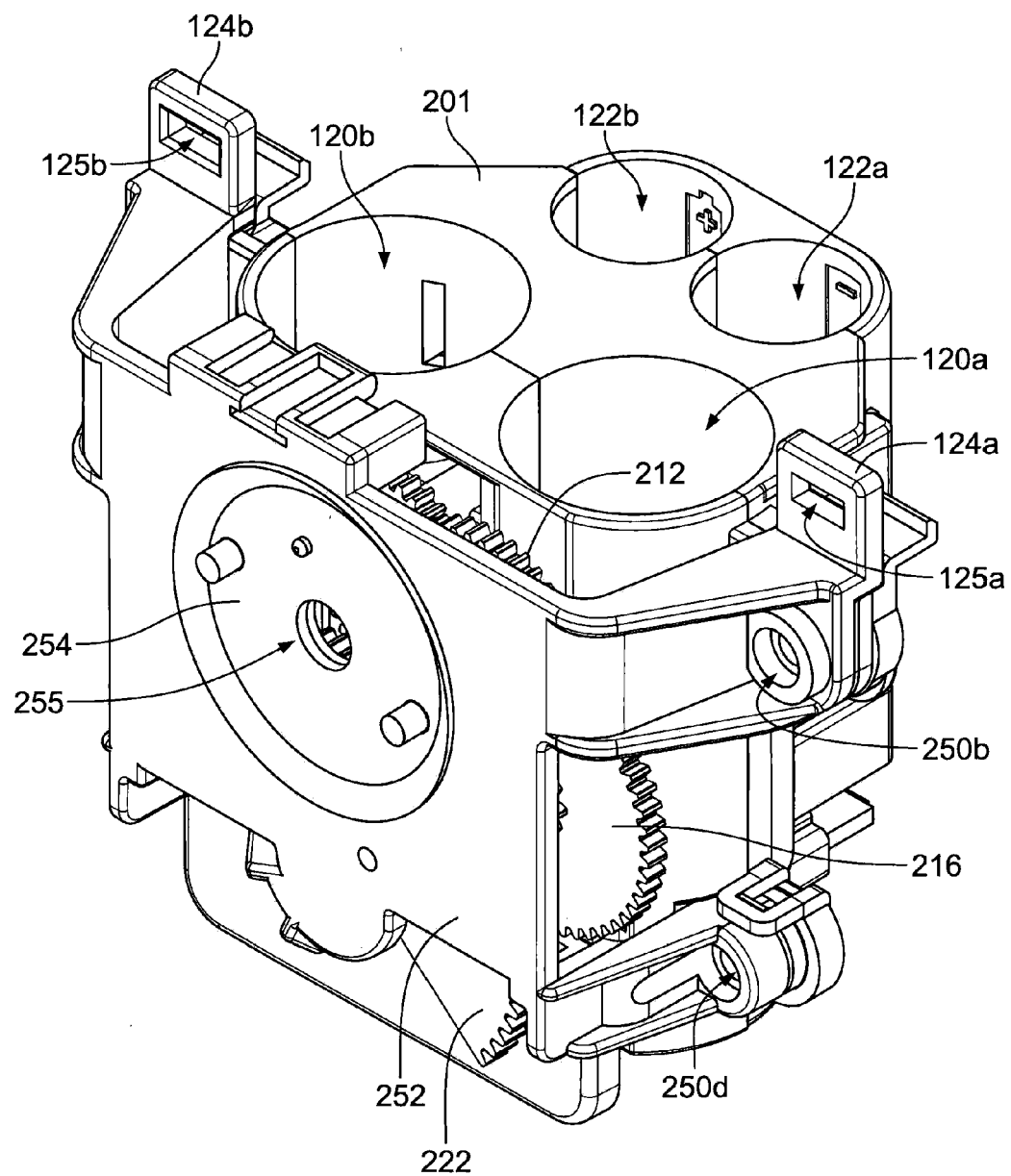
FIG. 10A is an isometric view of the actuator drive system and housing of FIG. 8, further including a gear plate.
Figure 10B:
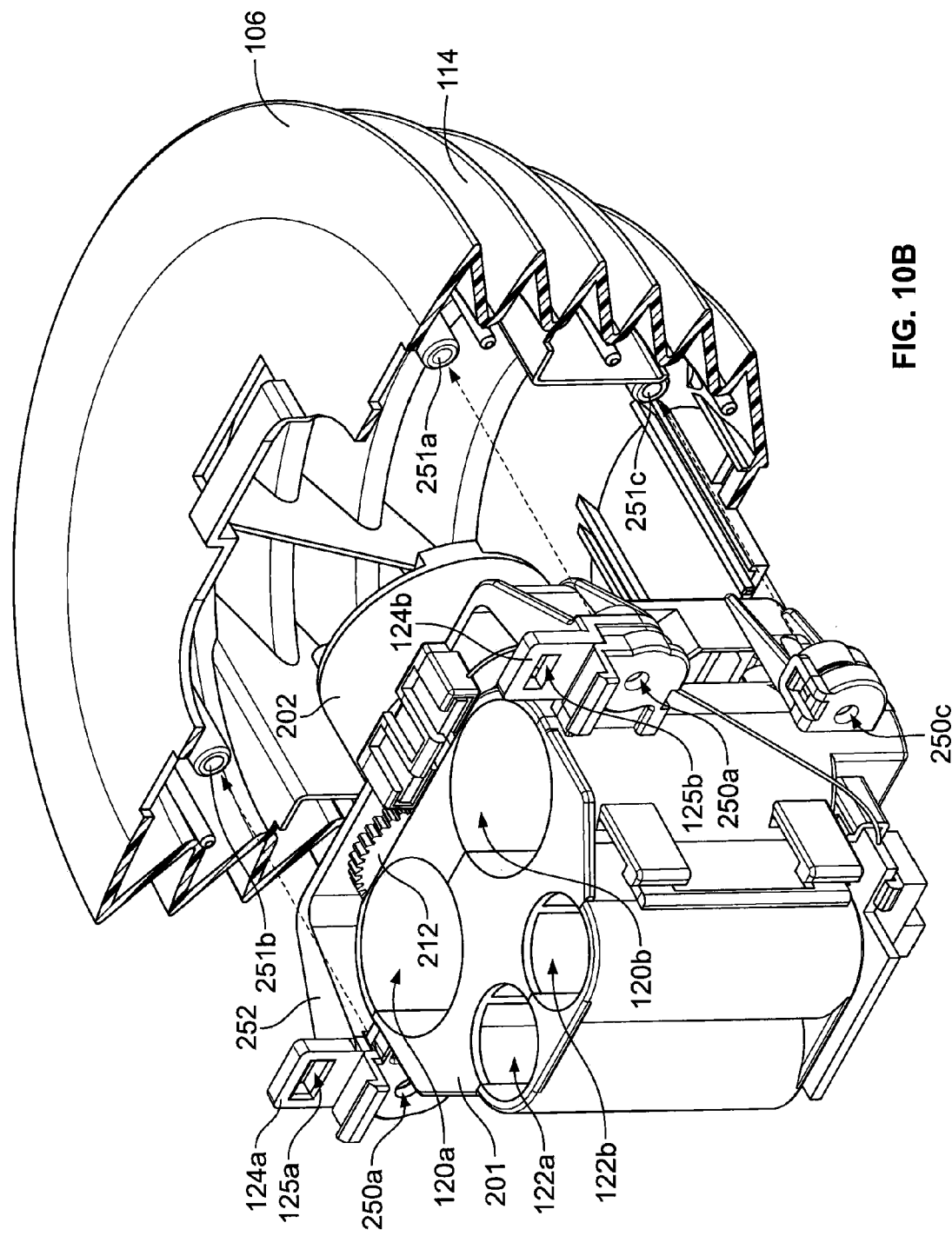
FIG. 10B depicts an exploded isometric view of the device of FIG. 10A being placed into a lower sidewall of the bottom section.

FIGS. 10A and 10B illustrate the installation of the actuator drive system 200 and the housing 201 into the bottom section 106 of the housing 102. Referring to FIG. 10A, a gear plate 252 is mounted over the gears of the actuator drive system 200. Axles for each of the gears of the drive train of the actuator drive system 200 are connected to the gear plate 252, thereby allowing for each gear to be mounted to its respective axle. As shown in FIG. 10A, the gear plate 252 includes mounting apertures that, when the gear plate is in position, overlap with the connection apertures 250*a* (not shown), 250*b*, 250*c* (not shown), and 250*d*. The gear plate 252 also includes a motor mount 254 to which the motor 202 is connected using an appropriate securing mechanism such as screws, clips, adhesives, or other mechanical structures or devices configured to fix the motor 202 to the gear plate 252. The motor mount 254 includes a circular aperture 255 through which a drive shaft of the motor 202 can be positioned and connected to the drive gear 204 for operating the actuator drive system 200, as described above.

Referring to FIG. 10B, the combination of the gear plate 252 (with attached gear train and motor) and the housing 201 are installed into a lower sidewall 256 of the bottom section 106. As illustrated in FIG. 10B, during installation, the motor 202 of the drive system 200 is oriented toward the interior volume of the bottom section 106, while the housing 201 containing the apertures 120*a*, 120*b* and 122*a*, 122*b* is oriented outward. The bottom section 106 includes attachment points 251*a*, 251*b*, 251*c*, 251*d*. Connection apertures 250*a*, 250*b*, 250*c*, 250*d* (not shown) are positioned over attachment points 251*a*, 251*b*, 251*c*, 251*d* (not shown) and a connector, such as a screw, bolt, or clip (though other connection systems such as adhesives may be used) is passed through connection apertures 250*a*, 250*b*, 250*c*, 250*d* and fixed to the attachment points 251*a*, 251*b*, 251*c*, 251*d* of the bottom section 106.

In one embodiment, the bottom section 106 is constructed from two half sections, i.e., two lower sidewalls 256. After the installation of the actuator drive system 200 and the housing 201 into the first half of the bottom section 106, a second half of the bottom section 106 is connected to the first half and positioned around the actuator drive system 200 and the housing 201 to enclose the aforementioned structure within the bottom section 106.

During operation of the dispenser 100, a power source is connected to the motor 202 and is activated by a controller (see, for example, controller 600 of FIG. 46E), which in turn implements an operational methodology responsive to one of a timer, one or more sensors, manual input by way of an instant action button, or any combination thereof. Depending upon the current mode of operation, a determination is made by the controller of the dispenser 100 to initiate a dispensing operation depending upon the input values from the sensor, timer, or manual input systems. The dispensing operation calls for one of the armatures 228, 230 of the actuator drive system 200 to be raised, thereby causing product to be dispensed from the corresponding container 150*a*, 150*b*.

Figure 11:
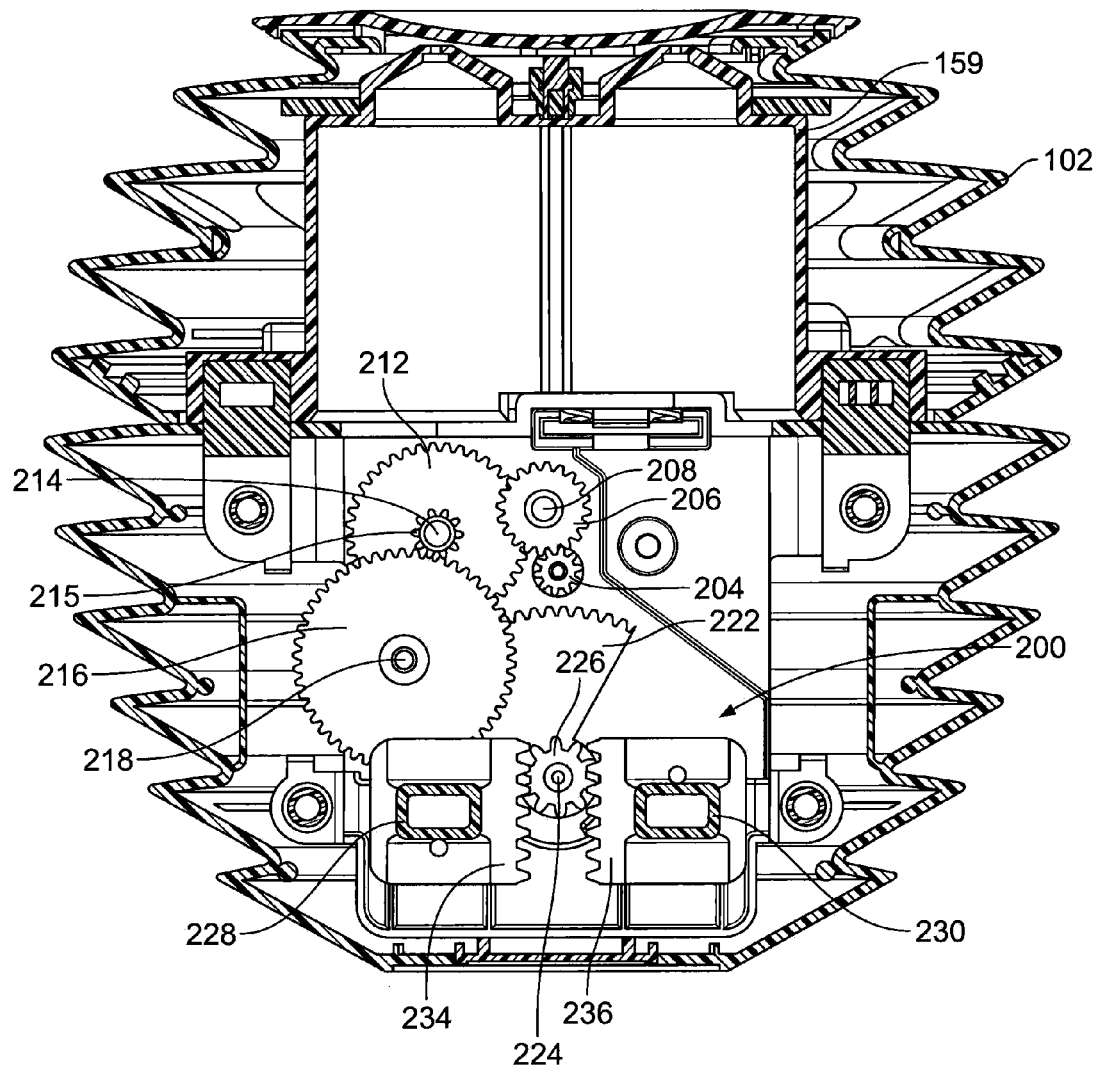
FIG. 11 is a cross sectional view of a dispenser with an actuator drive system in a neutral position.
Figure 12:
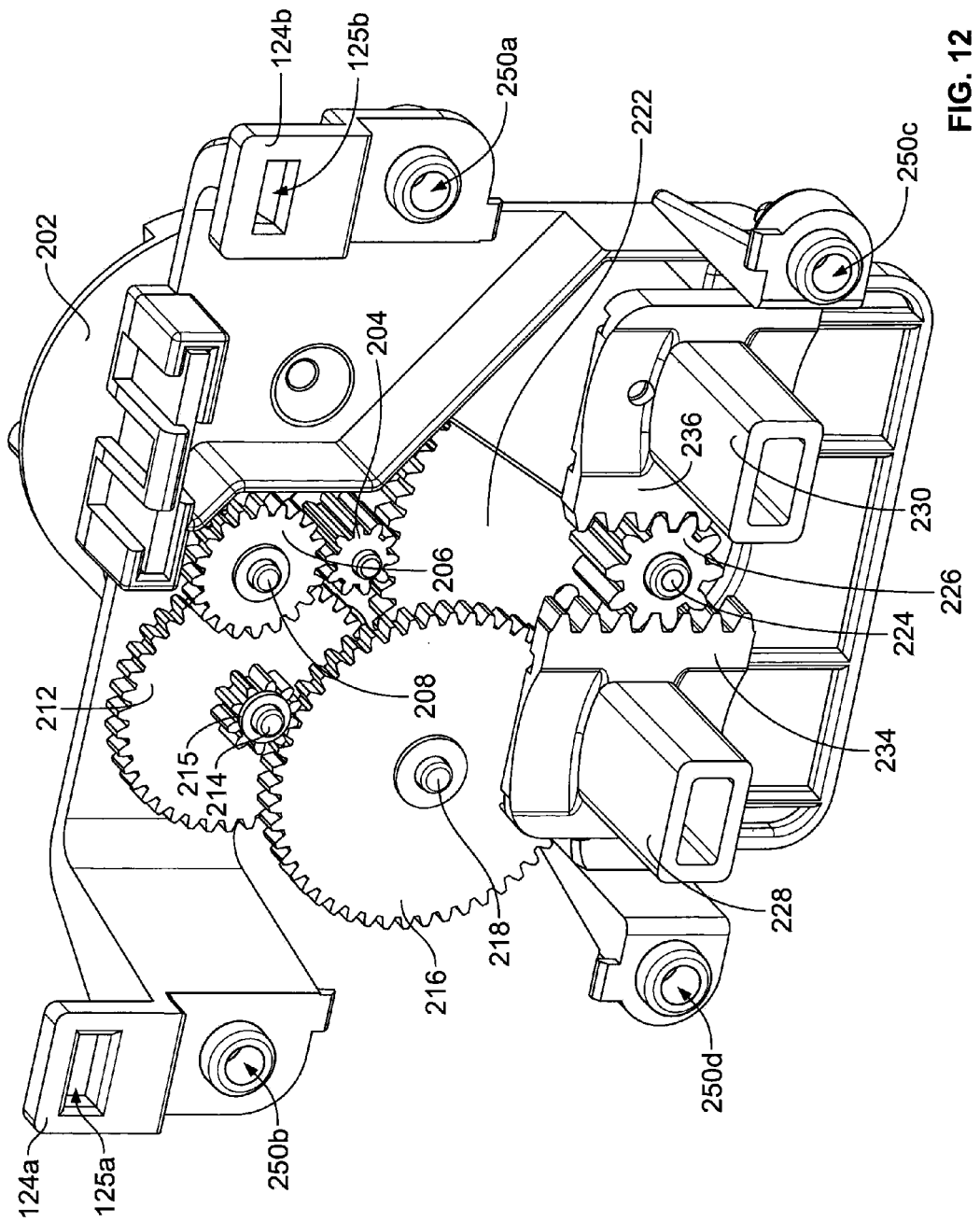
FIG. 12 is an isometric view of the components of the actuator drive system in a neutral position.
Figure 13:
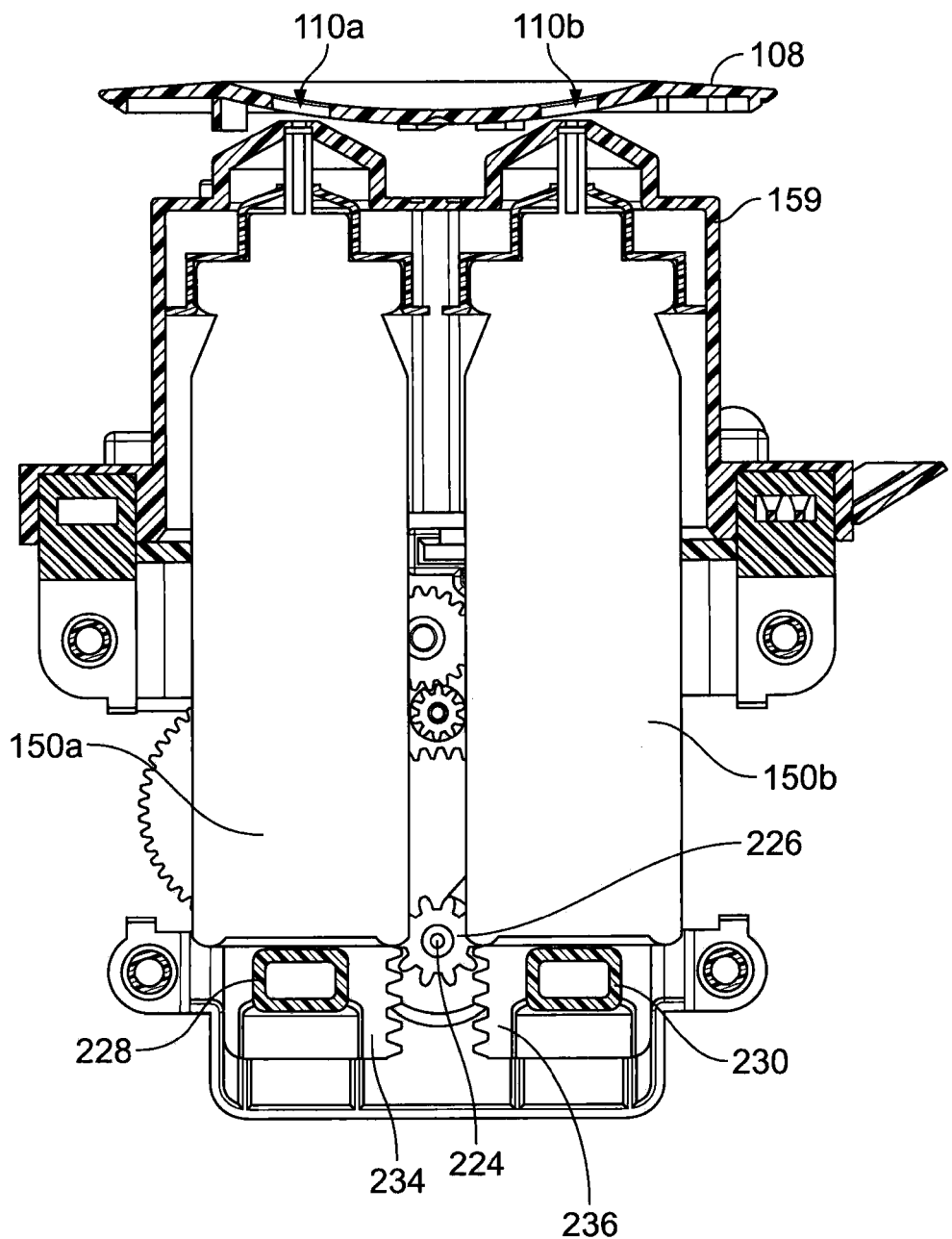
FIG. 13 is a cross sectional view of a dispenser with an actuator drive system and accompanying containers in a neutral position.

When product is not being dispensed from either of the containers 150*a*, 150*b*, the actuator drive system 200 generally resides in a neutral position. In the neutral position, both armatures 228 and 230 are held in the same position with the containers 150*a*, 150*b* being withdrawn from the nozzles 180*a*, 180*b* of the cap assembly 159 or otherwise positioned to prevent dispersal of product from either of the containers 150*a*, 150*b*. FIGS. 11-13 illustrate the actuator drive system 200 in a neutral position. FIG. 11 is a cross-sectional view of the dispenser 100 taken generally along the vertical plane that passes through the center of each of the apertures 120*a*, 120*b* and 160*a*, 160*b* (see, for example, plane 9-9 of FIG. 8) showing the actuator drive system 200 in a neutral position. Further, in FIG. 11 portions defining the apertures 120*a*, 120*b* have been removed to expose the working components of the actuator drive system 200. FIG. 12 is an isometric view of the components of the actuator drive system 200 positioned in a neutral position. FIG. 13 is a cross-sectional view of the dispenser 100 taken generally along the vertical plane that passes through the center of each of the apertures 120*a*, 120*b* and 160*a*, 160*b* (see, for example, plane 9-9 of FIG. 8) showing the actuator drive system 200 in a neutral position as well as the respective positions of the containers 150*a*, 150*b* in their neutral positions.

As shown in FIGS. 11-13, in the neutral position, both of the armatures 228 and 230 are positioned at the same level or height within their respective apertures 120*a*, 120*b*. In one embodiment, when the armatures 228, 230 are in the neutral position, both of the armatures 228, 230 are in-line with a seat 232 (shown in FIG. 9) of each aperture 120*a*, 120*b* although other neutral positions may be established for the armatures 228 and 230.

Figure 14:
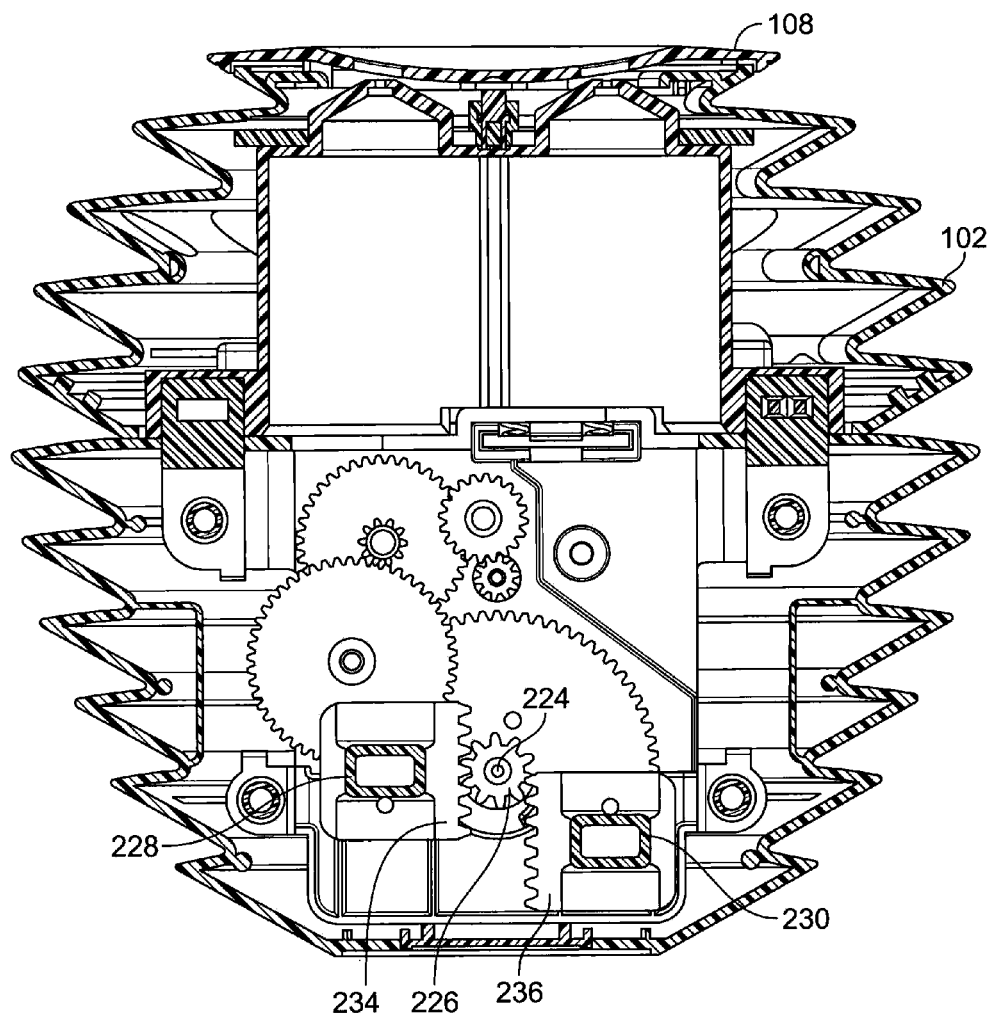
FIG. 14 is a cross sectional view of a dispenser with an actuator drive system in a first active position.
Figure 15:
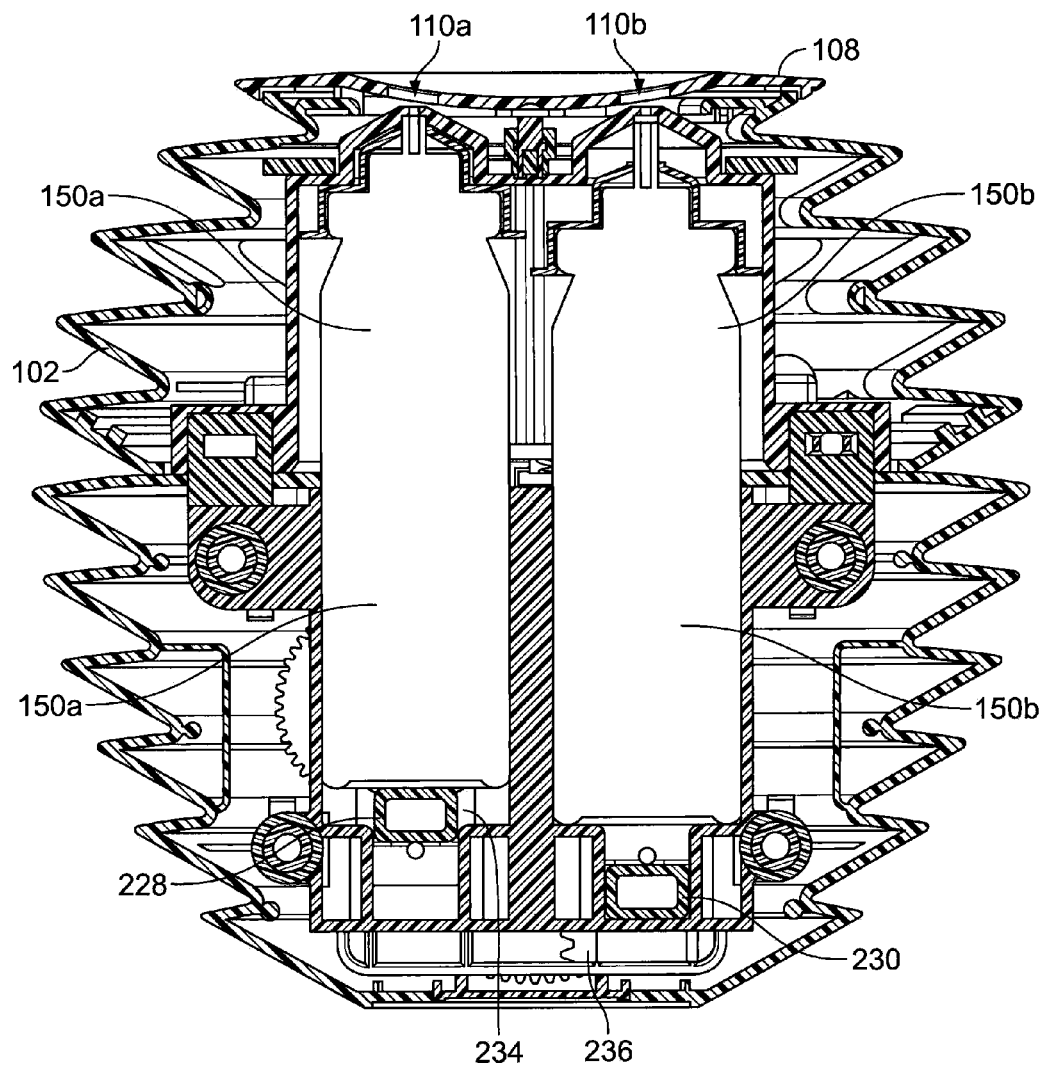
FIG. 15 is a cross sectional view of a dispenser with an actuator drive system and a container in a first active position.

Upon a determination by the controller of the motor 202 that product is to be dispensed from the container 150*a*, for example, the container 150*a* is raised by the armature 228 toward the cap assembly 159 and into a first active position, thereby causing product to be dispensed from the container 150*a*. As a further example, FIGS. 14 and 15 are illustrations of the actuator drive system 200 positioned in a manner to cause product to be dispersed from the container 150*a*. FIG. 14 is a cross-sectional view of the dispenser 100, with portions defining the apertures 120*a*, 120*b* removed for purposes of clarity, taken generally along the vertical plane that passes through the center of each of the apertures 120a, 120b and 160a, 160b showing the actuator drive system 200 (see, for example, plane 9-9 of FIG. 8) in a position to cause product to be dispensed from container 150a. Further, FIG. 15 is a similar cross-sectional view of the dispenser 100, which shows the drive system 200 in a position to cause product to be dispensed from the container 150a and the respective positions of the containers 150a, 150b.

To dispense product from the container 150a, the controller causes the motor 202 to rotate the drive gear 204 in a counter-clockwise direction (from the point of view of the motor 202). This rotation of the drive gear 204 causes the gear 226, which is connected to the gear 222, to also rotate in a counter-clockwise direction. Because the teeth of the gear 226 are engaged with the rack 234 (of armature 228) and the rack 236 (of armature 230), the counter-clockwise rotation of the gear 226 causes the armature 228 to move upwards, while the armature 230 moves downwards. As depicted in FIG. 15, the upward movement of the armature 228 raises the container 150a to dispense product therefrom by bringing the valve stem 155a of the container 150a into contact with the nozzle 180a of the cap assembly 159 (see FIG. 6). Conversely, as the armature 228 moves upwards, the armature 230 is lowered. As the armature 230 is lowered below the height of the seat 232, the container 150b rests upon the seat 232 within the aperture 120b. In other embodiments, the seats may be removed so that no lower boundary for container movement is provided. Consequently, in this embodiment each container will ride upon the top surface of the container's respective armature throughout the armature's entire stroke. After sufficient product is dispensed from the container 150a, the motor 202 causes the gear 226 to rotate in a clockwise direction to lower the armature 228. Lowering the container 150a may cause same to be unseated from within the nozzle 180a or for the sufficient removal of pressure to cause the valve stem 155a to remain fully or partially seated within the nozzle 180a but not in an actuated position. The motor 202 continues to rotate the gear 226 in a clockwise direction until both armatures 228 and 230 are returned to their respective neutral positions (as illustrated in FIGS. 11-13).

Figure 16:
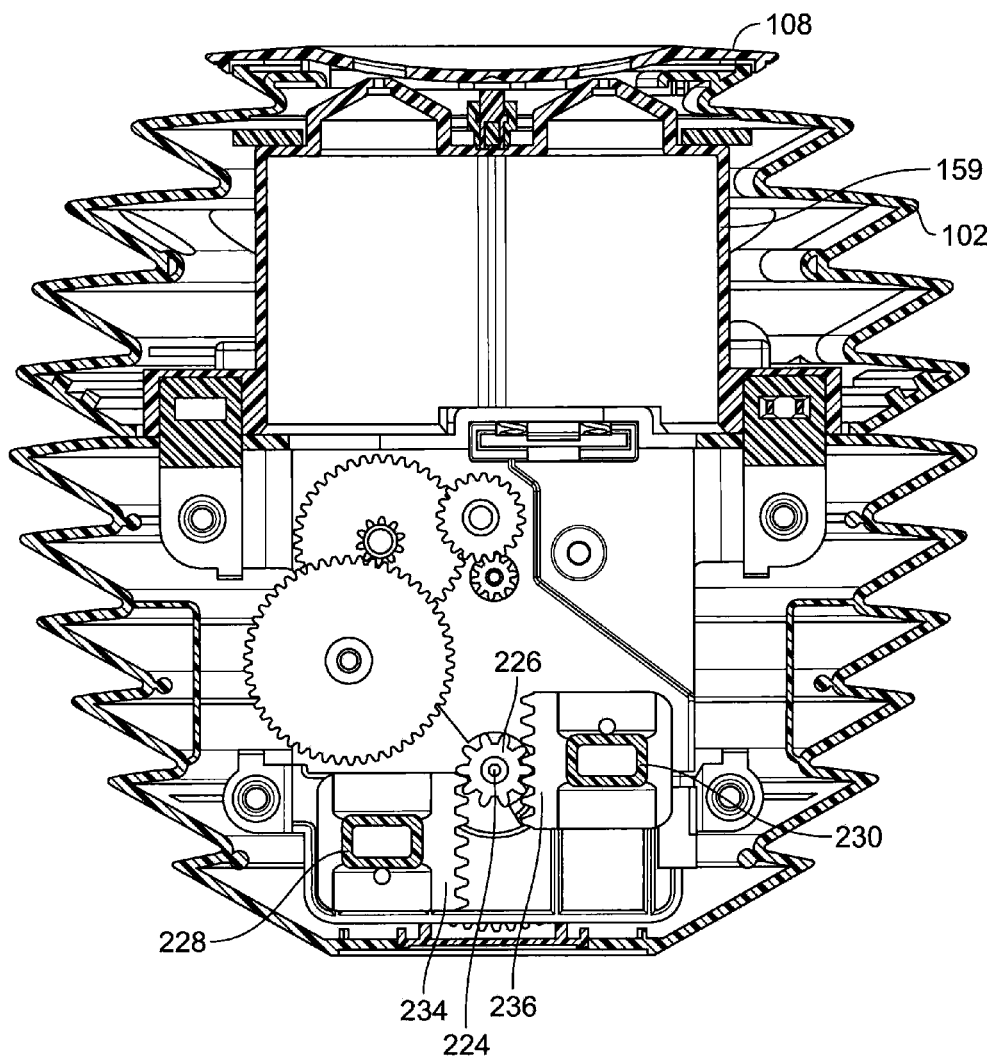
FIG. 16 is a cross sectional view of a dispenser with an actuator drive system in a second active position.
Figure 17:
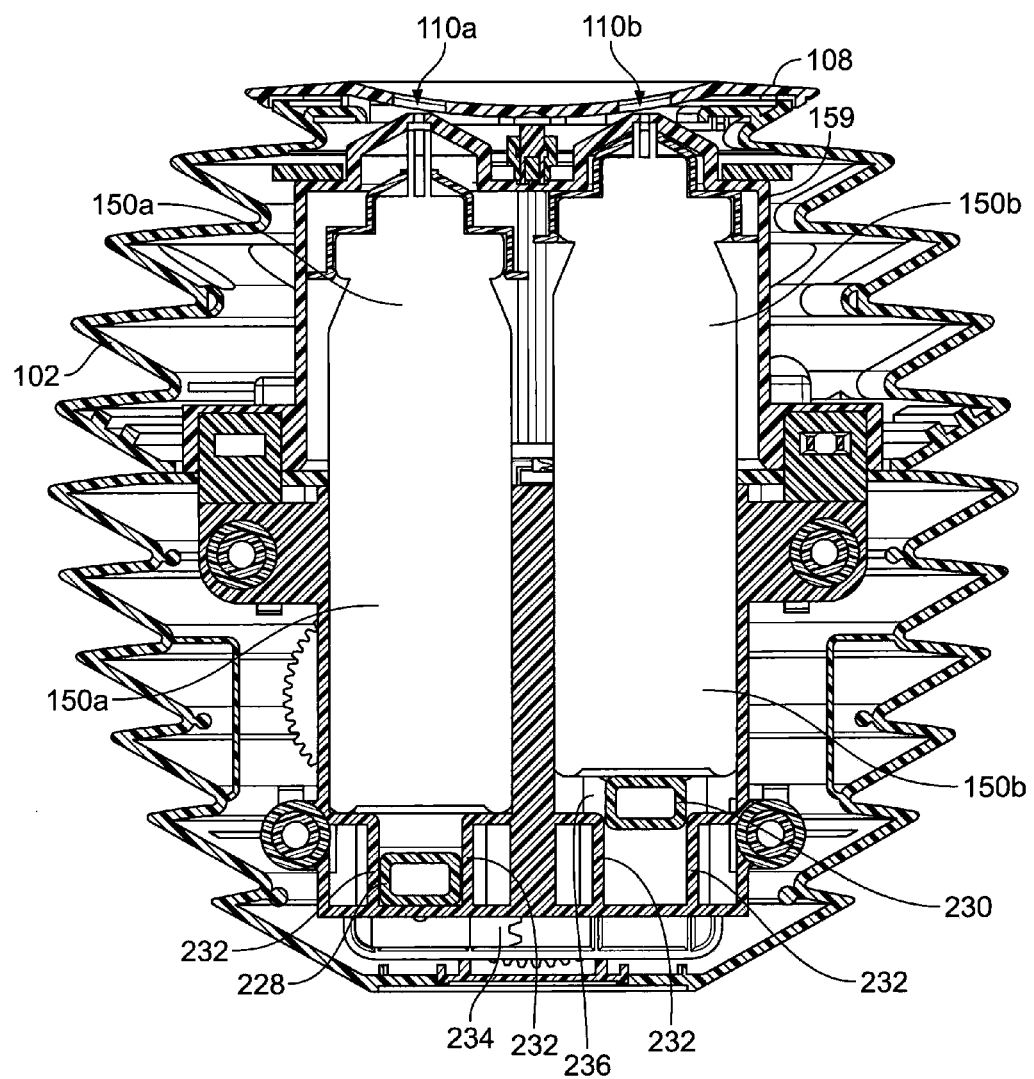
FIG. 17 is a cross sectional view of a dispenser with an actuator drive system and a container in a second active position.

Alternatively, product can be dispensed from the container 150b. To dispense product from the container 150b, the container 150b is raised by the armature 230 toward the cap assembly 168, thereby causing product to be dispensed. FIGS. 16 and 17 illustrate the actuator drive system 200 positioned in a manner to cause product to be dispersed from container 150b. FIG. 16 is a cross-sectional view of the dispenser 100, with portions defining the apertures 120a, 120b removed for purposes of clarity, taken generally along the vertical plane that passes through the center of each of the apertures 120a, 120b and 160a, 160b (see, for example, plane 9-9 of FIG. 8), which shows the actuator drive system 200 in a position to cause product to be dispensed from the container 150b. Further, FIG. 17 is a similar cross-sectional view of the dispenser 100, which shows the actuator drive system 200 in a position causing product to be dispensed from container 150b and the respective positions of the containers 150a and 150b.

To dispense product from the container 150b the controller causes the motor 202 to rotate the drive gear 204 in a clockwise direction (from the point of view of the motor 202). This rotation of the drive gear 204 causes the gear 226, which is connected to the gear 222 to also rotate in a clockwise direction. As the teeth of the gear 226 are engaged with the racks 234 and 236, the clockwise rotation of the gear 226 causes the armature 228 to move downwards, while the armature 230 moves upwards. As depicted in FIG. 17, the upward movement of the armature 230 raises the container 150b to dispense product therefrom by bringing the valve stem 155b of the container 150b into contact with the nozzle 180b of the cap assembly 159 (see FIG. 6). Conversely, as the armature 230 moves upwards, the armature 228 is lowered. As the armature 228 is lowered, the container 150a rests upon the seat 232 within the aperture 120a. In other embodiments, the seats may be removed so that no lower boundary for container movement is provided. Consequently, in this embodiment each container will ride upon the top surface of its respective armature throughout the armature's entire stroke. After sufficient product is dispensed from the container 150b, the motor 202 causes the gear 226 to rotate in a counter-clockwise direction to lower the armature 230. Lowering the container 150b may cause same to be unseated from within the nozzle 180b or for the sufficient removal of pressure to cause the valve stem 155b to remain fully or partially seated within the nozzle 180b but not in an actuated position. The motor 202 continues to rotate the gear 226 in a counter-clockwise direction until both the armatures 228 and 230 are returned to their respective neutral positions (as illustrated in FIGS. 11-13).

Movement of the armatures 228, 230 may occur in several different manners. For example, in one embodiment the motor 202 drives the armatures 228, 230 for a predetermined distance. Once driven for the predetermined distance, the motor 202 is disabled. In that mode of operation, a container may be raised toward the cap assembly 159 in order to dispense product therefrom. After sufficient product is dispensed and/or a metered dose is expelled, the motor 202 is disabled, and a spring assembly positioned within the cap assembly 159 and/or the spring within the valve assembly of the container itself, provides a sufficient force to push the container downwardly to close the valve assembly of the container and stop any dispensing of product from a non-metered container and/or to reposition the armatures 228, 230 and the gears of actuator drive system 200 to their respective neutral positions.

In some embodiments, a spring assembly (not shown) is positioned within cap assembly 159 above each container 150a, 150b to assist in moving the containers downwardly to stop a spraying sequence and/or after completion of a spraying sequence. In that case, the spring assembly is configured to contact a top surface of the containers 150a, 150b as the container is moved upwardly toward cap assembly 159. As the container 150a, 150b moves upwardly, the spring assembly is compressed and presses against the container 150a, 150b. After sufficient product has been discharged, the spring assembly can provide downward force to assist in moving the container 150a, 150b away from the nozzle 180a, 180b to stop the dispensing of product and/or to cause the valve stem 155a, 155b to be fully or partially unseated in a manner that prevents continued spraying or allows the valve assembly to close. In such an embodiment, the actuator drive system 200 is configured to drive each container 150a, 150b upwardly with sufficient force to overcome the resistance added by the downward force of the spring assembly.

Alternatively, after sufficient product has been dispensed from an active container 150a, 150b, the armature 228, 230 that raised the container is actively driven downwardly by the motor 202. This downward movement of the container 150a, 150b and the armature 228, 230 may be achieved solely by forces contributed by the motor 202, or may be achieved by a combination of force provided by the motor 202 as well as a force contributed by a spring assembly mounted within the cap assembly 159 and/or a spring within the valve assembly of the container 150a, 150b.

Additionally, it is contemplated that the armatures 228, 230 may be driven for a predetermined period of time, whereby one of the armatures 228, 230 is raised to cause the valve stem 155a, 155b for a particular container 150a, 150b to be depressed for an extended period of time. Thereafter, the container is placed into a non-actuated position by one or more of the motor 202, a spring assembly disposed within the cap assembly 159, or a spring within the valve assembly of the container 150a, 150b, as described above. In this embodiment, the armature 228, 230 may be prevented from upward travel for a period of time as the valve stem 155a, 155b may be in a fully depressed condition, which prevents further upward movement of the container 150a, 150b but allows for an extended period of dispensing.

In other embodiments of the dispenser 100, different actuator drive systems may be utilized to cause product to be dispensed from at least one of the containers 150a and 150b. For example, if the containers 150 include either tilt-activated or vertically-activated valve stems, the actuator system may comprise an electro-mechanical unit, such as a solenoid assembly configured to drive a plunger that engages a flange formed around a discharge end of the tilt-activated valve stem. When the solenoid is energized, the plunger presses against the flange causing product to be dispensed through the valve stem. A representative solenoid assembly, for example, is a Ledex® Low Profile Battery Operated Linear Solenoid, size number 1 ECM, model number 282342-025, which is available from Johnson Electric, Industry Products Group, Vandalia, Ohio. The 1 ECM-282342-025 solenoid weighs 42.5 grams, is 25.4 mm in diameter and 13.5 mm tall. When operating on a 50% maximum duty cycle, the 1 ECM-282342-025 solenoid nominally requires 2.9 volts DC, generates 2.2 Newtons (0.49 pounds) of force through a nominal stroke of 2 mm, and can remain energized for a maximum of 162 seconds. Alternatively, other electro-mechanical units or devices can be used to depress or tilt the valve stems of containers. Such units include bi-metallic actuators, piezo-linear motors, or an electro-responsive wire that is adapted to actuate a vertical or tilt-activated valve stem.

Figure 18:
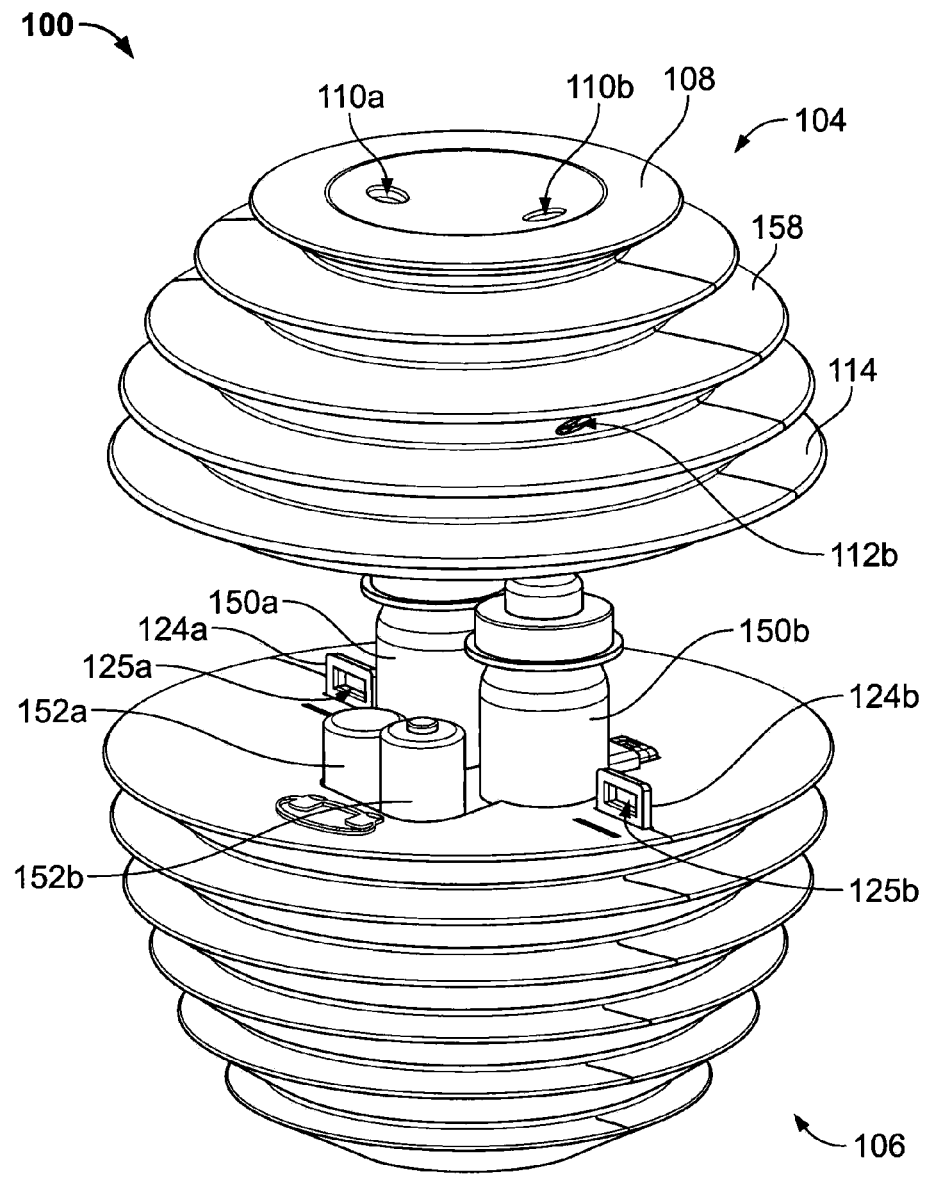
FIG. 18 is an exploded isometric view of a top and bottom section of the housing of FIG. 1.

As previously described above, the top section 104 and the bottom section 106 of the housing 102 are connected to one another to place the dispenser 100 into an operable state. Turning to FIG. 18, an exploded isometric view of the dispenser 100 depicts the top section 104 of the housing 102 positioned over the bottom section 106. The bottom section 106 includes installed aerosol containers 150a, 150b and batteries 152a, 152b disposed within the apertures 120a, 120b and 122a, 122b, respectively. In a typical scenario, a user may have recently replaced one or both of the aerosol containers 150a, 150b to replace one or more empty containers and/or to substitute one or more containers containing one product for another container containing a different product. After the containers 150a, 150b and batteries 152a, 152b are seated within their respective apertures, the top section 104 is placed on the bottom section 106 and the two sections locked together. After the sections are locked together, the dispenser 100 can operate as described herein. Not only does this secure both the containers 150a, 150b and the batteries 152a, 152b within the housing 102, it places the various components contained within each section of the housing 102 in electrical communication with one another. Accordingly, after the top section 104 and the bottom section 106 are secured to one another, electrical energy from the batteries 152a, 152b can be supplied to various electronic components of the dispenser 100, and the controller contained within the top section 104 can be placed into communication with the actuator drive system 200 and selector switch disposed within, or mounted to, the bottom section 106.

Figure 19:
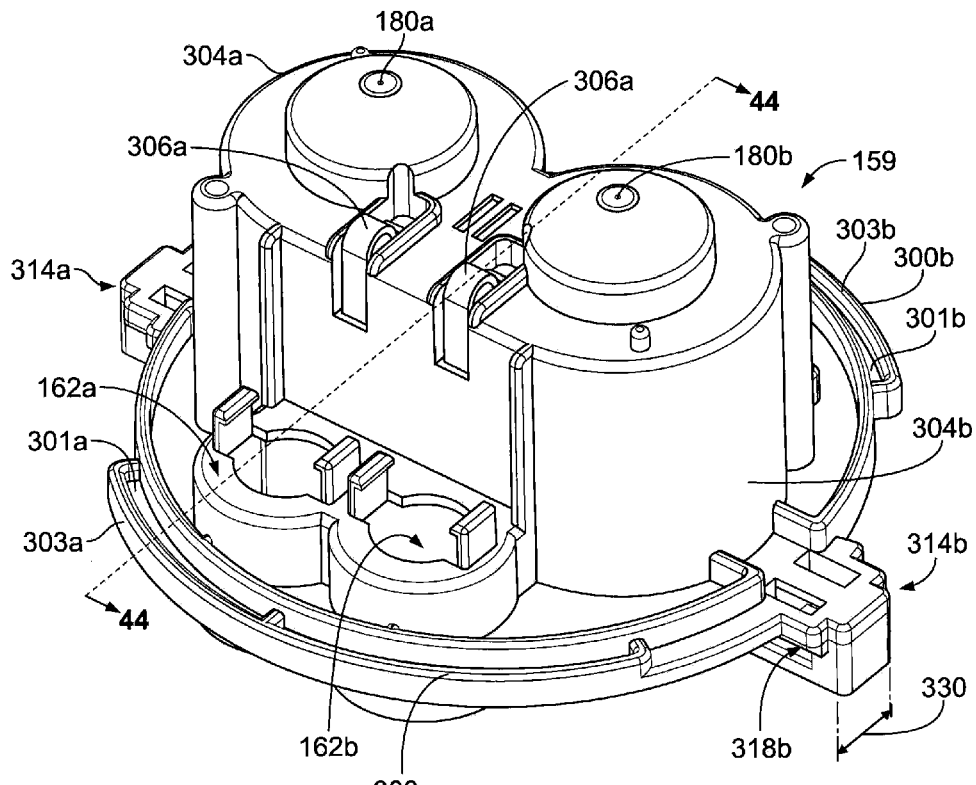
FIG. 19 is an isometric view of a cap assembly.

To unite the top section 104 with the bottom section 106, a user first holds the top section 104 above the bottom section 106. As previously noted, the top section 104 includes the cap assembly 159, which must be appropriately aligned with the containers 150a, 150b and the batteries 152a, 152b prior to uniting the two sections. Turning to FIG. 19, the cap assembly 159 includes apertures 162a, 162b and comprises housing structures 304a and 304b that generally define the volumes comprising the apertures 160a, 160b. The cap assembly 159 may also incorporate container detection arms 306a and 306b to assist in detecting the presence of a container within cap assembly 159, which will be described in greater detail below.

The cap assembly 159 also includes sliding members 300a and 300b. Sliding members 300a and 300b are fixed structures that project radially away from the cap assembly 159. As shown in FIG. 19, the sliding members 300a and 300b comprise horizontal members 301a and 301b. Vertical walls 303a and 303b are coupled to horizontal members 301a and 301b and run along a perimeter thereof. The sliding members 300a and 300b are formed along separate lengths of the perimeter of the cap assembly 159 on opposing sides thereof.

Figure 20:
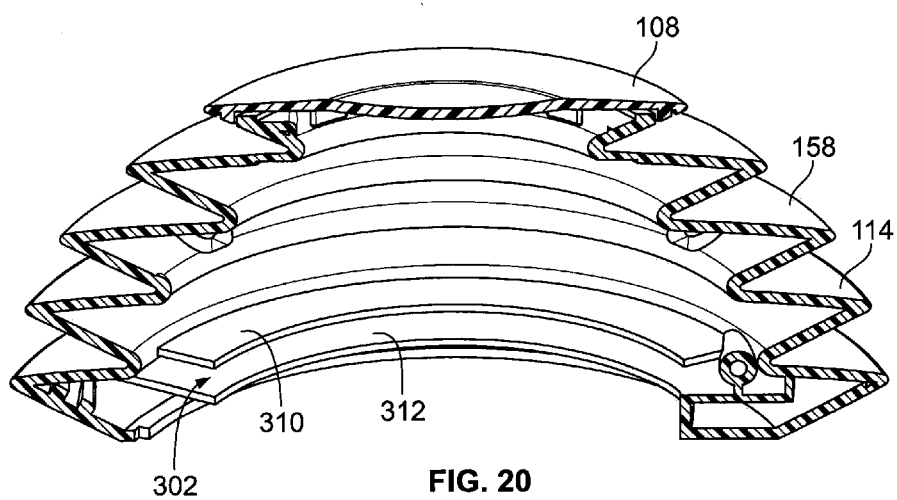
FIG. 20 depicts a portion of an upper sidewall of the top section of the housing of FIG. 1.

The sliding members 300a and 300b are each configured to engage with one of two grooves formed within an interior portion of the upper sidewall 158 of the top section 104. FIG. 20 is a cross-sectional view of an interior surface of the upper sidewall 158 depicting a groove 302. The groove 302 is defined by walls 310 and 312. The walls 310 and 312 project horizontally away from an interior surface of the sidewall 158 and are spaced so that groove 302 can receive either of sliding members 300a, 300b. When disposed within the groove 302, either sliding member 300a or 300b can rotatably slide therein. A second groove 302 is formed along the interior surface of the opposite side of the upper sidewall 158 from that depicted in FIG. 20 and is configured with a corresponding geometry to similarly receive the other of the sliding member 300a, 300b (see FIG. 21). When the cap assembly 159 is positioned within the joined portions of the top section 104, the sliding members 300a and 300b are provided within the grooves 302 and allow the cap assembly 159 and the sidewall 158 to rotatably slide with respect to one another.

With reference to FIGS. 18 and 19, placement of the top section 104 on the bottom section 106 causes stop structures 314a, 314b on the cap assembly 159 to be positioned over and around the locking tabs 124a, 124b located on the bottom section 106, thereby preventing rotation of the cap assembly 159 with respect to the bottom section 106. The stop structures 314a, 314b include apertures formed in the bottom surface of the stop structures (the apertures are visible in FIG. 4 as elements 316a, 316b) sized to receive the locking tabs 124a, 124b. Accordingly, when the top section 104 is connected to the bottom section 106, the locking tabs 124a, 124b of the bottom section 106 reside within the stop structures 314a, 314b of the cap assembly 159. The stop structures 314a, 314b also include horizontal apertures 318a, 318b formed therethrough. The apertures 318a, 318b define a rectangular opening that has approximately the same dimensions as those of the rectangular apertures 125 defined by the locking tabs 124a, 124b. In other implementations, though, the geometry of the apertures 318a, 318b, 124a, and 124b may be modified to adopt shapes different than that of the rectangular openings of the present implementation.

Figure 21A:
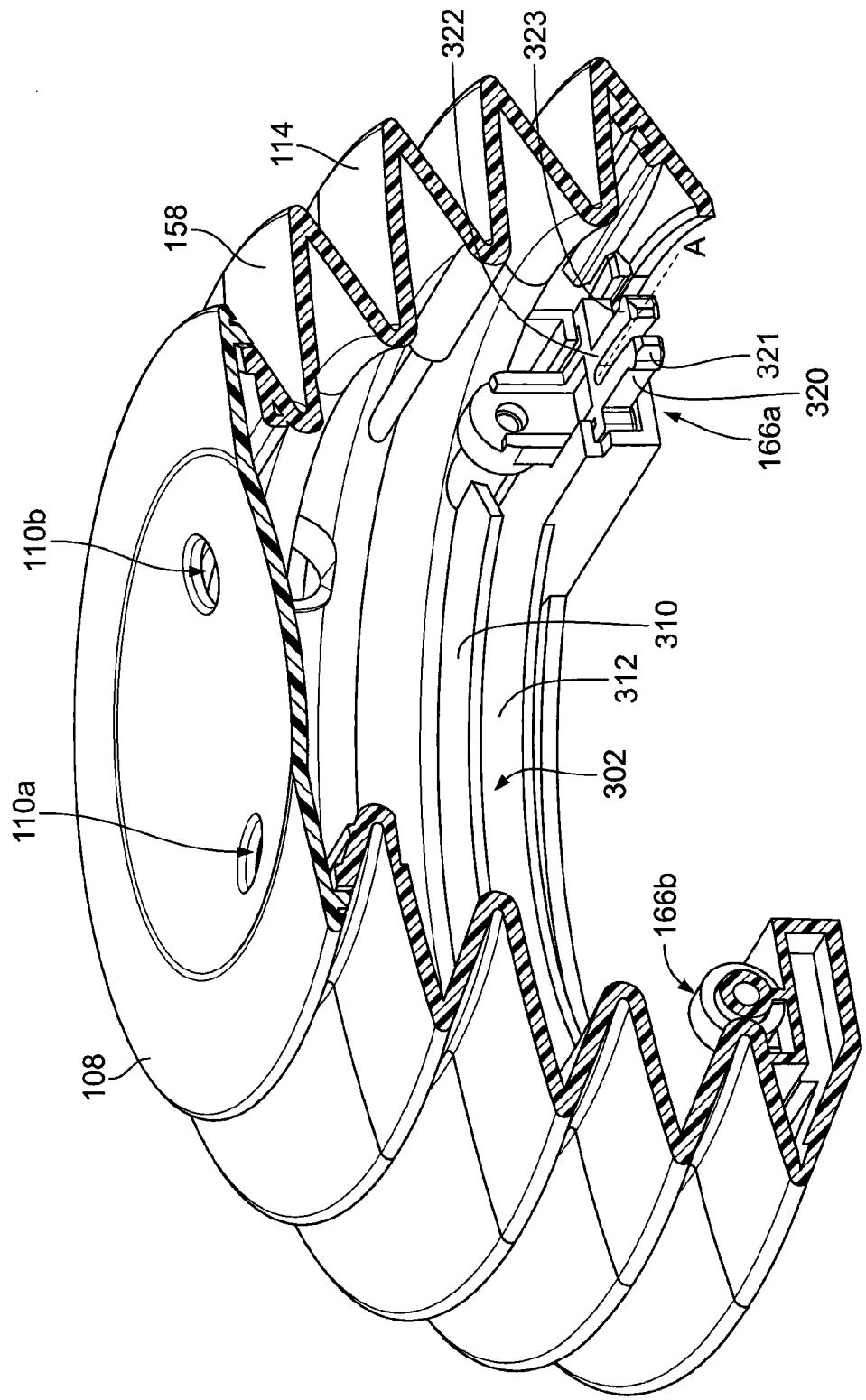
FIG. 21A is a partial sectional, isometric view of a top section of the housing of FIG. 1 including a locking member.
Figure 21B:
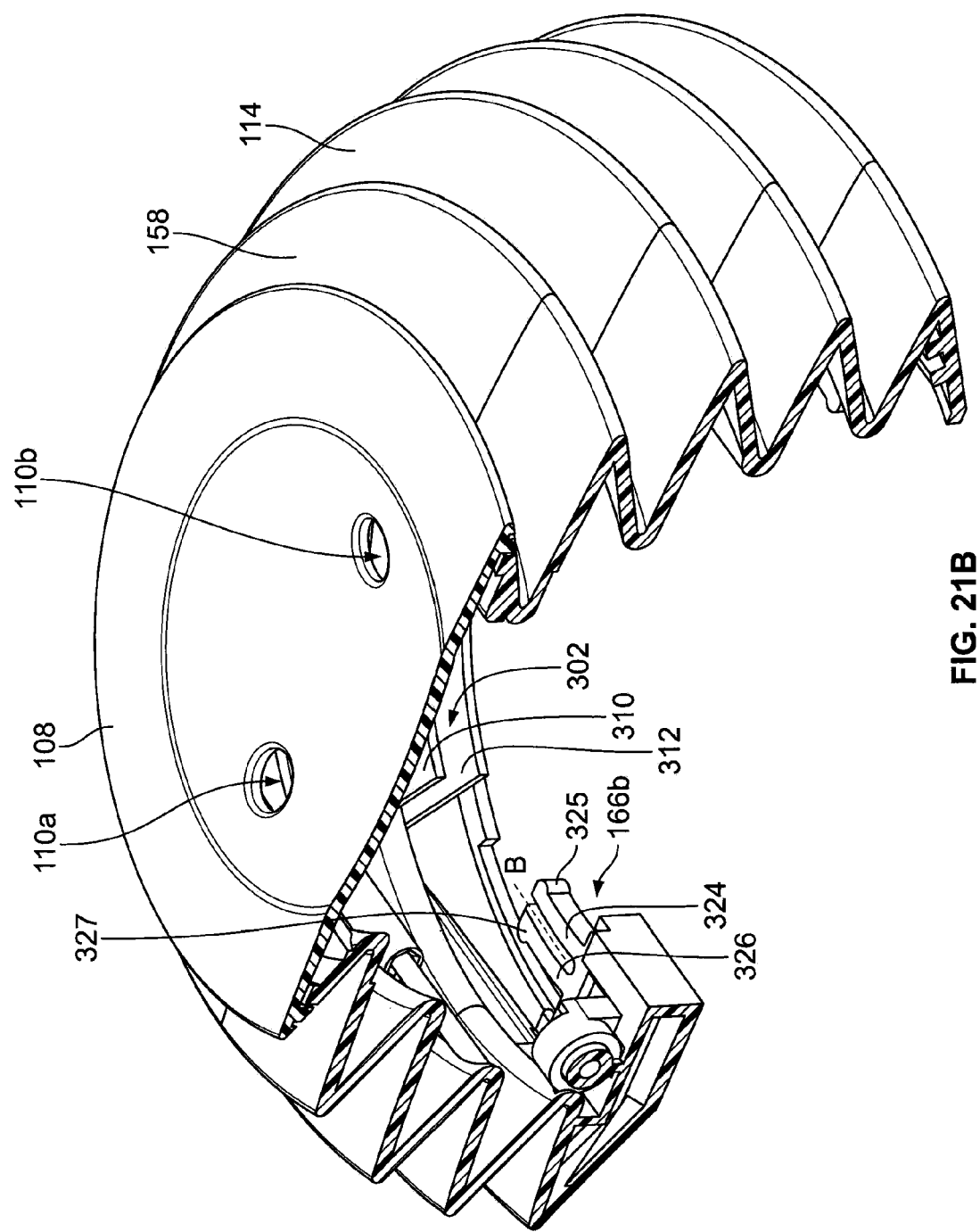
FIG. 21B is a different partial sectional, isometric view of the top section of FIG. 21A.

Turning to FIGS. 21A and 21B, the interior surface of the upper sidewall 158 of the top section 104 is shown, which includes the locking members 166a and 166b connected thereto. FIG. 21A shows the interior portion of the upper sidewall 158 that includes the locking member 166a and FIG. 21B similarly shows the locking member 166b. Either of the locking members 166a, 166b may be integrally formed with the sidewall. Alternatively, the locking members 166a, 166b may comprise separate structures that are affixed to the sidewall, for example, by an adhesive, an interference fit, a fixture such as a screw or bolt, or any combination thereof.

As shown in FIG. 21A, the locking member 166a comprises two locking prongs 320 and 322. The locking prongs 320 and 322 each have bulbous tips that project laterally away from an axis "A" defined by the length of the locking member 166a. The tips of both prongs 320 and 322 include curved outer surfaces 321 and 323. The locking member 166a is configured to couple with the locking tab 124a on the bottom section 106 as well as the stop structure 314a of the cap assembly 159. As such, the prongs 320 and 322 of the locking member 166a are sized so that as the locking member 166a is introduced to the apertures 318 and 125 within the stop structure 314a and the locking tab 124a, the curved surfaces 321 and 323 of the locking member 166a contact inner surfaces defining walls of the apertures 318, 125. As the locking member 166a is pushed through the apertures 318, 125, both of the prongs 320 and 322 deform inwardly as surfaces 321 and 323 slide along the inner surfaces of the walls defining the apertures 318, 125. Eventually, the bulbous tip of each of the prongs 320 and 322 passes through the apertures 318, 125 of the stop structure 314a and the locking tab 124a. At that point, each of the prongs 320 and 322 can move away from each other so that the outer surfaces of the arms of the prongs 320 and 322 contact surfaces of the stop structure 314 and the locking tab 124. The locking member 166a is therefore lockingly engaged with the locking tab 124a as well as the stop structure 314a and the bulbous tips of each of the prongs 320 and 322 operate as barbs to prevent the locking member 166a from being easily withdrawn from the stop structure 314a and the locking tab 124a. In this arrangement the length of the arms of both the prongs 320 and 322 (that is, not including the tips of prongs 320 and 322) is greater than the width of the stop structure 314a (indicated by element 330 shown on FIG. 19) to ensure that both of the prongs 320 and 322 can extend all the way through the stop structure 314a.

To separate the locking member 166a from the locking tab 124a and the stop structure 314a, the process is reversed and the locking member 166a is pulled away from the locking tab 124a and stop structure 314a. As the locking member 166a is withdrawn from the locking tab 124a and the stop structure 314a, the bulbous ends of the prongs 320 and 322 contact the vertical walls defining the rectangular apertures 318, 125. As pressure is applied, the prongs 320 and 322 deform and move toward one another, thereby providing room for the bulbous tips of the prongs 320 and 322 to pass though the rectangular apertures 318, 125 and to release the locking member 166a from the locking tab 124a and the stop structure 314a. After the locking member 166a is withdrawn from the locking tab 124a and the stop structure 314a, the prongs 320 and 322 return to the original configuration as illustrated in FIG. 21A.

As shown in FIG. 21B, the locking member 166b operates in a similar manner as described in connection with the locking member 166a. The locking member 166b includes two locking prongs 324 and 326 that include bulbous tips having curved outer surfaces 325 and 327. The locking member 166b is configured to couple with the locking tab 124b on the bottom section 106 as well as the stop structure 314b of the cap assembly 159.

As illustrated in both FIGS. 21A and 21B, the locking members 166a, 166b are both oriented in a clockwise direction when viewed from the top of the upper sidewall. As such, by rotating the sidewall 158 of the top section 104 in the same clockwise direction, the locking members 166a, 166b can be rotationally moved so as to engage the respective locking structure. In an embodiment where the sidewall 158 of the top section 104 is rotated in a counter-clockwise direction to lock the top section 104 and the bottom section 106, the orientation of both the locking members 166a, 166b would be reversed within the sidewall 158 of the top section 104.

Figure 22:
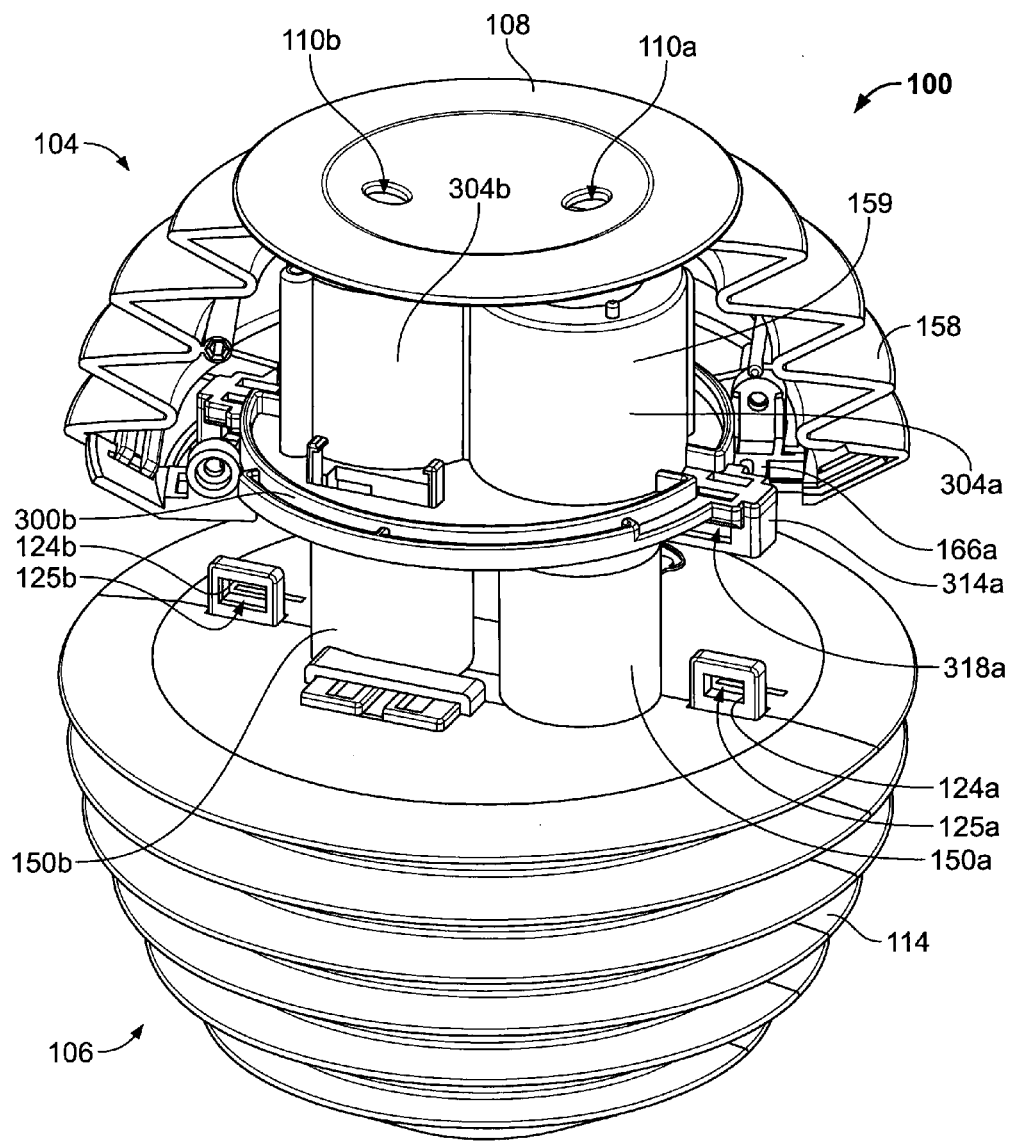
FIG. 22 is an exploded, partial sectional, isometric view of a first step in a sequence to combine a top section of a housing with a bottom section thereof.
Figure 23:
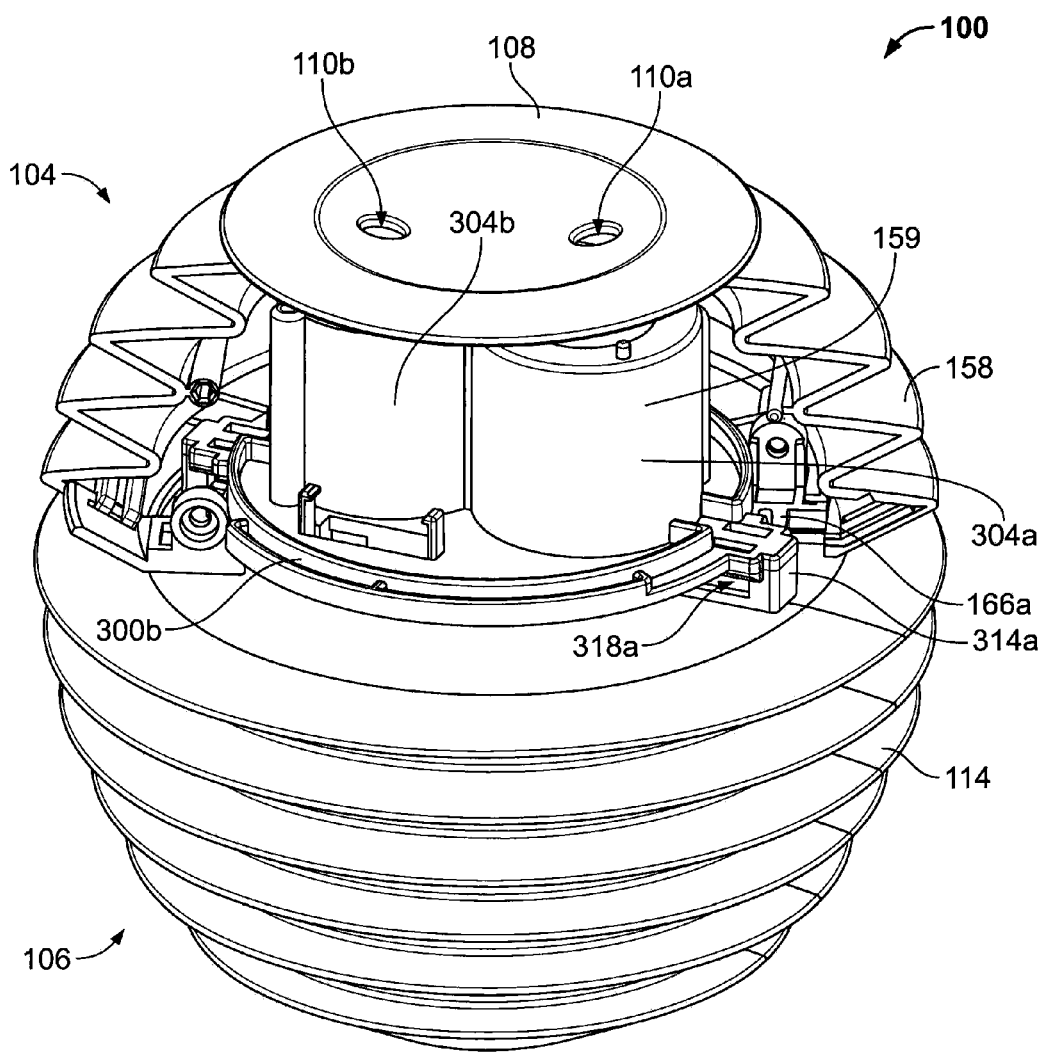
FIG. 23 is a partial sectional, isometric view of a second step in a sequence to combine a top section of a housing with a bottom section thereof.
Figure 24:
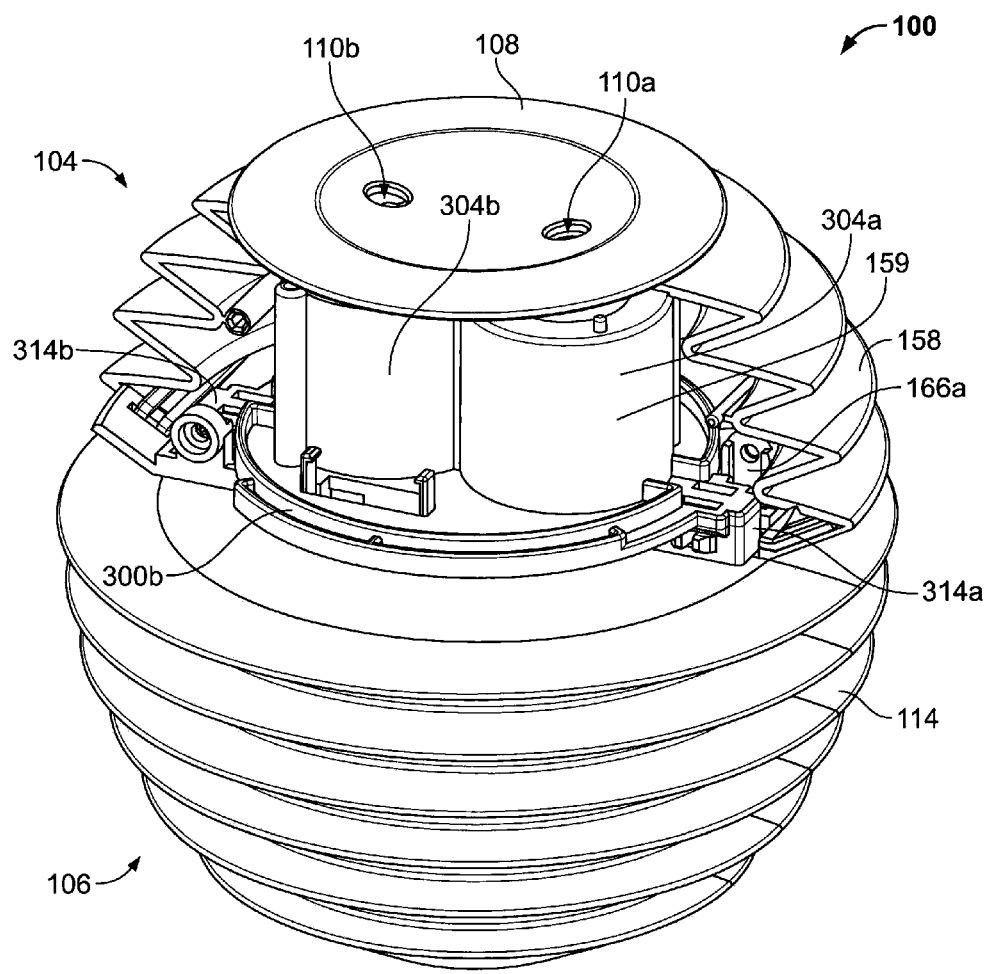
FIG. 24 is a partial sectional, isometric view of a third step in a sequence to combine a top section of a housing with a bottom section thereof.

FIGS. 22-24 illustrate a typical sequence of steps for the connection of the top section 104 to the bottom section 106 of the housing 102. In each of the FIGS. 22-24, a portion of the sidewall of the top section has been removed to expose the cap assembly 168 and the locking members therein.

Referring to FIG. 22, the top section 104 is first positioned over the bottom section 106. The cap assembly 159, which is contained within the sidewall 158 of the top section 104, is aligned with the bottom section 106. The containers 150a, 150b and the batteries 152a, 152b are positioned within the apertures 120a, 120b and 122a, 122b, respectively, of the bottom section 106. Additionally, the stop structures 314a, 314b of the cap assembly 168 are positioned over the locking tabs 124a, 124b of the bottom section 106.

After the cap assembly 159 is aligned correctly, the top section 104 is lowered onto the bottom section 106. While the top section 104 is lowered, the containers 150a, 150b and/or the batteries 152a, 152b disposed within the bottom section 106 may act as guides to assist a user in correctly positioning the cap assembly 168 as it is lowered. Generally, the positioning of the top section 104 over the bottom section 106 is a blind assembly. As such, the containers 150 and the batteries 152 prevent the top section 104 from being positioned over the bottom section 106 incorrectly. The containers 150 and the batteries 152 act as guides to funnel and orient the top section 104 without the user having to pay attention to the exact orientation of the top section 104. Because the containers 150 and the batteries 152 are offset within the bottom section 106, there is only a single correct orientation of the top section 104 that allows the top section 104 to be placed over the bottom section 106 correctly. Similarly, the stop structures 314a, 314b can operate as guides to facilitate the correct positioning of the cap assembly 159. For example, a user may concentrate upon proper alignment of the containers 150a, 150b with the corresponding apertures in the cap assembly 159, thereby implicitly providing a proper alignment of the batteries with their corresponding contacts within the apertures in the cap assembly 159. In some embodiments of the dispenser 100, the dimensions and spacing of the various components will allow one or more of the batteries and tabs to provide a guiding or supplemental guiding function. For example, FIGS. 25A-25L are illustrations of housing structures with varying numbers of installed objects such as the containers 150 and/or batteries 152. The figures illustrate the guiding capabilities of installed objects such as the containers 150 and the batteries 152 as described in the present disclosure, where the installed objects can assist in correct placement of a top section of the housing over a bottom section of the housing.

Figure 25A:
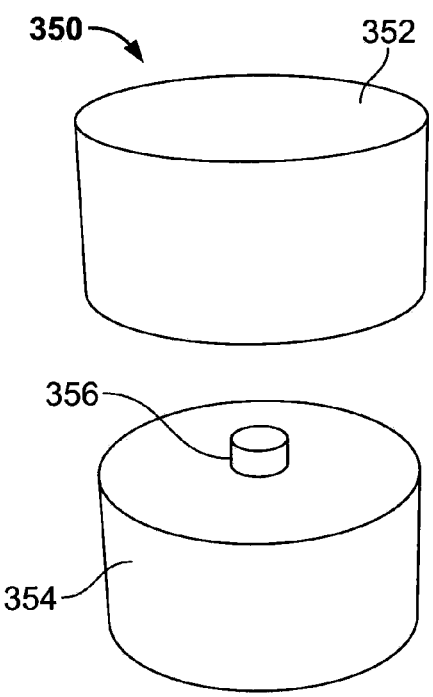
FIGS. 25A-25L are illustrations of various housing structures incorporating different numbers of installed objects such as the containers and/or batteries and demonstrating a guiding capability of the installed objects.
Figure 25B:
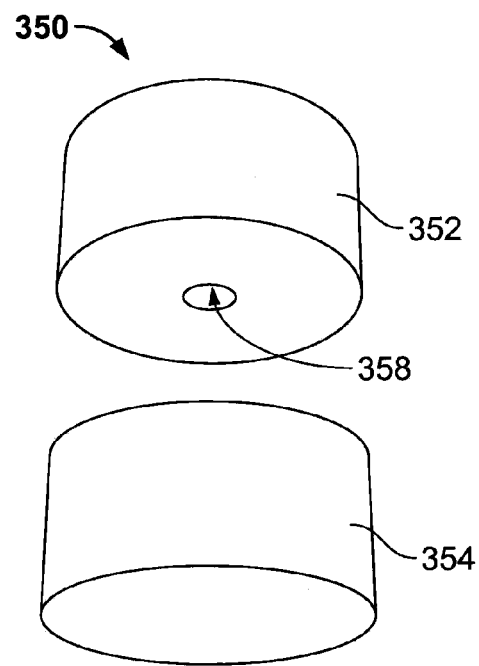

In FIGS. 25A and 25B, a housing 350 is illustrated. The housing 350 comprises top section 352 and bottom section 354 and is configured to contain the contents of the dispenser 100. In one implementation, the housing 350 is configured in accordance with the housing 102 of the present disclosure. The housing 350 includes apertures formed in both the top section 352 and the bottom section 354 for receiving a number of objects, such as the containers 150 or the batteries 152. For example, the apertures may be configured similarly to the apertures 120, 122, 150, or 152 of the present disclosure.

As shown in FIGS. 25A and 25B, only a single object 356 has been installed into the bottom section 354 of the housing 350. With only the single object 356 installed into the bottom section 354, when the top section 352 is mounted to the bottom section 354, the only constraint on the positioning of the top section 352 over the bottom section 354 is that aperture 358 be positioned directly over the object 356. Other than that constraint, there is no limitation on the orientation of the top section 352 with respect to the bottom section 354. In fact, during placement on the bottom section 354, and even when the aperture 358 is positioned about the object 356, the top section 352 can be rotated through 360 degrees. This degree of freedom renders it difficult for a user to correctly position the top section 352 over the bottom section 354. Indeed, the orientation of the top and bottom sections 352, 354 is exacerbated when the combined housing 350 defines a completely symmetrical object, such as a cylinder or sphere, or a partially symmetrical object, such as a square, rectangle, triangle, etc. In fact, the single cylindrical object 356 of the present embodiment provides no guidance to a user to assist in correctly connecting the top section 352 and the bottom section 354 as the exterior surfaces of the sections form a completely symmetrical structure. This is particularly problematic when the object 356 and the aperture 358 are each positioned in a central region of a symmetrical top section 352 and bottom section 354.

In some cases, it is possible to mitigate the problems associated with positioning the top section 352 over the bottom section 354 by offsetting the object 356 and the aperture 358 laterally within the housing 350. In that case, even if the top section 352 is positioned over the bottom section 354 in an incorrect position, the outer surfaces of the top section 352 and the bottom section 354 will be offset from one another. This offset of the top section 352 and the bottom section 356 provides feedback to the user that the two sections are not correctly positioned with respect to one another. At that time the user may make adjustments to correctly position the top section 352 and the bottom section 354.

Figure 25C:
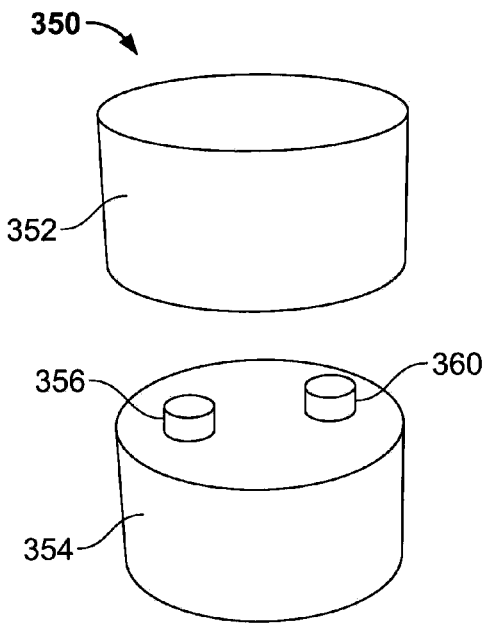
Figure 25D:
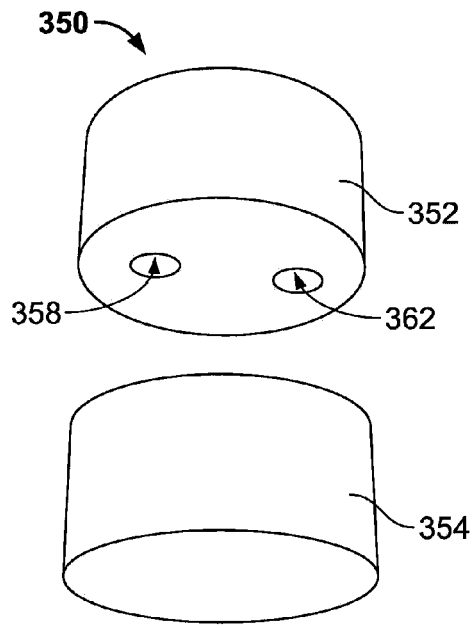

FIGS. 25C and 25D illustrate housing 350 having two objects 356 and 360 installed into the bottom section 354 of the housing 350. The objects 356 and 360 may include, for example, containers 150a and 150b, batteries 152a and 152b or a container 150 and a battery 152. The top section 352 includes two apertures 358 and 362 configured to receive objects 356 and 360. In this arrangement, when positioning the top section 352 of housing 350 over the bottom section 354, the top section 350 can adopt only one of two orientations that would allow each one of apertures 358 and 362 to be positioned over one of objects 356 and 360. In a first orientation, the top section 352 is positioned with the aperture 358 over object 356 and the aperture 362 over the object 360. In the second orientation, aperture 362 is positioned over object 356 and aperture 358 positioned over object 360. Accordingly, the user has a 50/50 chance of correctly positioning the top section 352 over the bottom section 354. This is particularly problematic when both of the apertures 358 and 362 and the objects 356 and 560 are positioned to fall along a central plane of housing 350.

Figure 25E:
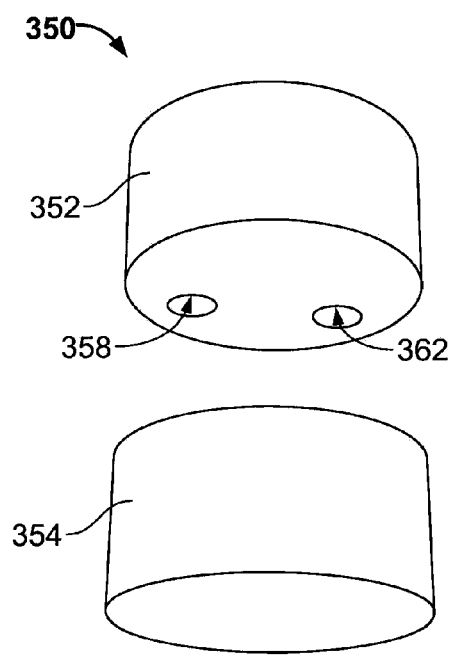
Figure 25F:
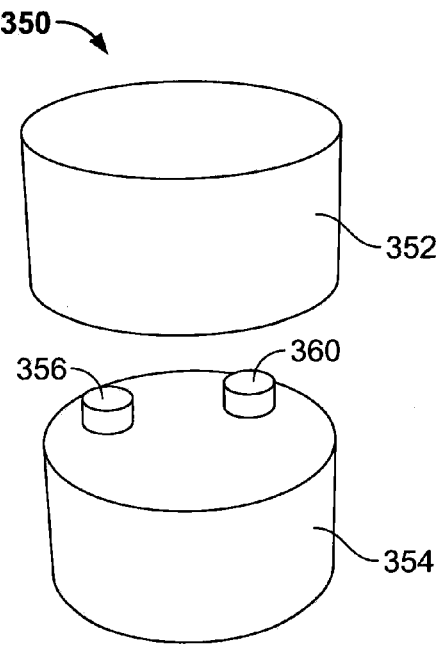

In some cases, it is possible to mitigate the problems associated with positioning the top section 352 over the bottom section 354 by offsetting each of the objects 356 and 360 and the apertures 358 and 362 laterally away from the center plane of housing 350. In that case, even if the top section 352 is positioned over the bottom section 354 in an incorrect orientation, the outer surfaces of the top section 352 and the bottom section 354 will be offset from one another. This offset of the top section 352 and the bottom section 356 provides feedback to the user that the two sections are not correctly positioned with respect to one another. At that time the user may make adjustments to correctly position the top section 352 and bottom section 354 by rotating the top section 352 by 180 degrees. The offset position of objects 356 and 360 and apertures 358 and 362 are shown in FIGS. 25E and 25F.

Figure 25G:
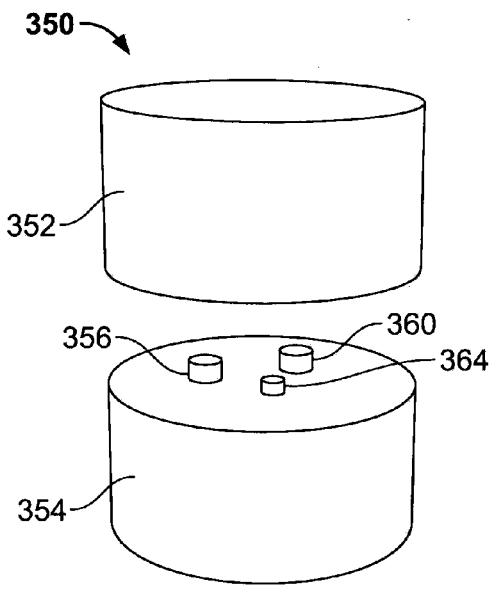
Figure 25H:
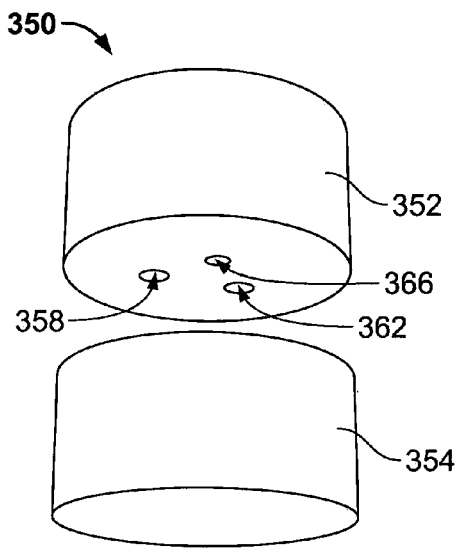

FIGS. 25G and 25H illustrate housing 350 having three objects 356, 360, and 364 installed into the bottom section 354 of the housing 350. The objects 356, 360, and 364 may include a combination of containers 150 and batteries 152. The top section 352 includes three apertures 358, 362, and 366 configured to receive objects 356, 360, and 364. In this arrangement, when positioning the top section 352 of housing 350 over the bottom section 354, the top section 350 can adopt only a single orientation that would allow each one of apertures 358, 362, and 366 to be positioned over one of objects 356, 360, and 364. This is particularly true given that the dimensions of objects that comprise containers 150 are different from the dimensions of objects that comprise batteries 152. Accordingly, with three installed objects 356, 360, and 364 it is possible to correctly position top section 352 over bottom section 254 by using objects 356, 360, and 364 as guides. As such, no external markings or cues are required on the surface of housing 350 to assist a user in the correct positioning. It is also contemplated that the use of varying sized apertures and/or objects may be used in any of the embodiments described herein to supplement the guiding function.

Figure 25I:
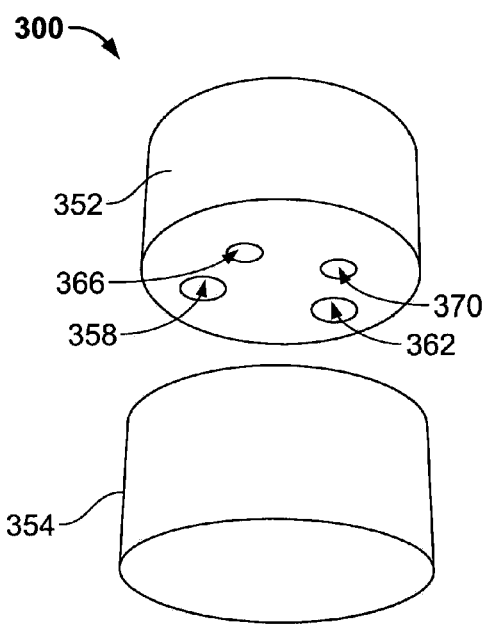
Figure 25J:
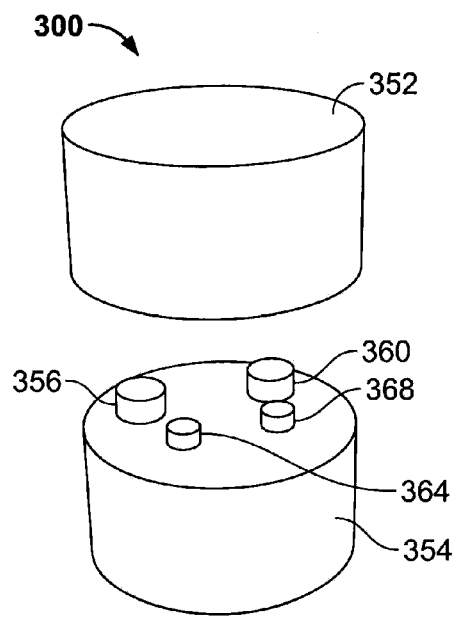

FIGS. 25I and 25J illustrate housing 350 having four objects 356, 360, 364, and 368 installed into the bottom section 354 of the housing 350. The objects 356, 360, 364, and 368 may include a combination of containers 150 and batteries 152. The top section 352 includes three apertures 358, 362, 366, and 370 configured to receive objects 356, 360, 364, and 368. In this arrangement, when positioning the top section 352 of housing 350 over the bottom section 354, the top section 350 can adopt only a single orientation that would allow each one of the apertures 358, 362, 366, and 370 to be positioned over one of objects 356, 360, 364, and 368.

Figure 25K:
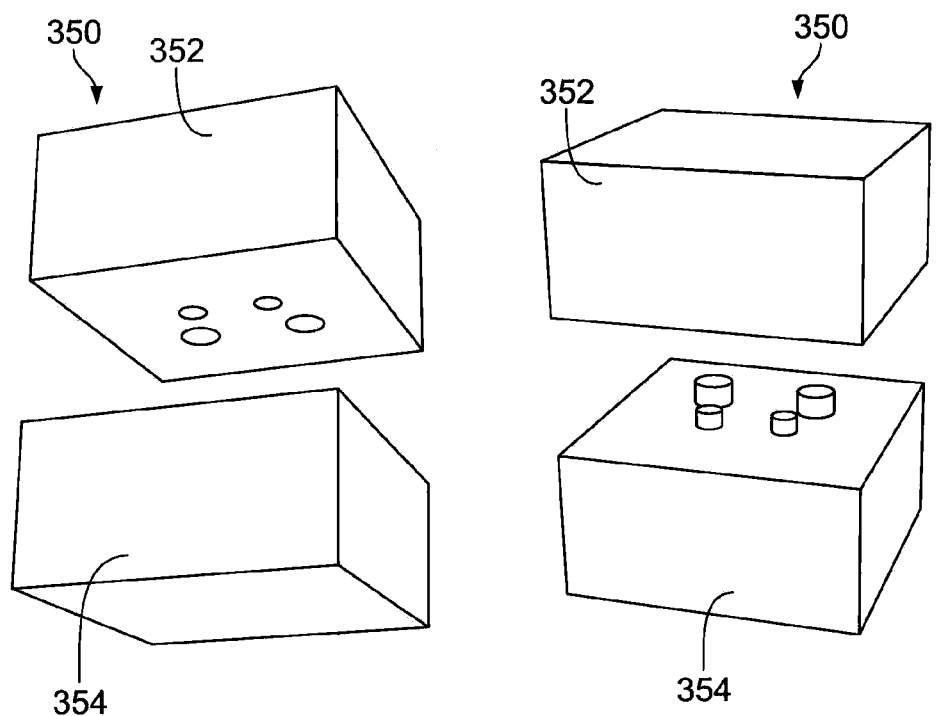
Figure 25L:
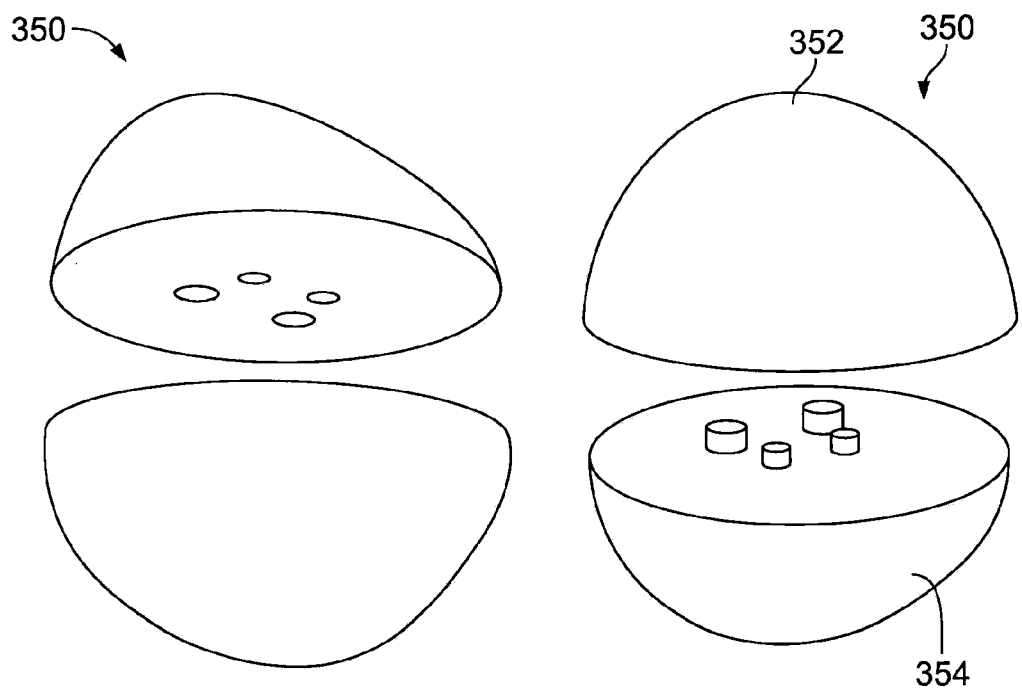

FIGS. 25K and 25L illustrate alternative housing arrangements and geometries incorporating at least four objects positioned within a bottom section 354 of the housing 350, which are each configured to mate to a corresponding aperture formed in the top section 352 of the housing 350. As illustrated, because each of the four installed object provide a user with guidance regarding the correct orientation of the top section 352 with respect to the bottom section 354, irrespective of an outward geometrical shape of housing 350, the user will be able to easily orient the top section 352 correctly over the bottom section 354. With specific reference to FIG. 25K, a partially symmetrical housing 350 is provided in the shape of a square, which provides a further alignment function by limiting a user's potential orientation options to 4 positions. Similarly, the housing 350 shown in FIG. 25L is asymmetric, which provides the user with only a single potential alignment option. It is contemplated that the housing 350 may be constructed with one or more of an asymmetric, partially symmetric, or completely symmetric housing, which may provide a guiding function in lieu of, or in combination with, one or more apertures holding one or more objects in opposing sections of the housing as previously described.

Referring back to FIG. 23, the top section 104 has been seated upon the bottom section 106. The stop structures 314a, 314b have also been positioned over and around the locking tabs 124a, 124b, with the locking tabs 124a, 124b entering the vertical apertures formed in the bottom surface of stop structures 314a, 314b. As shown in FIG. 23, however, although the cap assembly 159 has been properly mated to the bottom section 106 (so that any present containers 150 and batteries 152 have been correctly positioned through their respective apertures in the cap assembly 159), the locking members 166a, 166b are not coupled to either of the stop structures 314a, 314b or the locking tabs 124a, 124b.

In this position, the rectangular apertures 318, 125 in the locking tabs 124a, 124b and the stop structures 314a, 314b are in alignment with the locking members 166a, 166b. Additionally, with the cap assembly 159 correctly positioned over the bottom section 106, the conical-shaped spring contacts 164a, 164b, 164c (see FIG. 4) extending from the cap assembly 159 make positive contact with the electrical contacts 126a, 126b, 126c of the bottom section 106 (see FIG. 2). This allows for an electrical connection between the PCB and controller disposed within the top section 104 and the actuator drive system 200 and selector switch 470 disposed within or otherwise connected to the bottom section 106. Conversely, when the top section 104 is lifted from the bottom section 106, the power is disconnected to the electronics by separating the batteries from their respective contacts in the top section 104 of the cap assembly 159. By only providing electrical energy to the dispenser 100 when the top section 104 is mounted to the bottom section 106, a user may refill the dispenser 100 without risk of being sprayed by the dispenser 100 during the refill process as the actuator drive system 200 cannot operate following disconnection of the top section 104 from the bottom section 106. As such, the dispenser 100 can only be active when the dispenser 100 is fully assembled. Therefore, the separation of the top section 104 and the bottom section 106 effectively operates as on-off switch for dispenser 100 without the user having to take out the battery.

After seating the top section 104 upon the bottom section 106, the two sections are locked to one another as shown in FIG. 24. The sidewall of the top section 104 is rotated so as to move the locking members 166a, 166b toward the stop structures 314a, 314b. The configuration of the prongs of the locking members 166a, 166b provide tactile feedback to a user allowing the user to know that the locking process is complete. Because the cap assembly 159 is configured to rotate within the sidewall 158 of the top section 104, the sidewall (and the attached locks 166a, 166b) can be rotated without modifying the position of the cap assembly 159. As discussed above, the stop structures 314a, 314b assist in preventing rotation of the cap assembly 159 during rotation of the upper sidewall 158 of the top section 104. In the present embodiment, the sidewall is rotated in a clockwise direction (when viewed from the top of dispenser 100). However, in other embodiments the sidewall and locking members 166a, 166b may be modified to rotate in a counter-clockwise direction.

Upon rotation of the sidewall 158, the locking members 166a, 166b are inserted into the aligned rectangular apertures 125, 318 of the locking tabs 124a, 124b and the stop structures 314a, 314b. As described above, the locking members 166a, 166b incorporate retention members or prongs that engage the stop structures 314a, 314b and lock the top section 104 to the bottom section 106. After rotation of the sidewall to insert the locking members 166a, 166b into the stop structures 314a, 314b, openings 110a, 100b formed in the top plate 108 of the top section 104 (see FIG. 1) are positioned over nozzles 180a, 180b of the cap assembly 159. As such, products can be dispensed from the containers 150a, 150b disposed within the dispenser 100 through nozzles 180a, 180b and out of the openings 110a, 100b.

Removal of the top section 104 is accomplished by a user rotating the sidewall 158 of the top section 104 in a counter-clockwise direction (in this embodiment) with sufficient force to disengage the locking members 166a, 166b from the stop structures 314a, 314b and the locking tabs 124a, 124b, thereby placing the sidewall 158 of the top section 104 into the pre-rotation position illustrated in FIG. 23 and allowing for the upward removal of the top section 104 from the bottom section 106. Again, the prongs of the locking members 166a, 166b provide tactile feedback informing the user when the top section 104 and the bottom section 106 are disengaged from one another. In one implementation, power is not disconnected from the main PCB in the top section 104 until the top section 104 is lifted away from the bottom section 106 because the lifting of top section 104 disengages electrical contacts in the cap assembly 159 from the batteries 152a, 152b disposed within the bottom section 106. Additionally, this action disengages spring contacts 164a, 164b, 164c of the cap assembly 159 from the contact pads 126a, 126b, 126c of the bottom section 106.

Figure 48A:
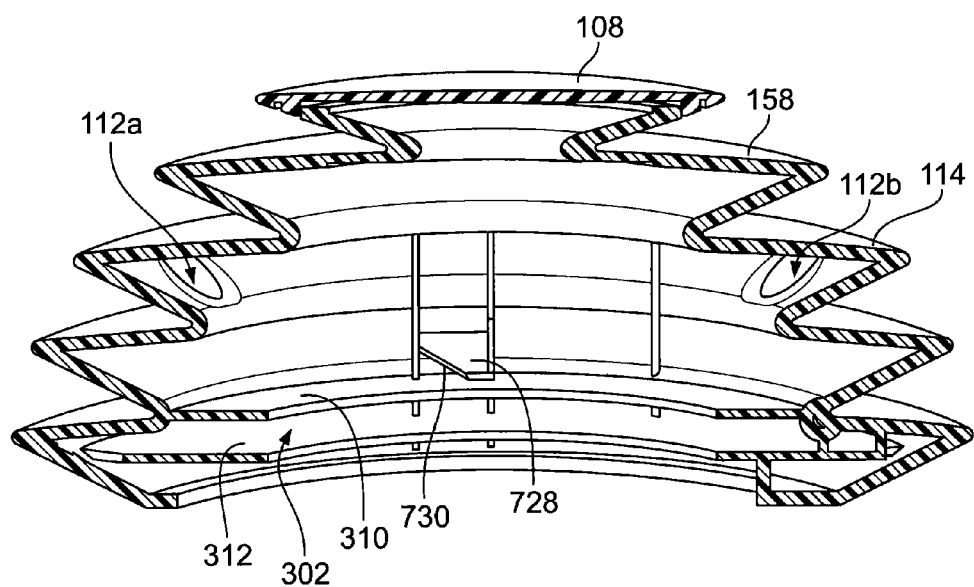
FIGS. 48A-48D are illustrations of the top section of the housing incorporating a mechanism for disconnecting power when the top section of the dispenser is unlocked from the bottom section.

In other embodiments of dispenser 100, power is not provided to the components of the dispenser 100 until the sidewall 158 of the top section 104 is locked into place, which provides for the removal of power from the dispenser 100 upon rotation of the top section 104 away from the locked position. For example, FIG. 48A is a view of the interior surface of the upper sidewall 158 of the top section 104. A wedge 728 is mounted to the interior surface of the upper sidewall above the groove 302. The wedge 728 may be integrally formed with the sidewall 158. Alternatively, the wedge 728 may comprise a separate structure that is affixed to the sidewall 158, for example, by an adhesive, an interference fit, a fixture such as a screw or bolt, or any combination thereof.

The wedge 728 is configured to rotate with the sidewall 158 of the top section 104 as the top section 104 transitions between a locked and unlocked position with respect to the bottom section 106 of housing 102. When the top section 104 is rotated into an unlocked position, wedge 728 is configured to push between one of the batteries 152 and its respective electric contact 410 mounted to the top of one of apertures 162, thereby disconnecting that battery 152 from its electric contact and disconnecting the electrical power circuit of dispenser 100. A front face 730 of the wedge 728 may be sloped to facilitate the insertion of the wedge 728 between the battery 152 and its respective electrical contact.

Figure 48B:
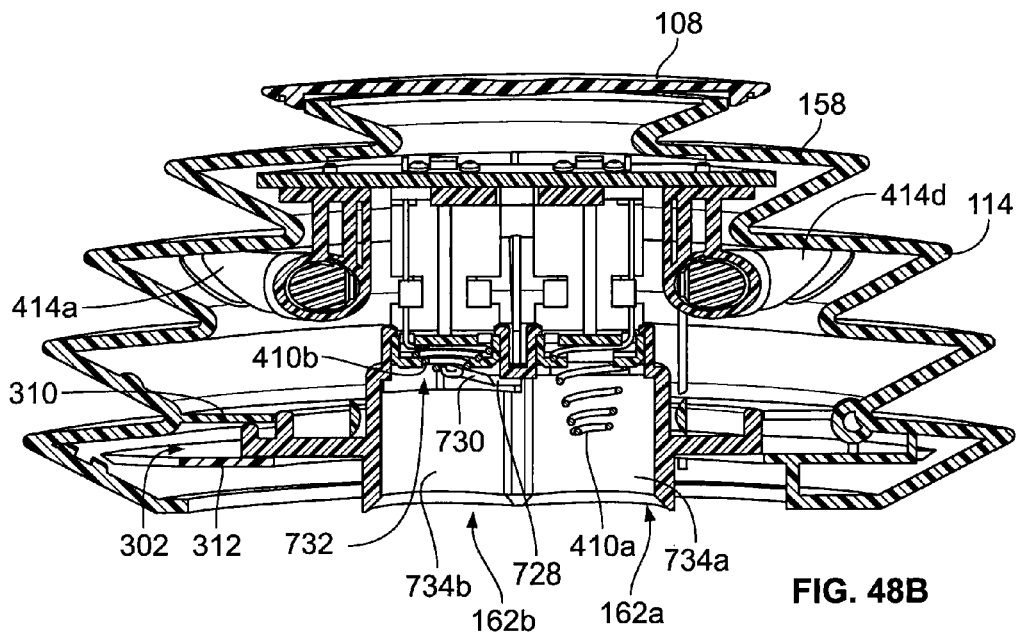

To further illustrate this implementation, reference is had to FIG. 48B, which is a sectional view of the top section 104 taken through apertures 162. The top section 104 is shown in its locked position, whereby power is supplied to the components of the dispenser 100. As shown in FIG. 48B, an aperture 732 is formed in wall 734b that defines the aperture 162b. The aperture 732 is sized to receive the wedge 728 when the top section 104 is rotated into an unlocked position with respect to the bottom section 106. In FIG. 48B, however, the top section 104 is shown in its locked position. As such, the wedge 728 is withdrawn from the aperture 732, thereby allowing for normal operation of the dispenser 100.

Figure 48C:
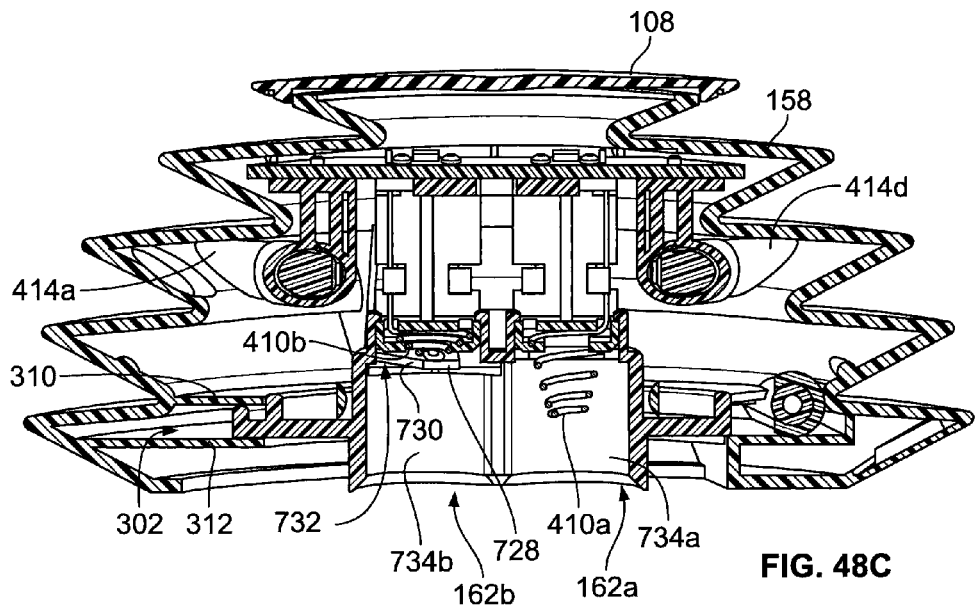
Figure 48D:
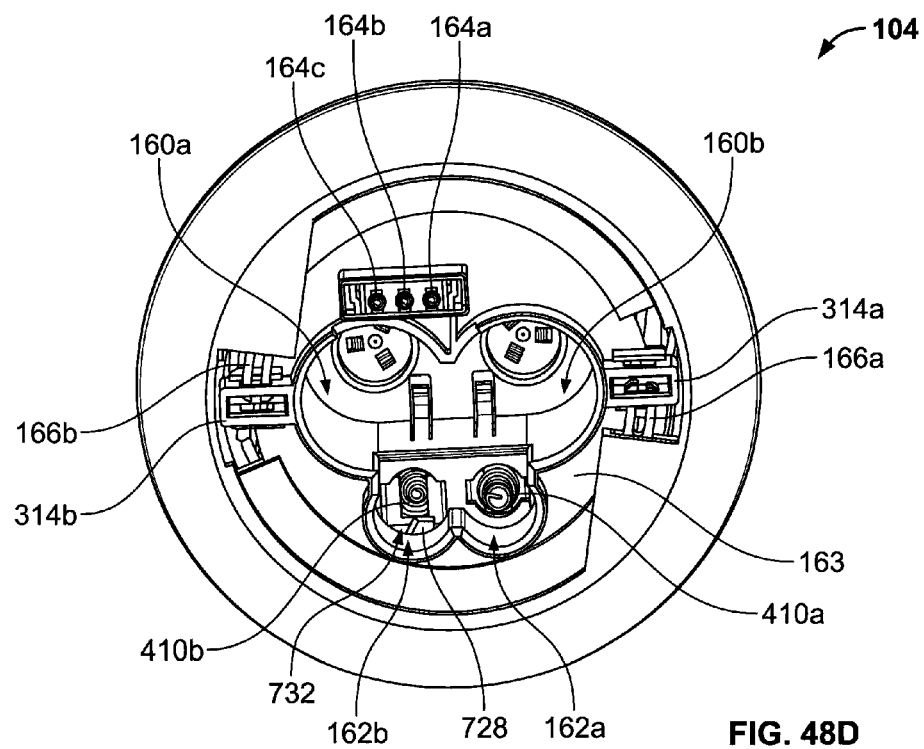

In contrast, FIG. 48C is a sectional view of the top section 104 taken through apertures 162 showing the top section 104 unlocked from the bottom section 106. Because the top section 104 has been rotated into the unlocked position, the wedge 728 has moved through the aperture 732 to occupy a space within apertures 162a. In that position, the wedge 728 is forced between the battery 152b disposed within aperture 162b and the battery's respective electrical contact 410b, thereby disconnecting electrical power to the dispenser 100. For further illustration, FIG. 48D is a bottom view of the top section 104 showing the top section 104 transitioning into an unlocked configuration with wedge 728 penetrating through aperture 732 into aperture 162b.

In other implementations, different locking structures (and different numbers of locking structures), such as buckles, locking pins, clasps, hooks, or snaps can be used to connect the top section 104 and the bottom section 104 of the dispenser 100. Alternatively, each of the locking members 166a and 166b could include ferromagnetic structures configured to couple to complementary magnetic structures positioned on the bottom section 106 of the housing 100. Alternatively, other separate mechanical locking structures could be used to couple the top section 104 to the bottom section 106. For example, a separate locking structure, such as a locking pin or key, could be inserted into the housing 100 after the top section 104 is connected to the bottom section 106 to lock the two sections of the housing 102 together. In some cases, the locking members 166 lock the top section 104 to the bottom section 106 such that a release control or button must be activated in order to separate the two sections of the housing 102. Generally, the locking structures and, therefore, the locking members 166a and 166b may comprise a variety of shapes as to properly fit in their adjoining locking apertures. Slip fit dowels or similar structures, for example, may be incorporated into the locking structures to attach the top section 104 of the dispenser 100 to the bottom section 106.

Figure 26:
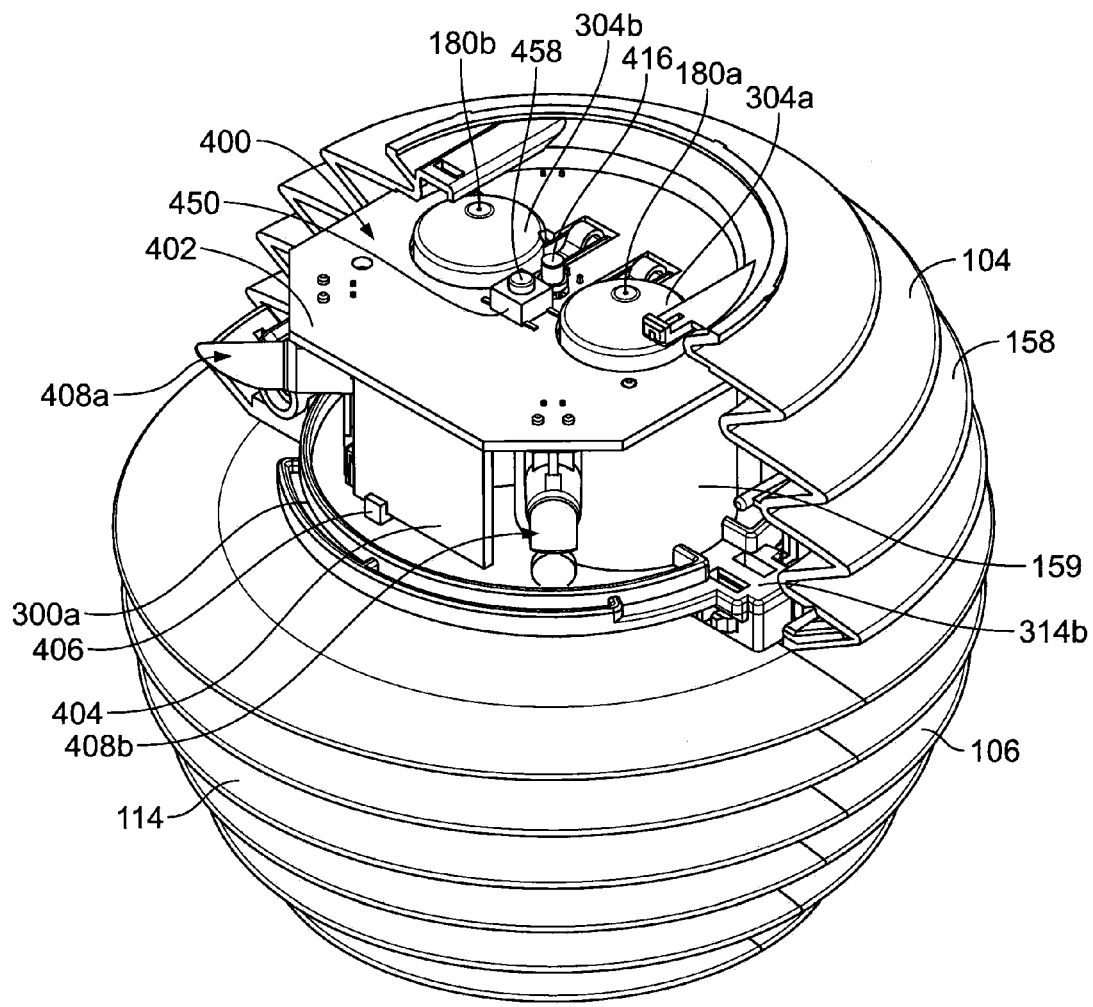
FIG. 26 is an isometric view of a dispenser with portions thereof removed to show a PCB.

As described above, the top section 104 of the housing 102 includes a PCB to which dispenser 100's controller is mounted. FIG. 26 is an isometric view of the dispenser 100 with portions of the device removed to expose a PCB 402 or other substrate over which the components on the controller are mounted. As described below, the controller mounted thereon receives input from a number of systems of the dispenser 100 in order to control the operation of the dispenser 100 and to determine when product should be dispensed from one of the containers 150a, 150b and from which of the containers 150a, 150b the product should be dispensed. The device includes a motion detection system that can be used to dispense product upon detecting movement (that is, the presence of an individual). Alternatively, the dispenser 100 may be configured to avoid dispensing product when movement is detected. For example, if the dispenser 100 is configured to dispense an insecticide product, it may be preferable that the product be dispensed when people are not present. Additionally a mode selector switch connected to the bottom section 106 can select from a number of operational modes that control how the controller uses data received from the motion detector system. Additionally, a manual user input can communicate a signal to the controller to allow a user to manually control when product is dispensed.

As shown in FIG. 26, the PCB 402 is mounted over the cap assembly 159. In one implementation, the PCB 402 incorporates additional PCB structures 404 that project downwardly away from the PCB 402 to contact a surface of the cap assembly 168 and to provide support to the PCB 402. The vertical walls 404 can be supported by clip structures 406 that are fixed to the cap assembly 159. In the present embodiment, the vertical walls 404 also provide support for the structures that allow for electrical interconnections between the components of the PCB 402 and other components of the dispenser 100, such as the actuator system 200 and the batteries 152a, 152b. The PCB 402 may also be fixed to the cap assembly 159 using a number of fasteners such as screws or bolts, an adhesive, or combinations thereof.

The PCB 402 incorporates apertures through which the housing structures 304a and 304b of the cap assembly 159 can project. The housing structures 304a and 304b incorporate nozzles 180a, 180b of the cap assembly 159 through which product is dispensed.

LED 416 is connected to the PCB 402 and is electrically connected to the controller of the dispenser 100. The LED 416 may be illuminated, for example, when the controller detects movement near the dispenser 100. The illumination may also be useful for testing the dispenser 100 to ensure that the motion detecting system is operating correctly. The illumination of the LED 416 can also be useful to an end user that may use the illumination to verify that the dispenser 100 is correctly positioned in order to detect movement and is otherwise functioning correctly. In various implementations, the speed and intensity with which the LED 416 is illuminated can be controlled. For example, if the optical sensors of the dispenser 100 detect a high ambient light level, the LED 416 may be illuminated with a greater intensity to ensure that the LED 416 can be viewed (for example, in a bright room). Alternatively, when the optical sensors of the dispenser 100 detect a relatively low ambient light level, the LED 416 may be illuminated with a lesser intensity in accordance with the surroundings. As such, the illumination of the LED 416 can be adjusted based upon various functional considerations. In some cases, for example, the LED 416 may be illuminated so as to provide a gradual glow, for example, rather than be illuminated in an abrupt on/off configuration. The LED 416 may be utilized to communicate any appropriate information to a user, such as when a container 150 is empty and requires replacing, when batteries are low, or when the dispenser 100 is not operating correctly.

Figure 27:
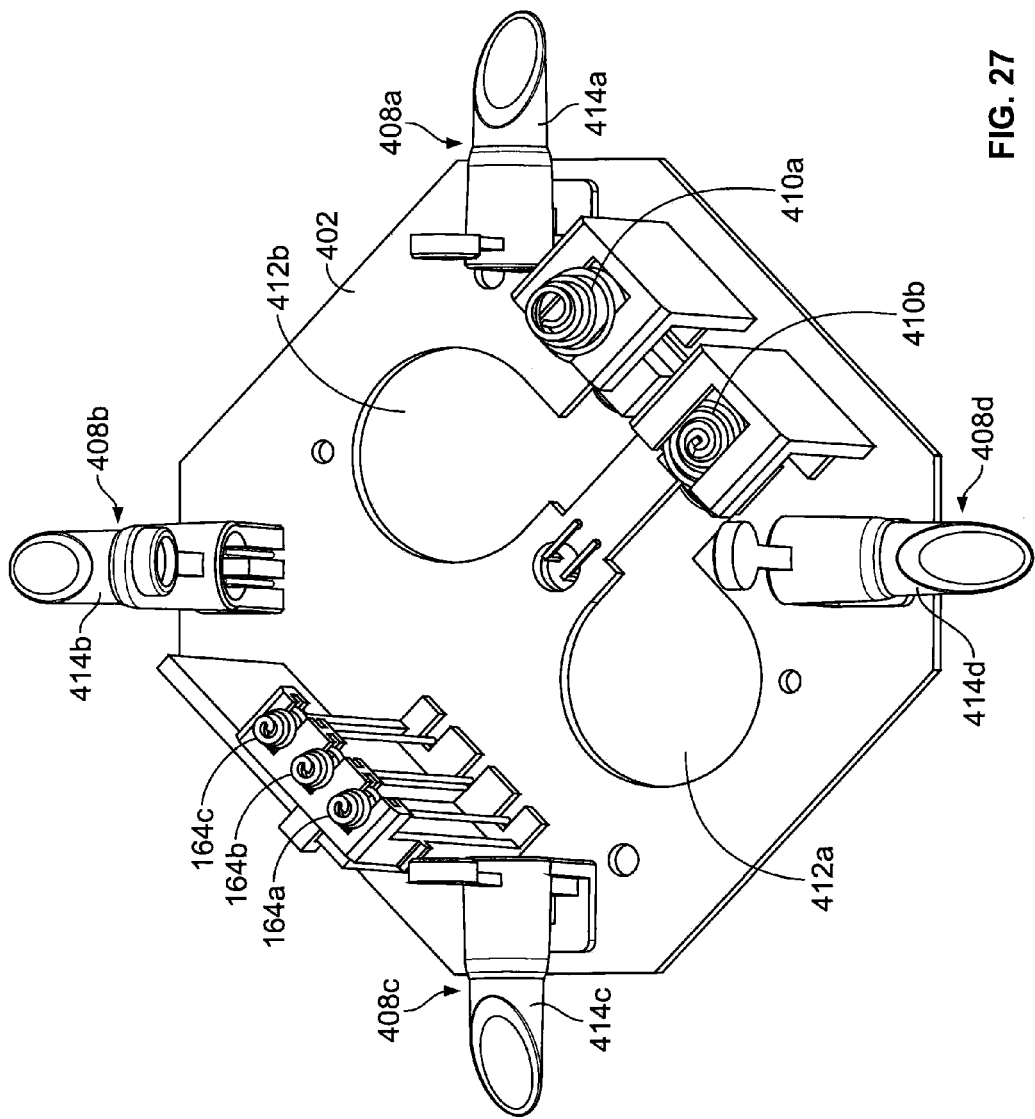
FIG. 27 is an isometric view of a bottom surface of the PCB of FIG. 26.

FIG. 27 is an isometric view of the bottom surface of the PCB 402. As shown in FIG. 26, to install the PCB 402 into the top section 104, the PCB 402 is inverted (from the view shown in FIG. 27) and positioned over the cap assembly 159. The PCB 402 includes apertures 412a and 412b for receiving a portion of the housing structures 304a and 304b. Additionally, the spring contacts 164a, 164b, 164c are connected to the PCB 402 for forming an electrical connection between a controller mounted to the PCB 402 and the actuator drive system 200 and a selector switch 470 of bottom section 106 when the top and bottom sections of dispenser 100 are connected to one another. Additionally, the PCB 402 incorporates battery terminals 410a and 410b for forming an electrical connection with the batteries 152a, 152b of the dispenser 100. When the PCB 402 is installed over the cap assembly 168, battery terminals 410a and 410b project downwardly into the upper portion of apertures 162a, 162b for contacting a terminal of the batteries 152a, 152b disposed therein.

The PCB 402 also incorporates a number of sensors 408a, 408b, 408c, 408d. In one implementation, each sensor 408 comprises a light-sensing element, such as a photodetector or photodiode light detector, photoresistor, photodiode, or phototransistor. Each of the sensors 408a, 408b, 408c, 408d may incorporate a lens cover that may be configured to protrude from the front of the sensors 408a, 408b, 408c, 408d. The lenses may be configured to ensure a wide field of view for each of the sensors 408a, 408b, 408c, 408d while also providing protection. The incorporation of such a lens may be advantageous where one or more of the sensors 408a, 408b, 408c, 408d incorporates a passive infra-red sensor, such as a Panasonic PIR MP motion sensor AMN1 (as manufactured by Panasonic), since the motion would not need to occur directly in front of the sensor to be detected. Similarly, where one or more of the sensors 408a, 408b, 408c, 408d are additionally or alternatively provided as a laser sensor or a flickering light sensor, the incorporation of such a lens may afford the sensor a wider field of view.

Each sensor 408 incorporates one of cylindrical tubes 414a, 414b, 414c, 414d. The tubes 414a-d operate as sensory shields to reduce and/or prevent interference with the sensory path of each sensor positioned at the end of each tube 414a-d. Further, the tubes 414a-d may operate as sensory shields that restrict the field of view of the sensor to provide improved sensing characteristics for each of the sensors 408a, 408b, 408c, 408d. While the present embodiment contemplates utilizing the detection of varying light levels to trigger various operations of the dispenser 100, it is contemplated that detecting varying levels of light can also indicate the presence or absence of an object, e.g., a person, and that such a sensor may also be considered a motion sensor as well as a photodetector, a photodiode light detector, or a light sensor. In other implementations, though, the sensors may detect other signals in order to control an operation of the dispenser 100. For example, in addition to or in place of optical or light sensors, other sensors such as accelerometers or acoustic, humidity, temperature, pressure, vibration, or chemical (e.g., scent) sensors may be incorporated into the dispenser 100. In that case, the other types of sensors may optionally be intermingled with light or optical sensors so that the various sensors can operate in cooperation with one another. For example, the dispenser 100 could be configured to dispense product upon detecting movement, or if a humidity level within a particular room is too low or too high. Additionally, by using scent-sensing sensors, the dispenser 100 could be configured to dispense product upon sensing a particular type of scent, odor, or component and/or a lack of the scent, odor, or component.

When the PCB 402 is installed into the top section 104, the apertures of the tubes 414a-d align with the apertures 112 formed around within the sidewall of the top section 104. Note, however, that the tubes 414a-d may only align with the apertures 112 after the top section 104 is locked to the bottom section 106, as described above, therefore requiring that the sidewall 158 of the top section 104 be rotated about the cap assembly 159 to a particular position.

Figure 28:
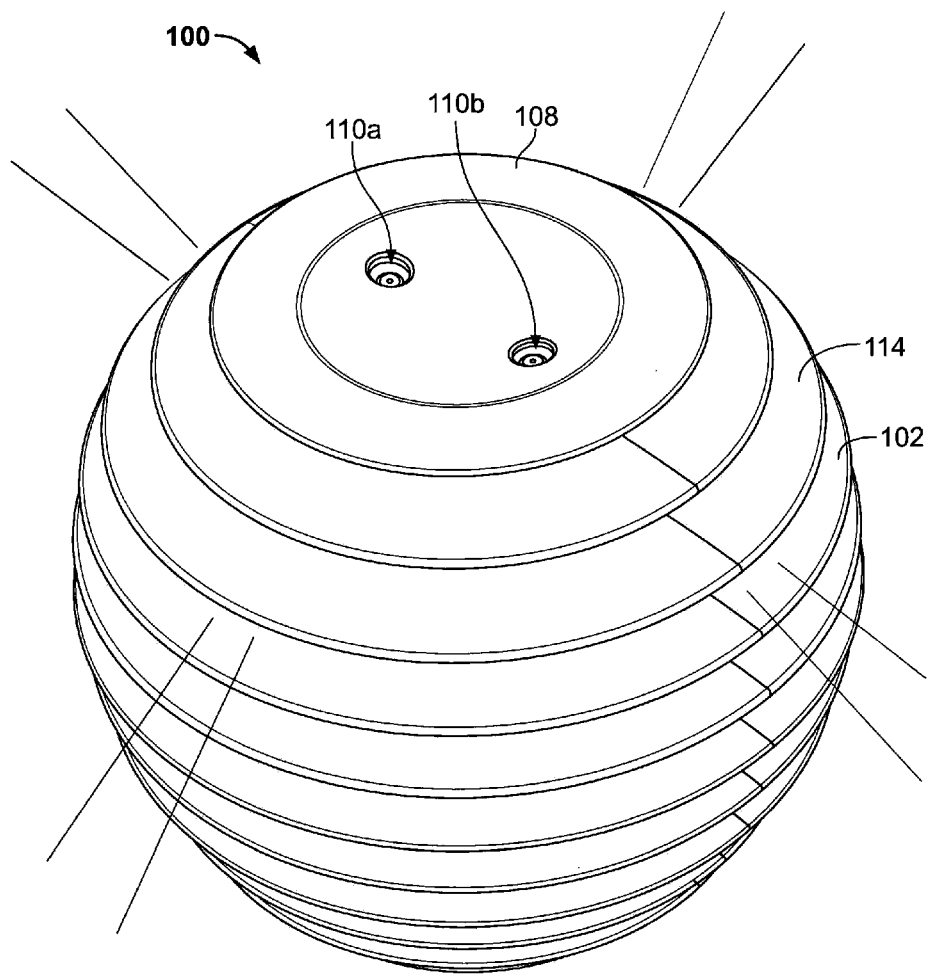
FIG. 28 is an isometric view of a dispenser further depicting a sensory path of the dispenser.

In one embodiment, the field of view of each sensor 408a-d is characterized as a right circular cone with a viewing angle of approximately 10 degrees off the center axis, i.e., a total field of view of 20 degrees. Therefore, the present embodiment, which utilizes four sensors, provides an 80 degree field of view. In other embodiments, it is contemplated that the field of view of each sensor is within a range of about 10 degrees to about 170 degrees, and in a different embodiment within a range of about 15 degrees to about 90 degrees, and in another embodiment within a range of about 20 degrees to about 45 degrees. FIG. 28 is an isometric view of the dispenser 100 illustrating exemplary fields of vision of the detectors 408a-d in a four-detector implementation where the fields of vision are distributed about the dispenser 100. In other implementations, though, different numbers of sensors and/or detectors 408 and corresponding apertures 112 may be utilized to provide the dispenser 100 with different light and/or motion sensing capabilities and a modified field of vision.

Figure 29D:
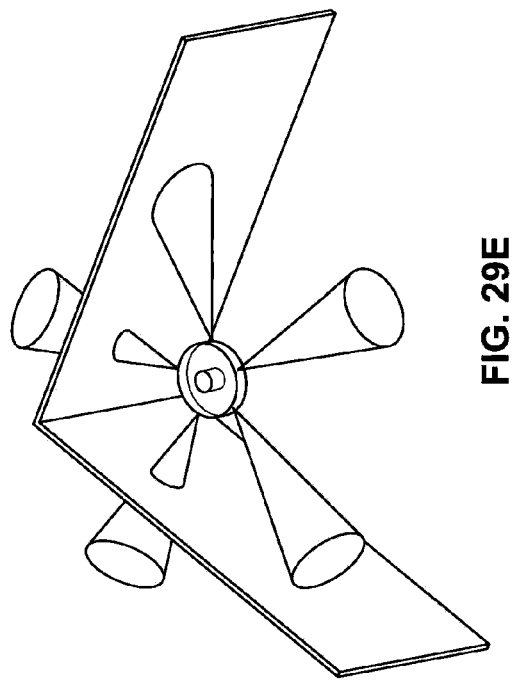

For example, FIGS. 29A-29F are images illustrating various positioning scenarios for the dispenser 100 units having 3, 4 or 5 motion detectors. FIGS. 29A-29F illustrate common use cases for the dispenser 100, wherein the dispenser 100 is positioned adjacent a right corner wall. In FIGS. 29A and 29B a three-detector dispenser 100 is illustrated. Because the detectors are evenly distributed about the perimeter of the dispenser 100, in a first scenario (FIG. 29A) a single detector has a clear view of the space. In a second scenario (FIG. 29B), there are at least two sensors that, even though they have partially obstructed views, are capable of observing the space. Accordingly, even in the second scenario, the detectors of the three-detector dispenser 100 are capable of observing some movement within the space.

In FIGS. 29C and 29D a four-detector dispenser 100 is illustrated. Because the detectors are evenly distributed about the perimeter of dispenser 100, in a first scenario (FIG. 29C) a single detector has a clear view of the space, while two detectors have obstructed views of a relatively small portion of the space. In a second scenario (FIG. 29B), there are at least two sensors that, even though they have somewhat obstructed views, are capable of observing the space. Accordingly, even in the second scenario, the detectors of the four-detector dispenser 100 are capable of observing some movement within the space.

Figure 29F:
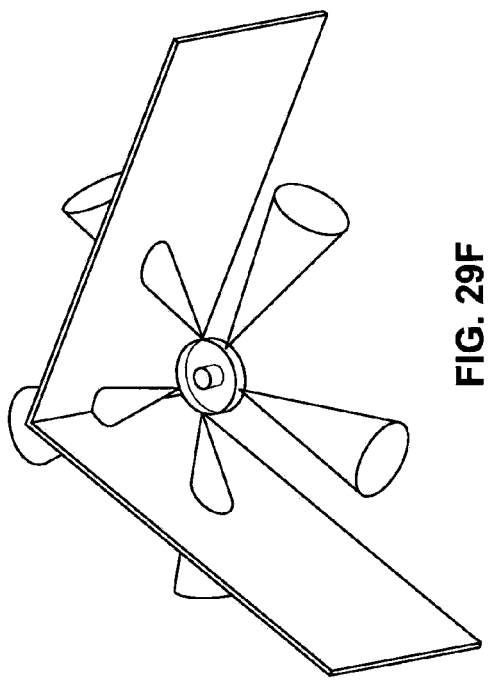
Figure 29E:
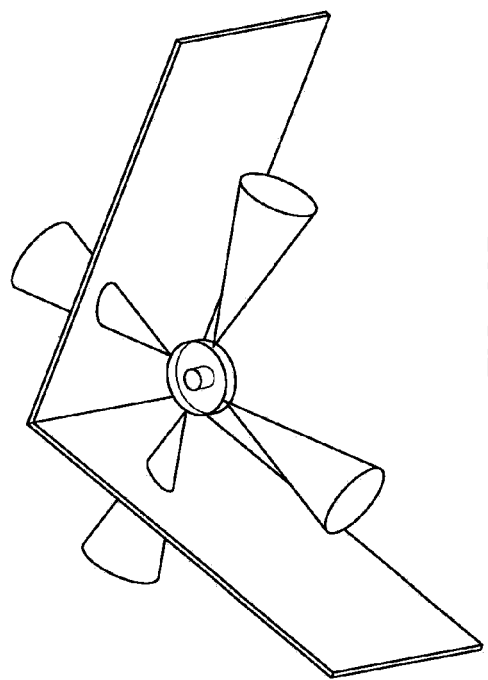
Figure 33B:
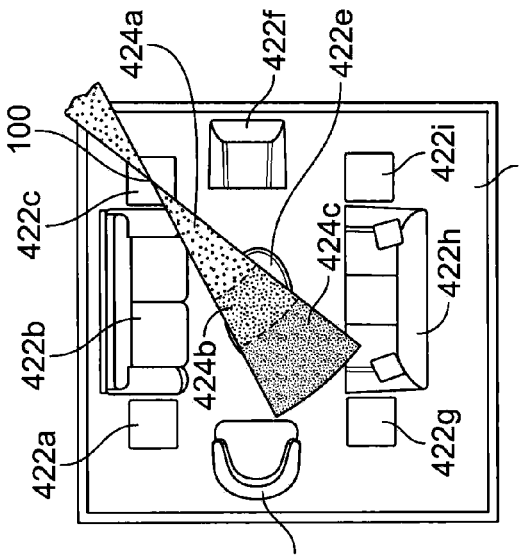
Figure 33A:
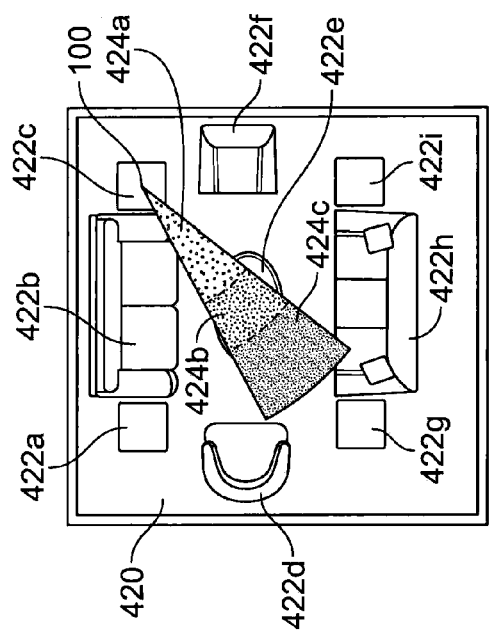
Figure 33C:
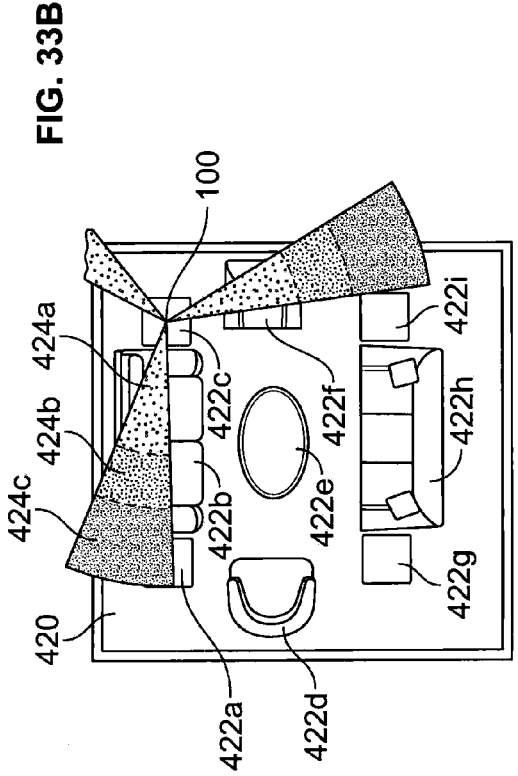
Figure 34D:
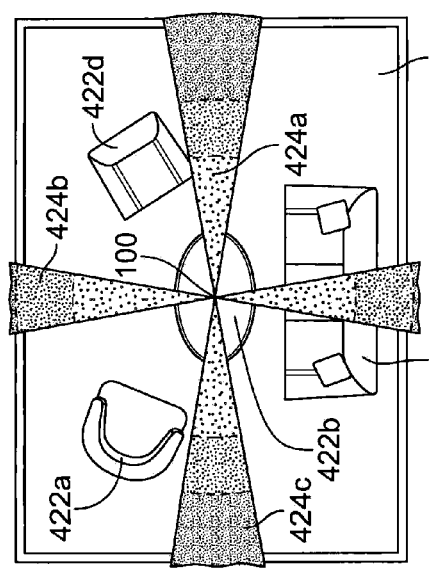
Figure 34E:
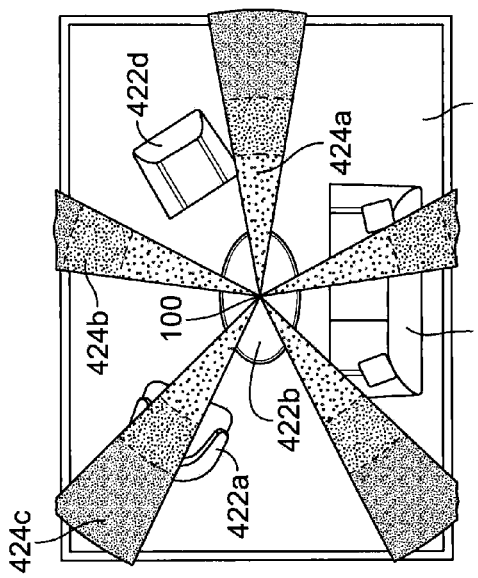
Figure 34F:
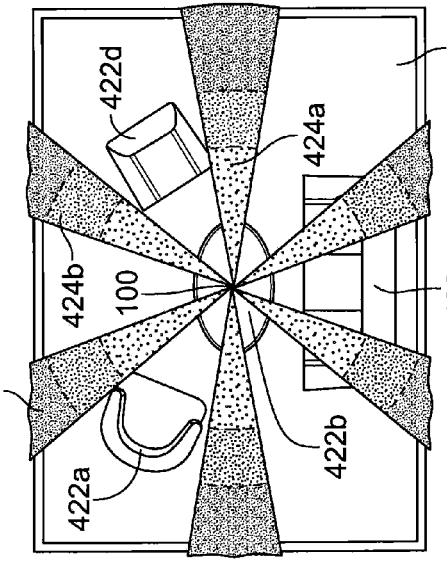
Figure 35E:
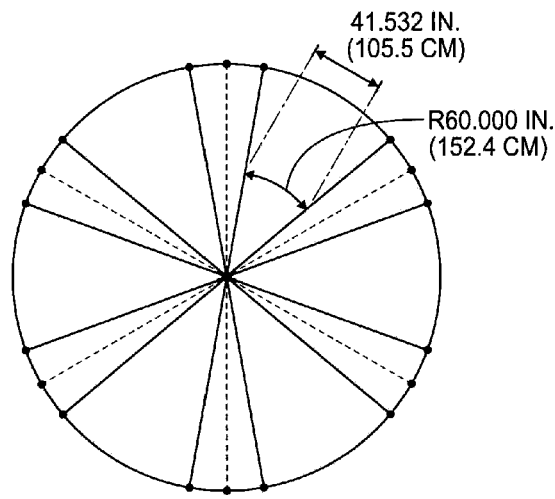

In FIGS. 29E and 29F a five-detector dispenser 100 is illustrated. Because the detectors are evenly distributed about the perimeter of the dispenser 100, in a first scenario (FIG. 29E) a single detector has a clear view of the space, while two detectors have partially obstructed views of the space. In a second scenario (FIG. 29B), there are at least two sensors that have a relatively unobstructed view of the space. Accordingly, even in the second scenario, the detectors of the five-detector dispenser 100 are capable of observing movement within the space.

As an additional example, FIGS. 30A-30F show overhead views of a 12 ft×12 ft (3.66 m×3.66 m) room containing dispenser 100's having 1, 2, 3, 4, 5, and 6 motion sensors, respectively. As shown in each figure, the dispenser 100 is positioned in a central region of each room 420, with the room containing various pieces of furniture 422a, 422b, 422c, and 422d. The figures illustrate the respective fields of vision of the different motion detection sensors incorporated into each dispenser 100. Each field of vision is shown in the figures in three segments representing the field of vision at 5 feet (1.52 m) (element 424a), 7 feet (2.13 m) (element 424b), and 10 feet (3.05 m) (element 424c). It is contemplated that various types of sensors will be used that have varying effective sensory ranges. However, the present embodiments illustrate how a relatively simple sensor with at least a sensory range of 5 feet (1.52 m) affords significant room coverage in a standard 12 ft×12 ft (3.66 m×3.66 m) room. Use of multiple sensors in such a device allows for an effective 10 foot sensory range if two sensors are disposed opposite one another. Further, it has been found that the effective use area of a room by consumers is not typically bounded by the outer wall of a room, rather, the placement of furniture and standard movement paths through rooms are identifiable. In the present embodiments, it may be seen that a user path is defined between the furniture 422d and the furniture 422a-c, which is positioned closer to the dispenser. This user path defines a high volume pathway for user's to walk through, which is within the closest sensory range of the dispenser. Once again, while any type of sensor with any range may be used, it may be possible to utilize a less expensive sensor with a shorter range in a standard room by using a multi-directional sensing dispenser that is placed in a center of a room. Further, the advantages of such a multi-directional sensing dispenser may be improved in some embodiments by utilizing sensors with longer or shorter detection ranges.

As illustrated, as the number of sensors increases, the percentage of the room 420 that may be observed by the dispenser 100 increases correspondingly. In the dispenser 100 containing only a single motion sensor, a portion of the room cannot be observed by the dispenser 100. As such, an individual may pass through the room 420 without triggering the motion sensor. As the number of sensors increases, however, and the coverage of the room 420 increases, the likelihood that movement within the room 420 is detected increases significantly.

FIGS. 31A-31F show overhead views of a 16 ft×16 ft (4.88 m×4.88 m) room containing dispenser 100's having 1, 2, 3, 4, 5, and 6 motion sensors, respectively. As shown in each figure, the dispenser 100 is positioned towards a central region of each room 420, with the room containing various pieces of furniture 422a, 422b, 422c, 422d, and 422e. As illustrated, as the number of sensors increases, the percentage of the room 420 that may be observed by dispenser 100 increases correspondingly. In the present embodiment, a user path may be defined by an area around the furniture 422d and 422c and between the furniture 422a, c, and e and the furniture 422b. Indeed, such pathways are best characterized as areas that users may walk, which are adjacent furniture and not adjacent walls, i.e., that are within 2 feet (0.61 m) of a piece of furniture and not within 2 feet (0.61 m) of a wall.

FIGS. 32A-32F show overhead views of a 16 ft×16 ft (4.88 m×4.88 m) room containing dispenser 100's having 1, 2, 3, 4, 5, and 6 motion sensors, respectively. As shown in each figure, the dispenser 100 is positioned towards a side of each room 420, with the room containing various pieces of furniture 422a, 422b, 422c, 422d, 422e, and 422f. As illustrated, as the number of sensors increases, even though a number of the motion sensors are blocked by the perimeter of the room 420, the percentage of the room 420 that may be observed by the dispenser 100 increases correspondingly. This embodiment illustrates the advantages of the presently described dispensers in that placement of the device against a wall may effectively block traditional dispensers that only utilize a single sensor. In the present embodiment, inadvertent placement of the dispenser 100 still affords the user significant sensory coverage, particularly when a greater number of sensors are used. It is also readily seen that the probability that a user pathway is within a sensory path increases with a greater number of sensors, which is important in scenarios where users do not specifically orient a dispenser or it's one or more sensors when placing it in a room. While the advantages of having sensors with greater sensory ranges is apparent in larger sized rooms, the advantages of sensors with a more limited sensory path may still be realized if such a sensory path falls within a user pathway, thereby allowing detection of a user in a high volume pathway regardless of the fact that the sensor pathway may not extend the entire length of the room.

However, it is also contemplated that sensors with detection ranges extending greater than 10 feet (3.05 m) may be used in any of the embodiments described herein. For example, in one embodiment, the dispenser could utilize one or more IR detectors, such as a common Passive Infra-Red (PIR) Sensor which may be categorized as a pyroelectric device.

FIGS. 33A-33F show overhead views of a 16 ft×16 ft (4.88 m×4.88 m) room containing dispenser 100's having 1, 2, 3, 4, 5, and 6 motion sensors, respectively. As shown in each figure, the dispenser 100 is positioned towards a side of each room 420, with the room containing various pieces of furniture 422a, 422b, 422c, 422d, 422e, 422f, 422g, 422h, and 422i. As illustrated, as the number of sensors increases, even though a number of the motion sensors are blocked by the perimeter of the room 420, the percentage of the room 420 that may be observed by the dispenser 100 increases correspondingly.

FIGS. 34A-34F show overhead views of an 18 ft×13 ft (5.49 m×5.49 m) room containing dispenser 100's having 1, 2, 3, 4, 5, and 6 motion sensors, respectively. As shown in each figure, the dispenser 100 is positioned towards the center of each room 420, with the room containing various pieces of furniture 422a, 422b, 422c, and 422d. As illustrated, as the number of sensors increases, the percentage of the room 420 that may be observed by the dispenser 100 increases correspondingly.

FIGS. 35A-35E are schematic illustrations showing fields of vision for dispenser 100's having 2, 3, 4, 5, and 6 sensors, respectively. In each figure, the field of vision of a single sensor is 20 degrees. As illustrated, as the number of sensors is increased, the total field of vision of the dispenser 100 increases accordingly. However, as the number of sensors increases, each additional sensor increases the percentage of total coverage by a smaller amount.

Figure 36:
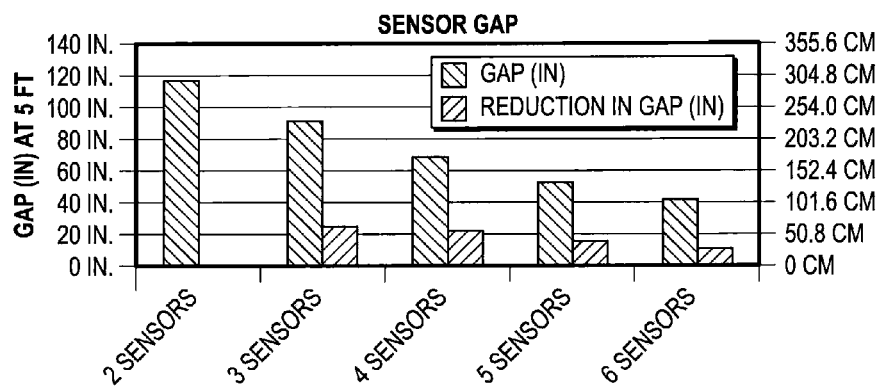
FIG. 36 is a bar chart illustrating the reduction in gap resulting from the addition of sensors to the dispenser 100.

FIG. 36 is a bar chart illustrating the effect of introducing additional sensors to the dispenser 100. The chart illustrates the gap between the fields of vision for sensors at a distance of 5 feet (1.52 m) away from the dispenser 100. Accordingly, at 5 feet (1.52 m) away from a dispenser 100 having two sensors with fields of vision of 20 degrees, the distance between the edges of the fields of visions for the two sensors is approximately 120 inches (304.8 cm). Similarly, for a three-sensor dispenser 100 the gap is approximately 92 inches (233.68 cm). The chart also shows the percentage reduction in the gap between sensors that results from the inclusion of an additional sensor in the system. As seen, the percentage reduction in gap values decrease as the number of sensors is increased. The percentage reduction in gap may be useful in selecting the number of sensors to utilize in a dispenser. In one embodiment, an additional sensor may not be used if the percentage reduction in gap is less than about 20%, in another embodiment an additional sensor may not be used if the percentage reduction in gap is less than about 15%, and in yet another embodiment an additional sensor may not be used if the percentage reduction in gap is less than about 10%. In one implementation of the present dispenser 100 system, therefore, four sensors are used because the marginal improvement in the dispenser 100's field of vision by the addition of a fifth sensor does not outweigh the additional cost of incorporating the fifth sensor into the system. Depending on the use of the dispenser, In other embodiments, the field of view of each sensor may vary, e.g., a sensor may have a field of view within a range of about 10 degrees to about 170 degrees, and in a different embodiment within a range of about 15 degrees to about 90 degrees, and in another embodiment within a range of about 20 degrees to about 45 degrees. In these embodiments, the number of sensors utilized may provide for increased or decreased reductions in the gap as more sensors are utilized.

The capability of the dispenser 100 to observe movement within a particular room or space given any orientation of the dispenser 100 is important for use of the dispenser 100. As seen in FIG. 1, the housing 102 of the dispenser 100 may have a generally spherical design. Additionally, the apertures 112 through which dispenser 100 detects movement are generally hidden from view by the fins 114 of the housing 102. As such, the user is likely to place the dispenser 100 without consideration of the device's orientation or the positioning of the various apertures 112. In fact, the true orientation of the dispenser 100 is purposefully hidden from the user due to the outward appearance of the dispenser 100. As a consequence, the user will not consider the orientation of the dispenser 100 and, consequently, the position of the apertures 112, when placing the dispenser 100 in a room. However, because the dispenser 100 can detect motion throughout a room by way of its multiple sensors, the dispenser 100 will still operate as intended. Indeed, the present dispenser provides a heretofore unknown advantage of removing any concern by a user in the proper placement of the dispenser my optimizing the number of sensors for the anticipated use of the dispenser so that a user need not be concerned with the orientation of the dispenser. In contrast, in a single sensor system, the user would have to be cognizant of the location of the optical sensor and be sure to position the single-sensor device with an appropriate orientation for observing an interior of the room.

Because the motion detection system allows the dispenser 100 to make observations about the entire perimeter of the dispenser 100, the housing 102 of the dispenser 100 is not required to include obvious or noticeable markings or other notations to assist a user in the correct orientation of the housing 102. Additionally, to maintain a relatively featureless, minimalist exterior of the housing 102, the housing 102 may be configured so as to hide the apertures 112 of the motion detector system from view by an individual standing nearby the dispenser 100.

Figure 37A:
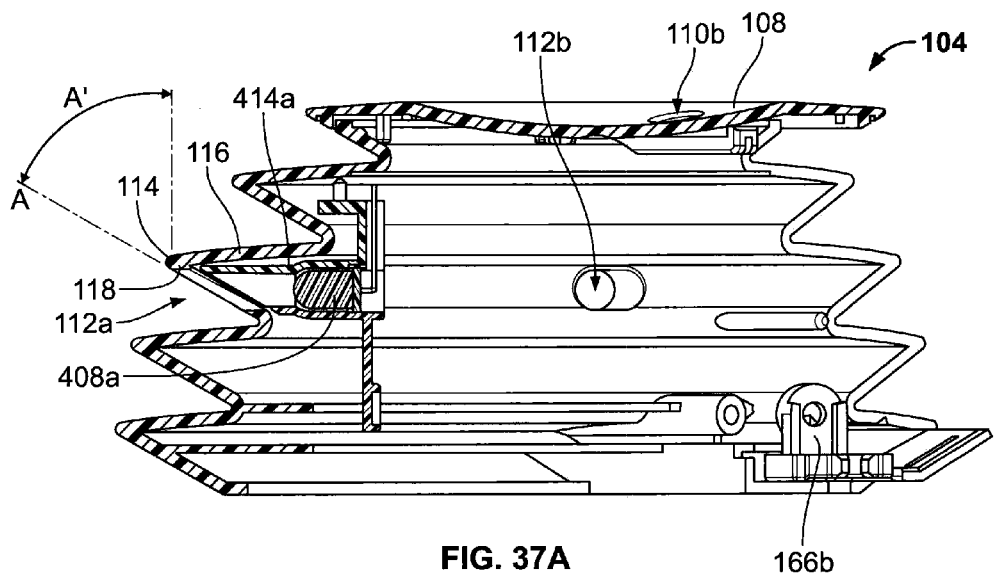
FIG. 37A is a sectional view taken through the aperture 112a of the top section 104 of the housing 102.

As shown in FIG. 1, for example, the apertures 112 of the motion detection system are formed within the lower face 118 of the fins 114 of the housing 102. By forming the apertures 112 on the lower face 118, the motion detection system can still observe movement through the apertures 112 of the housing 102, but the apertures 112 themselves are shielded from view by the upper face 116 of the fins 114. To illustrate this principle, FIG. 37A is a cross-sectional view taken through the aperture 112a of the top section 104 of the housing 102. The cylindrical tube 414a of the motion sensor 408a is positioned inwardly from the apertures 112a for observing movement through the aperture 112a. As illustrated, the aperture 112a is formed on the lower face 118 of the fin 114 of the housing 102. As such, the fin 114 provides an overhang that is positioned over the location of the aperture 112a. The overhang shields the aperture 112a from an observer's view, while also allowing the motion sensor system to observe the movement of objects. Such an arrangement adds to the aesthetic appeal of the dispenser 100 and also contributes to the clean look and feel of the device. As such, the geometrical arrangement of the fins 114, and the corresponding overhang defined by the lengths of the upper face 116 and the lower face 116 of the fin 114 can be selected to hide the apertures 112 from view.

As shown in FIG. 37A, the lower face 118 of the fin 114 defines a plane A extending away from the dispenser 100 at an angle A'. If an observer's line-of-sight is positioned below plane A, the observer may be able to view the aperture 112. If, however, the observer's line-of-sight is positioned above plane A, the observer will be unable to view the aperture 112, even though the motion detection system's view of the observer would be relatively unaffected (only the user's face would be obscured) and still capable of viewing the observer and detecting motion. Accordingly, the geometry of the fin 114 can be selected so that the apertures 112 will only be observable by a user that is sufficiently far away from the dispenser 100 so that the overall appearance of the dispenser 100 is not negatively affected.

Figure 37B:
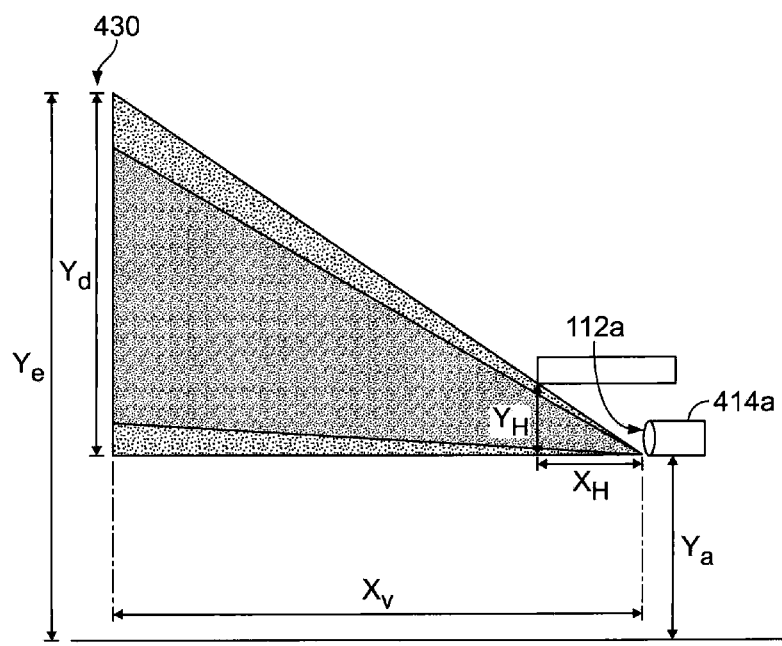
FIG. 37B is an illustration showing a representation of the aperture 112a of the dispenser 100 positioned nearby an observer.

FIG. 37B is an illustration showing a representation of the aperture 112a of the dispenser 100 positioned nearby an observer. In the arrangement, a bottom of the apertures 112 of the dispenser 100 are positioned a height above the ground surface of $Y_a$. Similarly, the eye 430 of an observer is positioned above the ground surface at a height $Y_e$. Accordingly, the observer's eye 430 is positioned above the bottom of the aperture 112 by a height $Y_e - Y_a = Y_d$. Additionally, the observer's eye 430 is a horizontal distance $X_v$ away from the aperture 112 of the dispenser 100. Accordingly, the observer's eye 430 will be able to observe the aperture 112 of dispenser 100 when the observer's eye falls below plane A defined by the fin 114 structure of dispenser 100. As shown in the figure, the angle A' of plane A is defined by the ratio of the length of the overhang of fin 114 ($X_H$) and the height of the overhang relative to a horizontal plane projecting from the bottom of the aperture 112a ($Y_H$).

Given a particular ratio of $X_H$ and $Y_H$ (and, consequently, angle A), the observer's eye 430 is able to view the aperture 112a when $X_v$ has a value greater than $Y_d$*TAN(A). If the observer 430 is closer, the observer 430 will be unable to view the aperture 112 as the observer's eye 430 will be positioned above plane A and the view of the aperture 112a will be blocked by the fin 114 of the dispenser 100. Using this mathematical relationship between the relative height of the observer and the distance of the observer away from the dispenser 100 it is possible to design the fin 114 of the housing 102 of the dispenser 100 so that in an average setting an observer will be unable to view the apertures 112 from a nearby distance.

In different settings, the value of $Y_e$ may vary greatly. A user could, for example, lay on the floor, in which case the user's eye's would be close to ground level. The value of $Y_e$ may also be relatively large if, for example, the user is positioned on a balcony or elevated floor overlooking the dispenser 100. Similarly, the user could be positioned on a stepladder so that the user is overlooking the dispenser 100, resulting in a relatively large value of $Y_e$.

Even though $Y_e$ may have many different values depending upon the details of a particular setting, it is possible to identify an average value of $Y_e$ that identifies a relatively accurate estimate of the actual height of a user's eye in a majority of settings. In one example, $Y_e$ is based upon the average height of an adult human that may observe dispenser 100. For example, $Y_e$ may be defined as encompassing the height range from the 1st percentile height for adult humans to the 99th percentile height for adult humans. Alternatively, $Y_e$ may be allocated a single distinct value, such as the average height of all adult humans.

Similarly, the height of the apertures 112 above the ground can vary based upon the particular setting. In some cases, the dispenser 100 will be positioned on a relatively low surface such as a low table, side table, or even the ground surface. Similarly, in other settings the dispenser 100 may be positioned on a relatively high surface such as a counter top, bar counter, or bookshelf. Even though $Y_a$ may have many different values, it is possible to identify an average value of $Y_a$ that identifies an estimate of the actual height of the apertures 112 above the ground. In one example, $Y_a$ is based upon the size of dispenser 100 and the average height of table and furniture surfaces within the home. In that case, the value of $Y_a$ may vary from 18 inches (45.72 cm) to 46 inches (116.84 cm). Alternatively, $Y_a$ may be allocated a single distinct value based upon the average height of surfaces within the home and the position of the apertures 112 within the dispenser 100 (e.g., 32 inches (81.28 cm)).

The value of $X_v$ may also vary greatly depending upon the setting. Again, though, it is possible to generate an average value of $X_v$ that will be relatively accurate for the majority of settings for the dispenser 100. In most homes, for example, the typical pathway for occupants of a room require that the occupants navigate through the room at a distance of approximately 5 feet (1.52 m) from the central furniture within the room, as well as the furniture positioned at the perimeter of the room. As a result, an observer of the dispenser 100 is likely to be positioned approximately 5 feet (1.52 m) from the dispenser 100. As such, in designing the dispenser 100, a viewing distance of approximately 5 feet (1.52 m) may be assumed.

Using the analysis described above, therefore, it is possible to deterministically design the housing 102 and, specifically, the geometrical configuration of the fin 114 defining the aperture 112 of the housing 102 to purposefully obscure an observer's view of the an aperture 112. To obscure the view of the aperture 112, the angle A' defined by the lower face 118 of the fin 114 is selected so that an observer's view of the aperture 112 is obscured at a predetermined threshold viewing, distance. To determine the desired angle A' for a given viewing distance, the height of the average observer is assumed to be 5' 8", which is identified as the average height of a human by The Measure of Man and Woman, Revised Edition—Human Factors in Design (Henry Dreyfuss Associates, 2002). Given the height of the average observer, the average height $Y_e$ of an observer's eye is 59.6 inches (151.38 cm). $Y_a$ is defined as the combination of the distance between a bottom end of the dispenser 100 and a lower end of the aperture 112 in addition to an average height of the dispenser off the floor, which, combined, totals 32 inches (81.28 cm). The minimum distance from which the observer can observe the aperture 112 ($X_v$) is selected to be 5 ft (1.52 m). With these conditions, the minimum angle A' of the face 118 of the fin 114 can be determined by solving the equation $A=TAN^{-1}((X_v)/(Y_e-Y_a))$ or, in this example, A'=TAN-1((60 inches)/(59.6 inches−32 inches)). As such, to meet the requirements of the 5 foot threshold distance, the geometrical structure of the fin 114 defining the aperture 112 is selected so that the angle of the lower face 118 of the fin 114 exceeds a minimum threshold angle of 65.3 degrees away from vertical (see angle A' illustrated on FIG. 37A).

Alternatively, the geometrical structure of the fin 114 defining the aperture 112 can be selected to comply with a desired view disruption index (VDI). The VDI for a particular dispenser 100 is defined as the ratio of $X_H$ to $Y_H$. To design the dispenser, therefore, a goal VDI is first calculated based upon the desired optical performance characteristics of the dispenser 100. Then, given that desired VDI, the geometrical configuration of the housing 102 of the dispenser 102 can be designed to either meet or exceed the desired VDI. For example, when considering a dispenser 100 positioned at an average height, it may be desired that the aperture 112 not be viewable by an average-height observer from distances less than 5 feet (1.52 m). To provide such a dispenser, a goal VDI is first calculated. The goal VDI for a given example installation of the dispenser 100 is defined as the ratio of the minimum distance from the dispenser 100 at which the observer will be capable of viewing a portion of the aperture 112 ($X_v$) to the height of the observer's eye above the bottom of the aperture 112 minus the height of the bottom of the aperture 112 above the ground surface (that is, $Y_a$). Accordingly, in this example, the goal VDI is equal to $(X_v)/(Y_e-Y_a)$, or (60 inches)/(59.6 inches−32 inches)=2.17. Given a goal VDI of 2.17, the geometrical arrangement of the fin 114 that defines the aperture 112 is configured so that the ratio $X_H$ to $Y_H$ for that fin 114 meets or exceeds the goal VDI.

Therefore, using either of the design methodologies described above, the outward appearance of the housing 102 of the dispenser 102 can be optimized for different anticipated installations of the dispenser 102. Using the first methodology, the angle A' of the lower face 118 of the fin 114 defining the aperture 112 is selected to exceed a particular threshold angle. Alternatively, rather than control the angle of the lower face 118, the second methodology can be utilized to determine the necessary overhang (i.e., the ratio of $X_H$ to $Y_H$) of the fin 114 for a particular installation.

For example, a dispenser 100 may be designed primarily for use by teenagers. In that case, the average observer of the dispenser 100 will be somewhat shorter than the average observer described in the example above. Consequently, the height of the average teenager's eye will be somewhat lower than that of the average adult's eye. Accordingly, using the first design methodology, for a dispenser directed toward use by a sixteen-year-old, the angle A' may be selected to exceed $TAN^{-1}((X_v)/(Y_e-Y_a))$, where $X_v$ is 5 feet (1.52 m), $Y_e$ is 62 inches (157.48 cm), and $Y_a$ is 32 inches (81.28 cm). As such, the angle of the lower face of the fin 112 encompassing the aperture 112 in a dispenser 100 designed for use by teenagers should exceed 63.37 degrees away from vertical (see angle A' on FIG. 37A). Alternatively, using the second design methodology, the VDI for such a dispenser should exceed $(X_v)/(Y_e-Y_a)$, or 1.99.

Alternatively, a dispenser 100 may be designed for use primarily in larger rooms. In that case, being in a larger room, the average distance of an observer from the dispenser 100 will be somewhat increased over the 5 feet (1.52 m) distance described above. Accordingly, using the first design methodology, for a dispenser directed towards use in a larger room, the angle A' may be selected to exceed $TAN^{-1}((X_v)/(Y_e-Y_a))$, where $X_v$ is 10 feet (3.05 m), $Y_e$ is 59.6 inches (151.38 cm), and $Y_a$ is 32 inches (81.28 cm). As such, the angle of the lower face of the fin 112 encompassing the aperture 112 in a dispenser 100 designed for use in larger rooms should exceed 77.05 degrees away from vertical (see angle A' on FIG. 37A). Alternatively, using the second design methodology, the VDI for such a dispenser should exceed $(X_v)/(Y_e-Y_a)$, or 4.35.

Alternatively, a dispenser 100 may be designed for use when positioned on coffee tables, or other low structures. In that case, the height of the bottom of the aperture 112 of the dispenser 100 above a ground surface could be reduced from the 32 inches (81.28 cm) described above. In that case, using the first design methodology, for a dispenser positioned on lower structures, the angle A' may be selected to exceed $TAN^{-1}((X_v)/(Y_e-Y_a))$, where $X_v$ is 5 feet (1.52 m), $Y_e$ is 59.6 inches (151.38 cm), and $Y_a$ is 25 inches (63.5 cm). As such, the angle of the lower face of the fin 112 encompassing the aperture 112 in a dispenser 100 designed for use on lower surfaces should exceed 60.03 degrees away from vertical (see angle A' on FIG. 37A). Alternatively, using the second design methodology, the VDI for such a dispenser should exceed $(X_v)/(Y_e-Y_a)$, or 1.73.

Alternatively, a dispenser 100 may be designed for use in bathrooms, where the dispenser is likely to be positioned on relatively high counter surfaces. In such an installation, though, the dispenser is likely to be viewed by an observer from a closer range than the 5 feet (1.52 m) described above. As such, the height of the bottom of the aperture 112 of the dispenser 100 above a ground surface may be increased from the 32 inches (81.28 cm) described above. In that case, using the first design methodology, for a dispenser positioned on higher structures, such as bathroom counters, where the dispenser is likely to be viewed from a relatively close position, the angle A' may be selected to exceed $TAN^{-1}((X_v)/(Y_e-Y_a))$, where $X_v$ is 3 feet (0.91 m), $Y_e$ is 59.6 inches (151.38 cm), and $Y_a$ is 46 inches (116.84 cm). As such, the angle of the lower face of the fin 112 encompassing the aperture 112 in a dispenser 100 designed for use on lower surfaces should exceed 69.3 degrees away from vertical (see angle A' on FIG. 37A). Alternatively, using the second design methodology, the VDI for such a dispenser should exceed $(X_v)/(Y_e-Y_a)$, or 2.65.

It is apparent, therefore, that the geometrical configuration of the housing 102 of the dispenser 100 and, specifically, the fin 114 defining the aperture 112 can be optimized for a number of different installations of the dispenser 100. Using either the first or second design methodology described above, the dispenser 100 can be designed so that the aperture 112 is obscured from view by a typical observer in that particular installation. As discussed above, the obscuring of the aperture 112 allows the dispenser 100 to have a more aesthetically pleasing outward appearance than in a dispenser where the aperture 112 would be readily observable. The different installation conditions may include placement of the dispenser 100 on a number of surfaces having differing heights. Example surfaces include tables, coffee tables, counter tops, side tables, and bathroom surfaces. Additionally, depending upon the installation, the typical observers may have different characteristics. Typical observers for a given installation may include standing adults, sitting adults, teenagers, or children. A particular installation may also dictate a typical distance at which the dispenser 100 is normally observed and, thereby, a minimum distance at which the aperture 112 of the dispenser 100 should be viewable. For normal rooms, the minimum distance may be set to approximately 5 feet (1.52 m). In larger rooms, the threshold distance may be as large as 10 feet (3.05 m), or even larger. In installations of the dispenser 100 in smaller rooms, such as bathrooms, kitchens, or laundry rooms, the distance may be smaller, for example 3 feet (0.91 m).

It is readily apparent, therefore, that given a particular target installation for the dispenser 100, a person of ordinary skill can use either of the two design methodologies provided above to optimize the design of the dispenser 100. For example, for a given installation, it is possible to calculate a target VDI for the dispenser 100 and then design the dispenser 100 to either meet or exceed that target VDI.

In the present implementation, detectors 408 include photo transistors. The photo transistors collect ambient light and allow a controller of the dispenser 100 to detect any changes in the intensity thereof. Filtering of the photo transistor output is undertaken by the controller (see, for example, controller 600 of FIG. 46E). If the controller determines that a threshold light condition has been reached, i.e., a predetermined level of change in light intensity has been received by the photo transistor over a short interval, the controller then determines whether to activate actuator drive system 200 to cause product to be dispensed from one of the containers 150 of the dispenser 100 based on whether certain conditions are met in light of an operational methodology.

The predetermined level of change in light intensity may comprise a high-to-low transition of light intensity and/or a low-to-high transition in light intensity. For example, if the dispenser 100 is positioned in a lit bathroom, a person walking past a sensor and who stands still within the sensory path may block a sufficient amount of ambient light from reaching the sensor over a first time interval to cause a signal to be developed indicating a high-to-low transition in light intensity. In the present scenario, however, the controller may not activate the dispensing device because a low-to-high transition in light intensity has not been received by the photo transistor during a second time interval, i.e., the person has not walked through the sensory path. As such, if the person were to continue walking through the sensory path within the second time interval, a low-to-high transition in light intensity would occur and cause the controller to activate the dispensing device. Depending upon the implementation, the controller may be triggered irrespective of whether a high-to-low transition occurs before or after a low-to-high transition in light intensity. Additionally, the detected first and second time intervals of the light intensity transitions may be within any time range. However, the first and second time intervals are generally selected to be of a sufficiently short duration so that light transitions over long periods of time, such as transitions that occur during the daytime and at dusk or dawn, will not cause the controller to activate the dispensing device.

Figure 38:
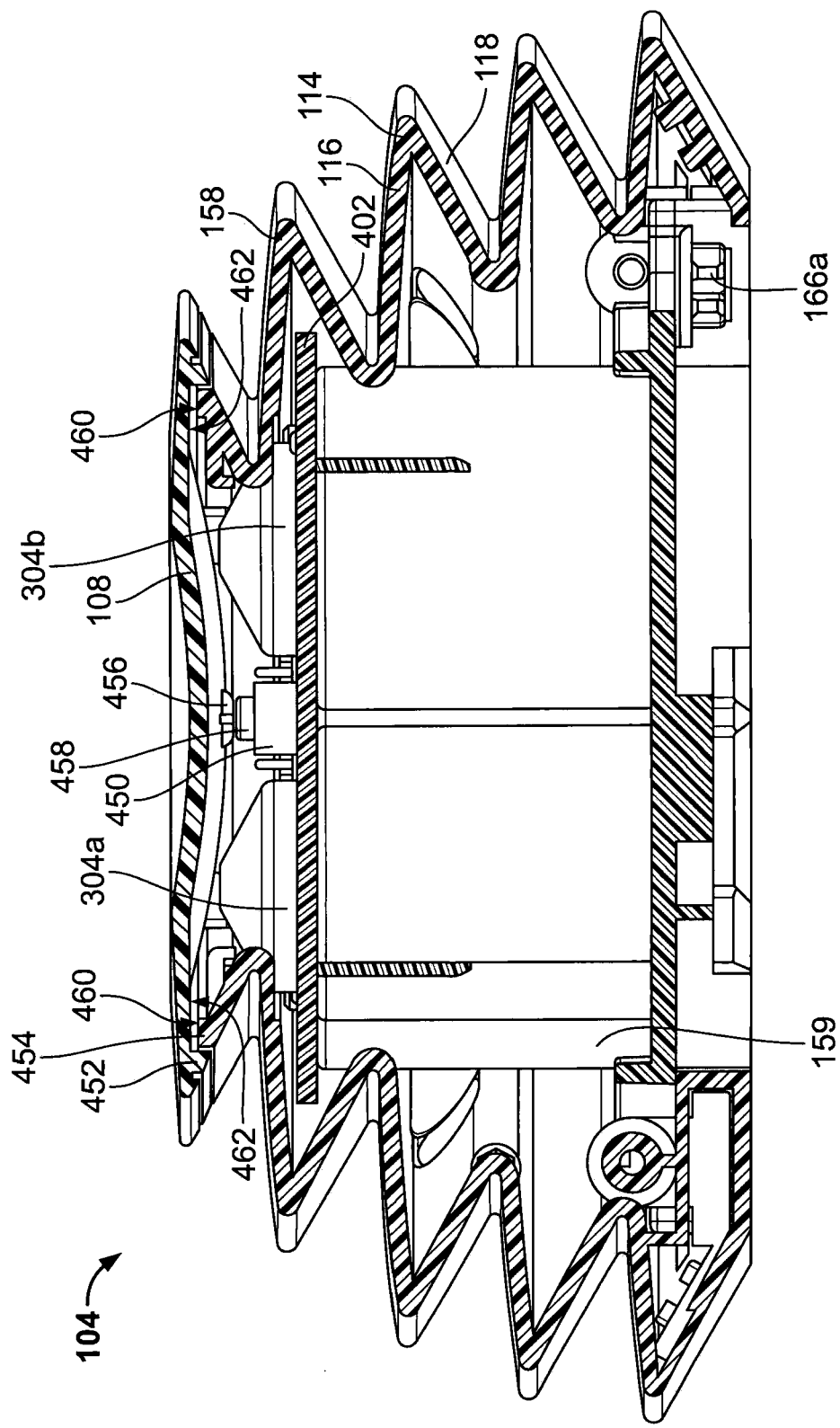
FIG. 38 is a cross-sectional view taken generally along the line 38-38 of FIG. 1 of a top section of a housing further including a top plate for actuating a switch.

The controller is also in communication with the top plate 108 of the top section 104 (shown in FIG. 1) that operates a button allowing a user to manually control the operation of the dispenser 100. FIG. 38 is a cross-sectional view taken along plane 29-29 of FIG. 1 showing top plate 108. As shown in FIGS. 1 and 38, the top plate 108 comprises a generally planar structure having a centrally concave region in which apertures 110a, 110b are formed. The top plate 108 is mounted over the sidewall 158 of the top section 104. The top plate 108 includes an annular wall 452 that projects downwardly from a bottom surface of top plate 108. The diameter of the annular wall defining an inner surface of the wall 452 is selected so that an inner surface of the wall 452 fits about an outer surface of a wall 454 formed at an upper portion of the sidewall 170. Both walls 452 and 454 have a circular geometry, with wall 452 fitting around wall 454. With this geometry, as shown in FIG. 38, the top plate 108 can be positioned over the sidewall 158 so that the wall 452 fits around the wall 454. Additionally, in this arrangement, the top plate 108 can be moved upwards and downwards, with the inner surface of the wall 452 moving past the outer surface of the wall 454.

The top plate 108 generally sits upon an upper surface of a switch 450, which is, in turn, mounted to the top surface of the PCB 402 and the controller of the dispenser 100. Specifically, a projection 456 extends downwardly from the bottom surface of the top plate 108 to contact pressure contact 458 of the switch 450. In FIG. 38, the pressure contact 458 is shown in its default non-triggered state. However, when sufficient force is applied to the pressure contact 458, it deforms downwardly to close a contact (or, in some implementations, opening a contact) within the switch 450 in a manner that is detectable by the controller. In one implementation, switch 450 includes a series TL1150 tact switch manufactured by E-Switch®.

In the present implementation, the user can approach the dispenser 100 from any direction around the dispenser 100 to activate the top plate 108, or any other user interface on the dispenser 100. The user can position the dispenser 100 in the home in any orientation to a wall or object that might block a lower button and still access and activate the top plate 108, or any other user interface device. In the present implementation, the positioning of the top plate 108 on the housing 102 proximate the apertures 110 is configured to provide a relatively high likelihood that the top plate 108 will not be blocked by objects in the environment of the dispenser 100. For example, a user is unlikely to block access to the apertures 110 and, thus, the top plate 108 as well. Additionally, the significant area of the top plate 108 allows the user to activate the dispenser 100 without having to brace the dispenser 100 or otherwise pick-up or manipulate the dispenser 100. Pushing down upon the top plate 108 of the dispenser 100 is unlikely to unseat the dispenser 100 from a flat, stable surface. The active surface of the top plate 108 varies between a 0.5" wide annular point of contact around a periphery of the top plate 108 to the entire surface area of the top plate, which has a 2.75" diameter. An average hand is 3" wide from pinky to index finger and 2" wide for three fingers. The size of the activation zone of top plate 108, therefore, affords a user the ability to use a single finger or an entire hand to activate the dispenser. This arrangement is configured to provide relatively easy and quick activation while passing by the dispenser 100, i.e., the user does not have to stop and orient their hand and/or finger to effectively activate the dispenser 100. This is particularly true in cases where small buttons may be provided on the side of a conventional dispenser housing.

Many prior art dispensers are also provided with manual activation buttons, which are located on a side surface of the dispenser. When a user presses such side mounted buttons, they must also typically secure the device with their other hand when pressing the button. Failure to do so may result in non-activation of the dispenser or undesired movement of the dispenser. Accordingly, for side-mounted button dispensers, two hands must generally be used to activate the dispenser. The present design of the top plate 108 allows a user walking by the dispenser 100 to easily activate the dispenser 100 via a manual operation. Given the size, shape, and position of the top plate 108 with respect to the remainder of the dispenser 100, the top plate 108 can be located quickly by a user. Additionally, because the top plate 108 is configured to activate the dispenser 100 by a downward force on the top plate 108, the top plate 108 can be easily activated by an entire hand, or by one or two fingers. The downward force exerted by a user's hand or fingers assists in preventing movement of the dispenser 100 during activation. As such, during manual activation, the present dispenser 100 does not require additional support from a user's hand to prevent movement of the dispenser 100. This characteristic is also aided by the placement of the center of gravity of the dispenser 100 into the bottom section 106 of the housing 102, e.g., by positioning a number of components of the dispenser 100 into the bottom section 106 as discussed above. Lowering the center of gravity of the dispenser allows for the bottom section 106 of the dispenser 100 to interact with a support surface to prevent movement. Therefore, when a downward force is applied to the top plate 108, e.g., a force parallel to a longitudinal axis of the dispenser 100 or a force angled with respect to such an axis, one or more of the configuration of the top plate 108 and the center of gravity of the dispenser 100 assists in preventing movement of the dispenser 100. These characteristics allow for use of the dispenser 100 without change to a user's regular routine as the dispenser 100 can be quickly and easily activated as the user walks by the dispenser 100.

In the configuration shown in FIG. 38, with the pressure contact 458 in its default position, the top plate 108 is raised away from sidewall 170 to allow for downward movement of the top plate 108. Accordingly, a user can apply a downward force to the top plate 108, thereby causing top plate 108 to move downwardly until a top surface 460 of the wall 454 contacts a bottom surface 462 of the top plate 108. The geometry of the walls 452 and 454 are selected, however, so that before the top surface 460 of the wall 454 contacts the bottom surface 462 of the top plate 108, the pressure contact 458 deforms to cause the switch 450 to trigger.

A user may generally displace the top plate 108 by applying a downward force anywhere on a surface thereof to activate the dispenser 100 to dispense product. Alternatively, the user may only displace or apply force to a peripheral portion of the top plate 108 to activate the dispenser 100. Further, it is contemplated that displacement of the top plate 108 about a peripheral portion or an interior portion may cause the top plate 108 to tilt and/or be downwardly depressed relative to the sidewall 158 to activate the switch 450. Depression and/or tilting of the top plate 108 causes the triggering of the switch 450 to activate the dispenser 100. It should also be contemplated that the presently described pushbutton system could be provided for activation or deactivation of the device or the changing of a mode or other operational characteristic of the device. In general, the top plate 108, in combination with the controller of the dispenser 100, may be utilized to allow a user to control or modify any operational methodology of the dispenser 100 suitable for control by the user. For example, the top plate 108 can be used to control the lockout period, the manual dispensing of product, which of the containers 150a, 150b are to be the primary containers from which product is dispensed, the amount of product to be dispensed upon each activation, whether one or more of the LEDs are to be illuminated during operation of the dispenser 100, and the like. In some cases, the top plate 108 incorporates an LED or other display device that is used to provide information to the user. For example, the information may comprise a current mode of operation of the device or that the device has detected an error condition, such as when the batteries 152 or the containers 150 need replacing. Alternatively, the top plate 108 may incorporate an LED or other display device to provide illumination for solely aesthetic purposes.

In other implementations, the push-button operation of the top plate 108 may be avoided by implementing top plate 108 as a capacitive sensing surface. In that case, to trigger the device, rather than displace or tilt the top plate 108 to trigger the switch 450, a capacitive sensing system may be incorporated into the top plate 108 in order to detect when a user has touched the top plate 108. Upon detecting a user's touch, the controller of the dispenser 100 can take appropriate action. In other implementations, touch capacitive sensing may be incorporated into any portion of the outer surface of the housing 100. As such, a user may be able to contact the housing 100 anywhere in order to provide a manual input to the dispenser 100.

Alternatively, the dispenser 100 may include a pressure switch positioned at the bottom of the housing 102 of the dispenser 100. In that case, to trigger the pressure switch, a user presses down anywhere upon the housing 102. As the housing 102 moves downward, the pressure switch is pressed upon by the surface upon which the dispenser 100 is positioned. When the downward pressure exceeds a predetermined threshold, the pressure switch is triggered and the dispenser 100 can respond appropriately to the user input. In such an implementation, the pressure threshold for the pressure switch exceeds the pressure generated by the weight of the dispenser 100 when sitting upon a surface without any additional downwards force being supplied by a user against the housing 102.

Upon the triggering of the switch 450, the controller can detect that a user has compressed the top plate 108 and can take appropriate action based upon the current operational mode of the dispenser 100. The appropriate action may involve causing the actuator drive system 200 to immediately, or accordingly to a delay, dispense product from one of the containers 150a, 150b, change a mode of operation of the dispenser 100, or to do nothing, if, for example, the dispenser 100 is in a stop state.

Figure 39:
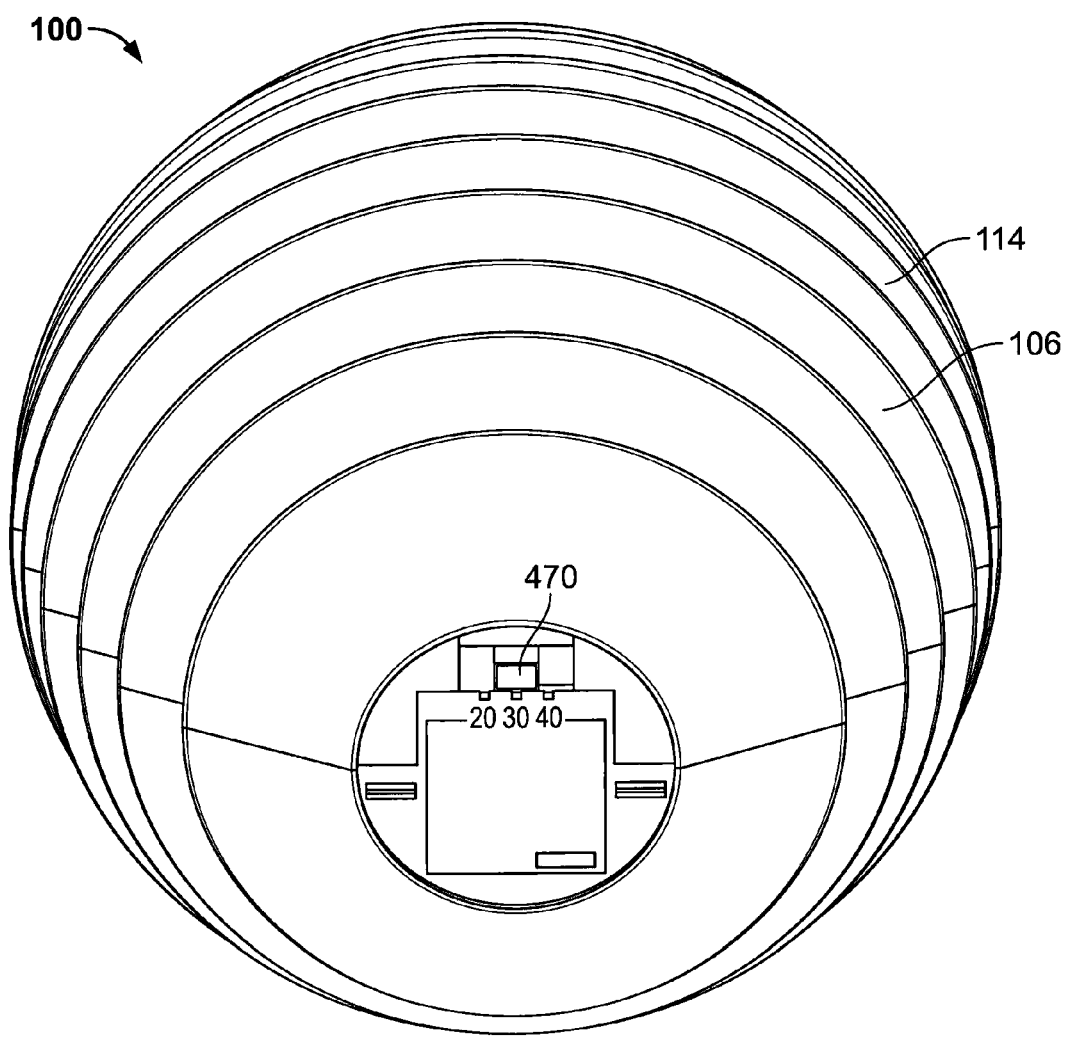
FIG. 39 is a bottom isometric view of a dispenser showing a mode selector switch.

The controller of the dispenser 100 is also in communication with a mode selector switch 470. FIG. 39 shows the mode selector switch 470 mounted to a bottom surface of the bottom section 106 of the housing 102. The mode selector switch 470 can be used to select a lock-out period that defines a minimum frequency with which dispenser 100 can dispense product. This lock-out period can be used, for example, to minimize an amount of fragrance product that can be dispensed into a particular area over a given period of time. In one implementation, the selector switch 470 is a toggle switch movable to one of three stable positions.

Accordingly, the controller of dispenser 100 can use a combination of input signals from detectors 408, top plate 108, and selector switch 470 to control the operation of the dispenser 100. Various modes of operation of dispenser 100 are illustrated in detail by the timing diagrams illustrated in FIGS. 40-43.

Generally, upon activating the dispenser 100, the device undergoes a short delay prior to activating the motion sensors and checking the lock-out period duration designated by the switch 470. The delay allows the user to complete the process of attaching the top section 104 and the bottom section 106 and allows the dispenser 100 to ignore errant presses of the top plate 108 while the top section 104 is being connected to the bottom section 106. Additionally, the delay period allows the electrical systems of the dispenser 100 to stabilize after power is initialized. The lock-out period may be modified or eliminated entirely in other embodiments. Thereafter, the motion sensors are active for detecting motion in a manner as described above. Additionally, the dispenser 100 may enter a lock out mode lasting a time duration equal to that of the selected time interval of the switch 470.

During the lockout mode, motion detected by one or more of the sensors may be registered by the dispenser 100, but no product dispensing operation is undertaken. Instead, an LED may be illuminated for a duration of the motion detected. In other embodiments, though, a single flash of one or more LED's may be undertaken, various flashing sequences of one or more LED's may be undertaken, or there may be no LED. For example, in one implementation the LED or LEDs are illuminated using a 2 second fading on and off sequence in which the LED or LEDs fade up to full intensity in 1 second and then fade down to off in one second. In that case, any motion activity detected during the fading-down time will be registered by the controller of dispenser 100 but is not displayed by the LED or LEDs. During the lockout mode a product dispensing operation may be initiated at any time by manual displacement of the top plate 108.

In one embodiment, upon initial activation of the dispenser 100, and completion of a 0.1 ms delay, the dispenser 100 may also undergo a 0.4 ms delay in which any displacement of the top plate 108 is not registered to cause a spraying operation. This time period may also be modified or eliminated in other embodiments. Thereafter, displacement of the top plate 108 may be registered to cause a product dispersal operation from one or more of the containers 150a and 150b.

If both containers 150a and 150b are present within the device, the device will select the appropriate container to dispense fluid from based on a timing sequence. In the present embodiment, the dispenser 100 operates in alternating 24 hour sequences in which product from a first container 150a is dispensed within the first 24 hour sequence in response to the detection of motion or displacement of the manual pushbutton and fluid from the second container 150b is dispensed within the second 24 hour sequence in response to detection of motion or the displacement of the manual pushbutton. These sequences thereafter alternate in 24 hour increments between containers 150a and 150b. Upon determining which sequence dispenser 100 is in, a product dispensing operation is undertaken using the appropriate container.

In other implementations, the timing sequences may occur according to any schedule. For example, the sequences may occur hourly, in which every hour a different container 150 is selected for the dispensing of product. Alternatively, the timing sequences may be adjusted throughout the day. For example, from 8 am to 6 pm the sequence switches in an hourly routine. But from 6 pm to 8 am the sequence switches every 4 hours. Additionally, the sequences may be modified based upon information received from the dispenser 100's sensor systems. For example, during time periods where optical sensors detect light levels exceeding a particular threshold (indicating daylight), the sequence may switch every hour. During time periods where optical sensors detect light levels that fall below a particular threshold (indicating nighttime), the sequence may be switched every 5 hours. In one preferred implementation, the sequence switches every 24 hours, allowing each container 150 to be the primary container 150 for a continuous 24-hour period, unless switched earlier by the user via a manual user input. At the conclusion of a 24 hour period, the non-primary container 150 becomes the primary container 150 and product dispersal events occurring during that 24 hour time period cause product to be dispensed from the primary container 150 for that 24 hour time period. In one implementation, the sequence alternates every time dispenser 100 dispenses product from one of containers 150 to ensure that the fragrance being dispensed remains novel to the user.

In another preferred embodiment, the timing sequences are preferably between 1 hour and 1 month, or alternatively between 12 hours and 2 weeks, or alternatively 24 hours. Indeed, the timing sequences may be 24 hours, one week, two weeks, one month, or any time period greater than 24 hours. In other embodiments, the timing sequences are measured in one or more days, alternatively one or more weeks, or alternatively one or more months. The timing sequences may be the same or may be different. In a first example, each of the timing sequences is 24 hours. In another example, the first container is the primary container for 2 days that correspond to the days of the weekend and the second container is the primary container for 5 days that correspond to the days of the work week. In some embodiments, the length of the timing sequences may be equal to the length of the lockout period as discussed in more detail below. For example the length of the timing sequences may range from 1 to 180 minutes.

The same timing sequences may be utilized for dispensers including more than two containers. Alternatively, dispensers having more than two containers may incorporate additional timing sequences. For example dispensers including three containers may incorporate first, second, and third timing sequences, dispensers including four containers may incorporate first, second, third, and fourth timing sequences, and so on. Further, dispensers including any number of containers may incorporate any number of timing sequences.

In some embodiments, different containers are selected for dispensing product based upon a current time of day. For example, if one of the containers 150 contains a product providing a "fresh" smell, that container is dispensed during the day, while another container 150 containing a relaxing scent (e.g., lavender) is dispensed in the evening. Furthermore, during different times of day, differing amounts of product may be dispensed. In the morning, for example, larger amounts of product may be dispensed, while in the evening, smaller and more subtle amounts of product are dispensed. In some cases, if the dispenser 100 detects a significant amount of traffic, e.g., a stream of users enters a room within a 2 hour period, which causes the motion-detection algorithm to recognize a heavy user flow, the dispenser 100 is configured to dispense a larger amount of product either by dispensing more product on each dispensing occasion, or by reducing the lockout period, described below. Further, the dispenser may also be programmed to dispense a more active or "fresh" small during such time periods. Alternatively, if the dispenser 100 detects an extended period of time over which no or limited user traffic is detected, the dispenser 100 may initiate a dispensing sequence based upon diminished use, e.g., by dispensing a lavender or calming scent, regardless of the time of day, or by dispensing less product.

During product dispensing operations in response to the displacement of the top plate 108, the user's interaction with the pushbutton may affect the type of product dispensing operation undertaken. If a user depresses the top plate 108 for a duration less than a certain period of time "T", no spraying operation is undertaken. If a user depresses the pushbutton for a duration equal or greater than the time period "T" then one spraying operation is undertaken for a period "P". However, if a user displaces the pushbutton two times within a specified interval "SI", the 24 hour timing sequence is re-set to zero, the sequence is alternated to the alternative sequence having a different container, and the spray operation for the period "P" is undertaken with the new container.

If the lockout period for the dispenser 100 has expired, the dispenser 100 is responsive to both sensory input and the manual activation of the top plate 108. During this active mode of operation, the detection of motion will cause the dispenser 100 to undergo the same inquiry as previously described to determine which container to immediately spray from. More specifically, if no container is present within dispenser 100 a product dispensing operation is not undertaken. If only one container 150 is present in the device, then a dispensing operation is undertaken with the available container. If both containers 150a and 150b are present, the device will select the appropriate container to dispense product from based on a timing sequence.

The operational steps to activate and dispense product from either container may be the same regardless of whether a product dispensing operation is initiated in response to sensory input or the displacement of the manual pushbutton. Upon determining which container to spray from, the dispenser 100 drives the actuator drive system 200 to lift the appropriate armature to lift the container for a time period "A." Thereafter, the actuator drive system 200 is stopped for a time period "B" while product is dispensed from the appropriate container. Finally, actuator drive system 200 is driven in reverse for a time period "C" to lower the container back to a pre-actuation position. The same sequence occurs regardless of which container is activated. The time periods A, B, and C may comprise any appropriate periods of time. Further, in alternative embodiments one or more of the periods may be eliminated. Still further, in other embodiments the time periods are different depending on the container undergoing the spraying operation or the contents thereof.

Every time the pushbutton is depressed by a user to dispense product or any sensory input causes the activation of the device, the lockout period timer is re-set to zero and the dispenser 100 is placed into the lockout mode for the duration of the lockout period, which is dependent on the position of the user control adjustment switch 470, as described above. The user may displace top plate 108 to initiate a spraying operation as often as desired, whereupon the lockout period timer is re-set to zero and the device enters a new lockout period after each successful use of the top plate 108. Further, if a user adjusts the switch 470 during any stage of the operational use of the device, the lockout period can be immediately modified to reflect the new period without re-setting the period. In a different embodiment, adjusting the switch during use of the device both modifies the lockout period duration and also re-sets the lockout period timer to zero.

The dispenser 100 is configured to terminate power for initiating spraying operations via the actuator drive system 200 and the activation of the LED 416 if the battery life has depleted to a predetermined level.

In general, any time setting, range, period, or interval for any switch or operational step of the present dispensing device may comprise any value. It should also be assumed that the values may differ between the first and second sequences, between lockout and active modes, between sensor-activated sprays and pushbutton sprays, etc. It should also be assumed that in other embodiments any of these values could be altered by a user or preprogrammed.

FIGS. 40-43 provide various timing diagrams to better describe the operation of particular embodiments of the dispenser 100.

Figure 40:
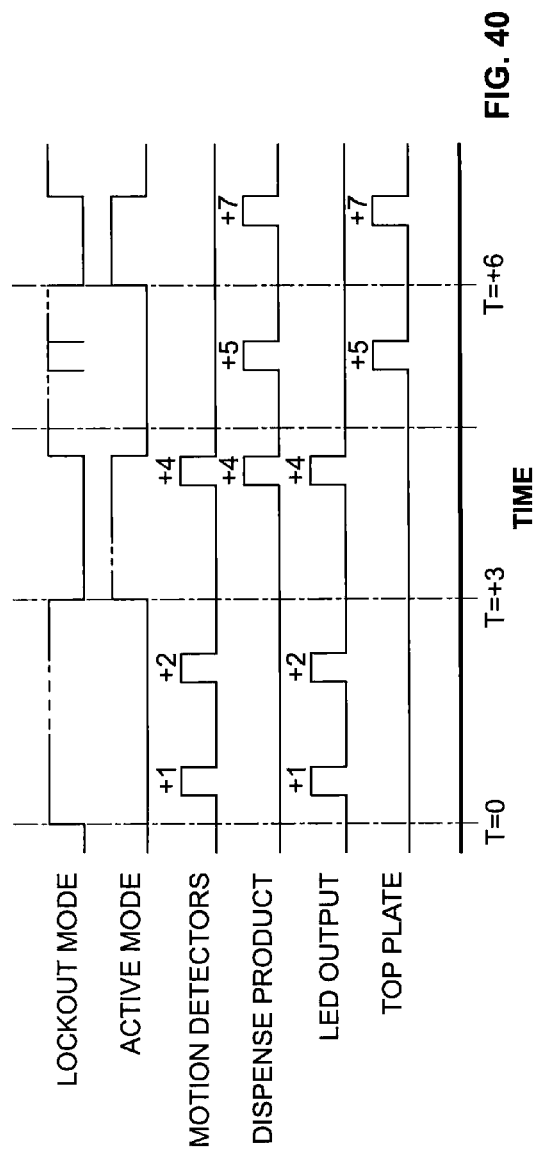
FIG. 40 depicts a timing diagram of one embodiment illustrating operation of the dispenser and interaction between components of the dispenser.

FIG. 40 depicts a timing diagram of the present embodiment that illustrates operation of the dispenser 100 during use and interaction between the motion detectors, LED output, top plate, and product dispersal system. At time t=0 the dispenser 100 is powered up. This may occur, for example, when the top section 104 and the bottom section 106 of the housing 102 are locked together causing battery contacts 410a and 410b of cap assembly 168 to contact batteries 152a, 152b disposed within the bottom section 106. Immediately upon activating the dispenser 100, the dispenser 100 may undergo a 0.1 ms delay prior to activating motion detectors 408 and determining the lockout time indicated by the selector switch 470. This time period may be modified or eliminated entirely in other embodiments. Thereafter, the motion sensors are active for detecting motion. After powering up, the dispenser 100 is configured to immediately enter a lock-out period. During the lock-out period the dispenser 100 does not dispense product when the dispenser 100 detects movement. Accordingly, even though motion is detected by one or more motion detectors at times t=+1 and t=+2, the output 'dispense product' stays low, and no product is dispensed by the dispenser 100. Notably, even though the dispenser 100 is not in active mode at times t=+1 and t=+2, the LED 416 is illuminated upon the input from the motion detectors being high. In some cases, a single flash of one or more LED's may be undertaken, or various flashing sequences of one or more LED's may be undertaken when motion is detected. Alternatively, the dispenser 100 may not include an LED. During a lockout mode the only way to initiate a spraying operation is by manual displacement of the pushbutton.

At time t=+3, the lockout period expires. The duration of the lockout period is selected by a user via the selector switch 470. It is preferable that the lockout period has a duration of between about 1 to about 180 minutes, and more preferably between about 10 to about 60 minutes, and most preferably between about 15 to about 40 minutes. In one embodiment, the three position switch is used to select between 20, 30 and 40 minute lockout periods. In another embodiment, the switch is used to select between 15, 20, and 30 minute lockout periods, though other time periods may be used. After the lockout period expires, the dispenser 100 enters an active mode. Accordingly, if the controller of the dispenser 100 detects movement, product will be dispensed. Alternatively, rather than being selected by a switch having a limited number of positions, a user may use an alternative user input device, such as a touch surface, keypad, or other user input device to select a particular lockout period. In that case, the lockout period may have any value that a user chooses to select. Additionally, the lockout period may be adjusted throughout the day. For example, during a first time period (for example, 8 am through 6 pm), the lockout period could have a first value selected by a user, or a value that is a multiple of a user-selected value. For another time period (for example, 6 pm through 8 am), the lockout period could have a second value selected by a user, or a value that is a second multiple of a user-selected value. Alternatively, the lockout period could be consistently modified and updated based upon a history usage of the dispenser 100. If, for example, a user is consistently using the manual input to cause the dispenser 100 to dispense product (indicating that the dispenser 100 is not dispensing often enough for the user), dispenser 100 could autonomously shorten the length of the lockout period in order to dispense additional product, minimizing the need of the user to regularly rely on the manual input to cause product to be dispensed. The lockout period could also be adjusted based upon sensor input to dispenser 100. For example, during time periods where optical sensors detect light levels exceeding a particular threshold (indicating daylight), the lockout period could have a first value. During time periods where optical sensors detect light levels that fall below a particular threshold (indicating nighttime), the lockout period could have a second value. Further, the lockout period could be adjusted based on a sensed level of room usage, e.g., if a pattern is recognized that there is a heavy flow of traffic through a room the lockout period could be reduced and if a pattern is recognized that there is a light flow of traffic through the room the lockout period could be increased. In one preferred implementation, though, the user selects a particular lockout period using the switch 470, as described above.

For the various implementations of the lockout period, numerals may be displayed on the housing 102 to indicate the length of a lockout period associated with each position of the switch 470 (as shown in FIG. 39). Alternatively, the indications may be graphical, for example, by displaying a short line besides a first switch 470 position, a longer line besides a second switch 470 position, and a longest line besides a third switch 470 position, indicating short, medium, and long lockout periods, respectively).

At time t=+4, the motion detectors of the dispenser 100 detect movement, the LED 416 is illuminated and product is dispensed. After the product is dispensed, the dispenser 100 again enters a new lockout period and enters a non-active mode.

During this lockout period, at time t=+5, the user operates the top plate 108 to manually cause the dispenser 100 to dispense product. After dispensing product in response to the user's activation of the top plate 108, the dispenser 100 enters a new lockout period.

At time t=+6, the lockout period expires, and the dispenser 100 again enters active mode. At time t=+7 the dispenser 100 detects that the user has operated the top plate 108 to manually cause the dispenser 100 to dispense product. After dispensing product in response to the user's activation of the top plate 108, the dispenser 100 enters a new lockout period.

Figure 41:
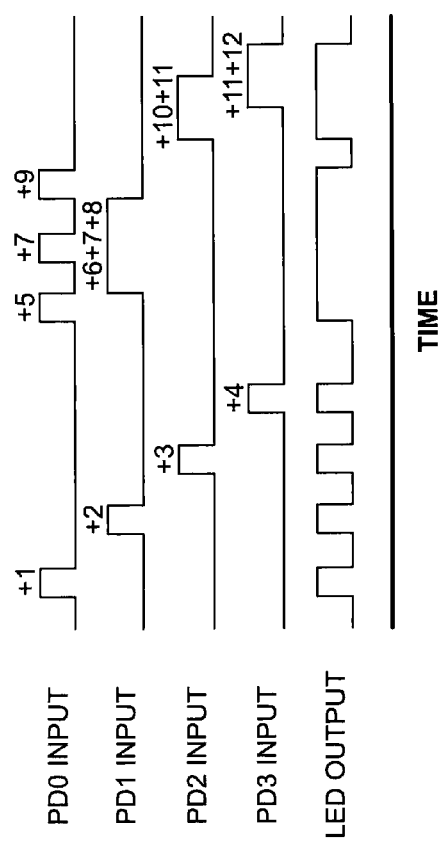
FIG. 41 depicts a timing diagram of one embodiment illustrating the interaction between each of the four motion detectors of the dispenser.

FIG. 41 depicts a timing diagram of the present embodiment that illustrates the interaction between each of the four motion detectors of dispenser 100 (designated PD0-PD3 in FIG. 41) and the output state of LED 416. As shown by FIG. 41, the output of LED 416 matches that of the input of motion detectors PD0-PD3. Accordingly, when any of the motion detector inputs goes high, the output to LED 416 will go high (that is, LED 416 will be illuminated). Additionally, should the input of multiple combinations of multiple motion detectors go high at the same time, the output of LED 416 will go high for the duration of the time period during which at least one motion detector input is high. With reference to FIG. 41, therefore, at any of times t=+1, +2, +3, or +4, when the input from motion detectors PD0, PD1, PD2 and PD3 go high, respectively, the output to LED 416 goes high. Similarly, when multiple motion detector inputs go high at the same time (such as at times t=+7 and +11), the output to LED 416 goes high. In other situations, where the input of different ones of motion detectors PD0-PD3 go high at different times, the output of LED 416 is similarly held high. This situation occurs at time t=+5 though t=+9, where input PD0 initially goes high and as input PD0 goes low, input PD1 goes high. Similarly, at the transition from t=+8 to t=+9, input PD1 goes low while input PD0 goes high. Accordingly, from time t=+5 though t=+9 the output of LED 416 is held high.

A similar situation occurs from time t=+10 to +12. At time t=+10 input PD2 is high. At time t=+11 input PD3 goes high so that both inputs PD2 and PD3 are high. At time t=+12, input PD2 goes low, but input PD3 remains high. Accordingly, from times t=+10 to t=+12 the output to LED 416 remains high.

Figure 42:
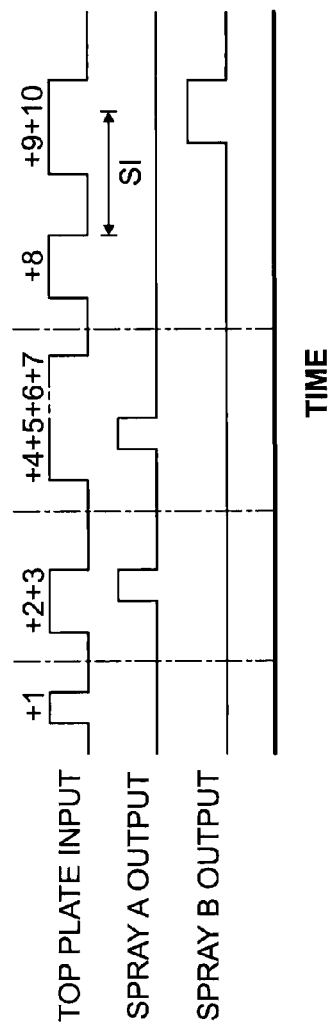
FIG. 42 depicts a timing diagram of one embodiment illustrating manual user input to the dispenser and container selection.

In some cases, the top plate 108 is configured to detect a particular user input for controlling whether product is dispensed from the first container 150*a* or the second container 150*b* of the dispenser 100. For example, depending upon a number of presses, a duration of the press, or a time of day that the user uses the top plate 108, the controller of the dispenser 108 may select a different one of the containers 150*a*, 150*b* from which to dispense product. FIG. 42 depicts an example timing diagram of the present embodiment that illustrates one possible interrelationship between the user's manipulation of the top plate 108 and the controller's selection of which container 150*a*, 150*b* to use.

As shown in FIG. 42, at time t=+1 the user presses and releases the top plate 108. However, the duration of the press does not exceed a predetermined minimum time duration threshold and dispenser 100, consequently, ignores the press and takes no action. At time t=+2, the user users presses and holds the top plate until time=+3. The controller of the dispenser 100 determines that the duration of this top plate 108 press exceeds the minimum threshold and dispenses product from the first container 150*a*. Later, the user initiates another press for the duration of times t=+4 through t=+7. During this press, the controller of dispenser 100 determines that the user has pressed the top plate 108 for a sufficient duration as of time t=+5 and dispenses product from the first container 150*a* at that time. Here, the controller takes no further action even though the user holds the top plate 108 for an extended duration of times t=+6 and +7.

Later, at time t=+8 the user presses the top plate 108 for a short time duration that satisfies the time threshold for dispensing product. However, within a specified time interval 'SI', the user again presses top plate 108, this time for the time periods t=+9 and +10, which also exceeds the minimum threshold for a successful press of the top plate 108. In this case, because there was a prior press that occurred within the specified interval prior to the press occurring during time periods t=+9 and +10, the controller dispenses product from the second container 150*b* rather than the first container 150*a*. At this time, the dispenser 100 may cause the second container 150*b* to become the primary container from which to dispense product at future product-dispensing events. This operation allows the user to manually dispense product from either container 150 using a straight-forward interaction with the dispenser 100. If, for example, one container 150*a* contains fragrance, while the second container 150*b* contains an odor eliminator, the user can easily control which product is to be dispensed.

Accordingly, by performing a single press of the top plate 108 for a duration that exceeds a minimum threshold, the user can cause the dispenser 100 to dispense product from a first container 150 stored therein. Alternatively, by performing two presses that occur within a maximum time threshold (the specified interval (SI)), the user can cause dispenser 100 to dispense product from a second container 150 stored therein.

Figure 43:
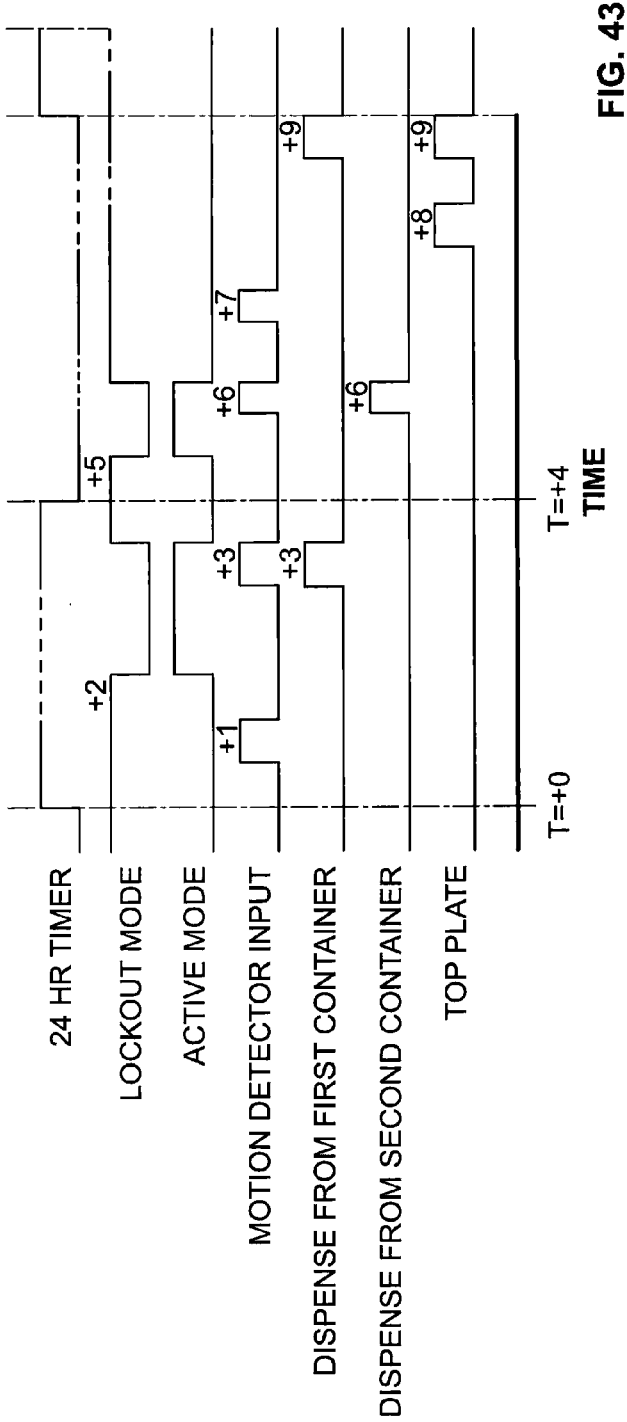
FIG. 43 depicts a timing diagram of one embodiment illustrating an operational methodology of the dispenser over multiple timing sequences.

FIG. 43 depicts an example timing diagram of the present embodiment that illustrates the operational methodology of the dispenser 100 over multiple 24 hour time periods. During a first 24 hour time period, a first container 150*a* is selected as the primary container from which to dispense product, while a second container 150*b* is selected as a secondary container. In the following 24 hour time period, though, the primacy of containers 150*a* and 150*b* is reversed and container 150*b* becomes the primary container from which to dispense product. In the following 24 hour time period, the primacy of the containers is again reversed, and so on. In a different embodiment, the dispenser may switch between the first timing sequence, in which the first container is activated, and the second timing sequence, in which the second container is activated, immediately following the activation of the first container. Subsequent activations of the containers may alternate between the first and second containers in a similar manner.

As shown in FIG. 43, at time t=+0 dispenser 100 enter an initial lockout period and enters an inactive state. At time t+=1, during the lockout period, motion is detected. Because the dispenser 100 is in lockout mode, the dispenser 100 takes no action.

Later, at time t=+2 the lockout mode expires and the dispenser 100 enters an active mode. At time t=+3 motion is detected and the dispenser 100 causes product to be dispensed from the primary container for that time period. As time t=+3 resides within the first 24 hour period, product is dispensed from the first container 150*a*. Upon dispensing product, the dispenser 100 again enters a lockout period.

At time t=+4 a second 24 hour period is entered. For the second 24-hour period the second container 150*b* is selected as the primary container from which to dispense product.

Later, at time t=+5 the lockout period expires and dispenser 100 enters an active mode. At time t=+6 motion is detected and dispenser 100 causes product to be dispensed from the primary container for that time period. As time t=+6 resides within the second 24 hour period, product is dispensed from the second container 150*b*. Upon dispensing product, the dispenser 100 again enters a lockout period.

At time t=+7 motion is again detected. However, the lockout period is still active and, as dispenser 100 is not operating in active mode, dispenser 100 takes no action.

At times t=+8 and +9 the user issues two presses to top plate 108. The two presses occur within the specified interval (SI) for double presses. As such, at time t=+9 the dispenser 100 dispenses product from the secondary container for that 24 hour time period. Accordingly, product is dispensed from the first container 150*a*. In some implementations, though, the double press of top plate 108 causes the dispenser 100 to toggle the primacy of containers 150*a* and 150*b* to mimic the change that occurs at the completion of each 24 hour period. Or, alternatively, the double press causes the dispenser 100 to reset the 24-hour counter and immediately enter the next 24-hour cycle (effectively forcing the primacy of container 150 to switch just before dispenser 100 dispenses product). Accordingly, the double press of the top plate 108 can force the dispenser 100 to prematurely complete the current 24-hour period.

In some implementations, the dispenser 100 includes detection mechanisms to determine whether one or more containers 150 are present within housing 102. If a particular container is not present, during a product dispensing operation the dispenser 100 may instead attempt to dispense product from the other container. If neither container 150 is present, the dispenser 100 may enter an error state until at least one container has been disposed within the dispenser 100. The error state may involve displaying a message for a user to insert at least one container 150 into the dispenser 100.

Figure 44:
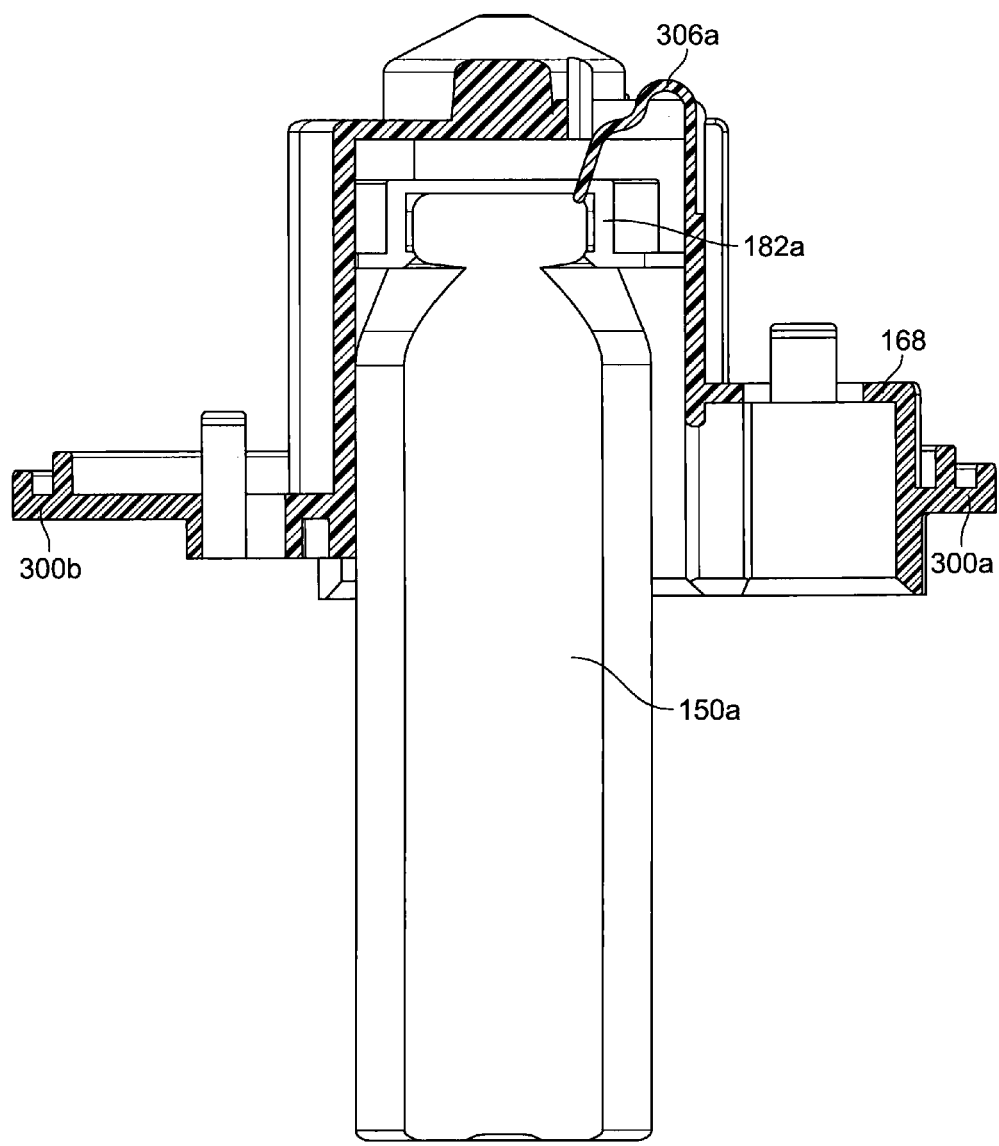
FIG. 44 is a cross-sectional view taken generally along the line 44-44 of FIG. 19 showing a container detection arm of the dispenser.

FIG. 44 is a cross-sectional view taken generally along the plane 44-44 of FIG. 19 showing cap assembly 168, container 150*a* and container detection arm 306*a*. Container detection arms 306*a* and 306*b* (see FIG. 19) comprise arms or levers that penetrate through cap assembly 168 into the volume defined by apertures 160*a*, 160*b* to detect the presence of containers 150*a*, 150*b*. Top portions of the container detection arms 306 are visible in the top view of cap assembly 168 shown in FIG. 19.

Upon a user inserting a container into the top section 104 of the dispenser 100 (usually by locking the top section 104 to the bottom section 106, as described above), a user aligns the top section 104 of the housing 102 with the bottom section 106, as described above and illustrated in FIGS. 22-24. During and/or upon completion of the seating of the top section 104 onto the bottom section 106, the upper end of each container 150 contacts its respective container detection arm 306 and displaces same when a portion of the container and/or the container's sheath interacts with the detection arm 306.

Container detection arms 306 comprise arms or levers, whereupon upward movement of the containers allow the detection arms to undergo flexure or displacement to press a corresponding switch located on the PCB 402 to indicate the presence of a container 150*a*, 150*b* in the respective aperture 160*a*, 160*b*. In other embodiments, the detection members may comprise a lever and/or a switch. Further, other embodiments may utilize non-flexible levers or members to depress the switches. Still further, container 150*a*, 150*b* may directly impact a switch or block an optical sensor during or upon completion of the seating of the top section 104 to the bottom section 106. In other embodiments, the detection arms do not register the presence of a container until the top section 104 has been rotatably secured to the bottom section 106. Other container-detection mechanisms include magnetic field sensors (for example, hall-effect sensors), capacitive or inductive field sensors, or more advanced systems using a radio frequency (RF) or magnetic communication between the dispenser 100 and the containers 150 using, for example, radio frequency identification (RFID) or Bluetooth technologies.

During operation of the dispenser 100, input from the switches coupled to the container detection arms 306 may be used to determine whether one or more containers are installed and affect an operating methodology to prevent attempted dispensing of product from a container that is not present. Accordingly, the dispenser 100 is self-configuring between a dual-container dispensing operation and a single-container dispensing operation. If the user elects to only install a single container 150 into the dispenser 100, the dispenser 100 detects that condition and operates using the single container 150 only. The dispenser 100 will similarly detect when no containers 150 are installed and will not run the motor to spray, thus saving battery life. Even when no containers 150 are present, however, the dispenser 100 may continue to detect motion and register that motion via the LED. This behavior notifies the user that the dispenser 100 is operating correctly, but that no product is being dispensed due to the lack of containers 150.

As described above, the electronic components of the dispenser 100 are placed in electrical communication with one another when the top section 104 is connected to the bottom section 106. When the two sections are connected, electrical energy from the batteries 152*a*, 152*b* is communicated from terminals disposed within the top of apertures 162 and the bottom of apertures 122 to the appropriate components of the dispenser 100. The electrical energy can be used to power various systems such as the controller of dispenser 100, motor 202 of actuator drive system 200, LED 416, or motion detectors 408. Additionally, the electrical energy can be supplied to a number of switches or sensors to detect a state of various components of the dispenser 100 such as contact switch 450, selector switch 470, contact switches proximate to container detection arms 306, or (when constructed as passive elements) motion detectors 408.

Each element of the dispenser 100 may be connected to the controller and power supply of the batteries 152a, 152b using a varying number of electrical interconnections.

Figure 45A:
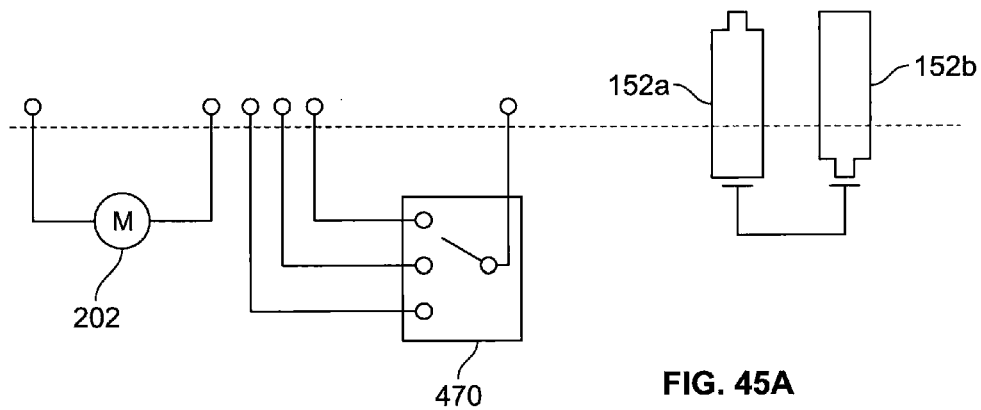
FIGS. 45A-45C illustrate various electrical interconnection arrangements between a motor, actuator drive system, selector switch, and power source of the dispenser.

FIG. 45A, for example, illustrates a conventional electrical interconnection arrangement with the motor 202 of the actuator drive system 200, the selector switch 470, and the batteries 152. In the depicted conventional arrangement, this requires 6 electrical contacts between the various contacts —2 connections for the motor 202 and 4 connections for the switch 470. The 4 connections for the switch 470 comprise a single input connection to the switch 470 with three output connections reflective of each of the three possible values of the switch 470. In that arrangement, a reference voltage value can be inputted to the input of the switch 470 and each of the output terminals can be monitored for that reference voltage value. By determining the output terminal upon which the reference voltage is detected, the controller can identify a position of the selector switch 470.

Figure 45B:
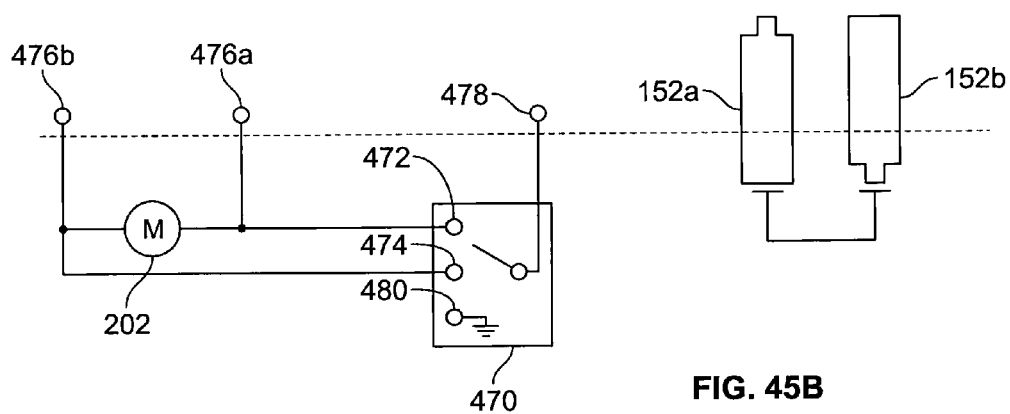
Figure 45C:
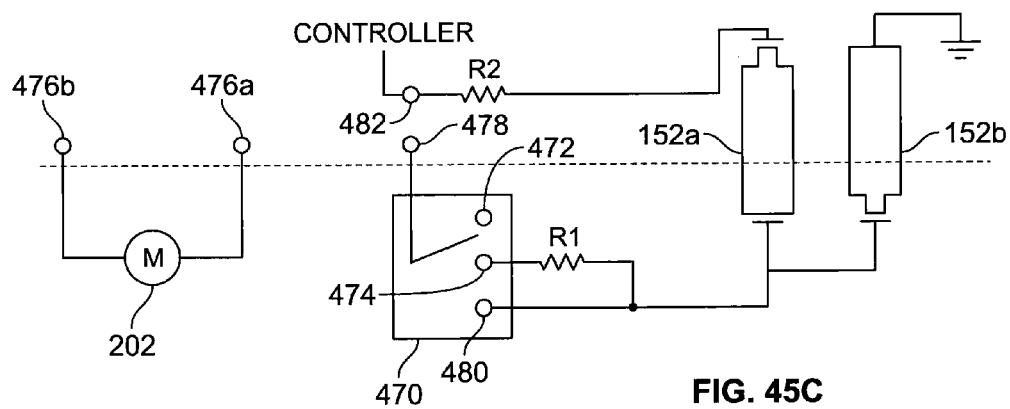

The arrangements shown in FIGS. 45B and 45C provide several advantages over the conventional arrangement shown in FIG. 45A as they require significantly fewer electrical interconnections to be formed between the various components, thereby minimizing the possibility of failure and increasing the reliability of the dispenser 100.

FIG. 45B illustrates a first alternative electrical interconnection arrangement with the motor 202 of the actuator drive system 200, the selector switch 470, and the batteries 152 where the controller reads a value from the selector switch 470 via a single connection, rather than the 4 connections illustrated in FIG. 45A. In this arrangement, signals delivered to the motor 202 at terminal 476 are used to detect different signals at the switch contacts 472 and 474.

To detect the position of the switch 470, the controller drives the motor 202 with a particular signal delivered to terminals 476 of the motor 202. If the same signal is detected by the controller at terminal 478, the switch 470 is positioned at terminal 472. If however, the signal detected at terminal 478 is inverse to the signal delivered to terminal 476, the switch 470 is positioned at terminal 474. If, however, no signal is detected, the switch 470 is positioned at terminal 480. In some implementations, the signal delivered to the motor 202 by the controller will comprise an alternating signal configured to move the motor 202 back and forth. In that case, the same algorithm can be used to detect a position of the switch 470 as the signal detected if the switch is positioned at terminal 474 will be the inverse of the alternating signal.

FIG. 45C illustrates a second alternative electrical interconnection arrangement with the motor 202 of the actuator drive system 200, the selector switch 470, and the batteries 152 where the controller reads a value from the selector switch 470 via a single connection, rather than the 4 connections illustrated in FIG. 45A. In this arrangement, terminal 472 of the switch 470 is open. Terminal 474 is connected to a first reference voltage equal to half of the voltage supplied by the batteries 152 reduced by resistor R1. Terminal 480 is connected to a second reference voltage equal to half of the voltage supplied by the batteries 152 without any reduction. Accordingly, the voltage across each of the three terminals is allocated to a pre-determined reference voltage that can be measured by the controller at terminal 478 via an analog-to-digital converter and used to identify a selected terminal of the selector switch 470. In this arrangement, the controller of the dispenser 100 includes an analog-to-digital converter that is connected to terminal 482 and, thereby, a first terminal of resistor R2. A second terminal of resistor R2 is connected to the full battery system supply voltage. In this implementation, the resistance values of resistors R1 and R2 are approximately equal. In that case, when the selector switch is in position 480, the voltage at the controller's analog-to-digital converter will be half of the full system battery voltage. When the switch is in position 474, the voltage at the analog-to-digital converter will be three-quarters of the full battery voltage, because of the one-half resistor divider of the one-half battery voltage. Finally, when the switch is in position 472, the value at the analog-to-digital converter will be the full battery voltage because that terminal point is unconnected.

FIGS. 46A-46E are electrical schematics showing example implementations of various electronic components of the dispenser 100 including the power supply 500, the selector switch 470, the bottle detection system 530, the motion detectors 408 and the motor 202 control unit, and the controller 600.

Figure 46A:
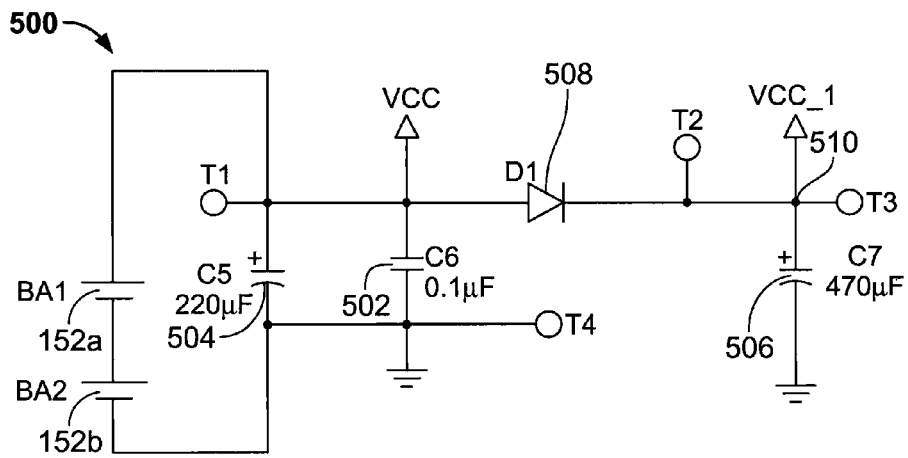
FIG. 46A is a schematic illustrating an example construction of a power supply of the dispenser.

FIG. 46A is a schematic illustrating an example construction of the power supply 500 for the dispenser 100. The power supply 500 comprises a D/C power supply powered by the batteries 152a and 152b connected in series. Capacitor 502 is connected between Vcc and ground to filter high-frequency noise from the output of the power supply 500. In one implementation, capacitor 502 has a capacitance value of approximately 0.1 micro farads. Capacitor 504 is also connected between Vcc and ground to provide smoothing for the output of the power supply 500. In one implementation capacitor 504 is polarized with the positive terminal being connected to Vcc and the negative terminal to ground, and has a capacitance value of approximately 220 micro farads. Output diode 508 provides reverse polarity protection to power supply 500 and is connected between Vcc and output node 510 of power supply 500. An additional capacitor 506 is connected between output node 510 of the power supply 500 and ground to provide additional smoothing of the power supply 500's output. In one implementation, capacitor 506 is polarized with the positive terminal being connected to output node 510 and the negative terminal to ground, and has a capacitance value of approximately 470 micro farads. The output node 510 of the power supply 500 can then be connected to the controller of the dispenser 100 for controlling the operation of the dispenser 100.

In the present embodiment, because the dispenser 100 is battery powered the system has limited energy available. As such, in one arrangement the motor of the actuator drive system 200 is driven so as to create a "rotary solenoid" by forcing the motor to a lock rotor position and holding the motor there while the fragrance is dispensed. This operation, though, causes the battery supply voltage to dip substantially. This dip is temporary, though, and will be recovered when the motor is released from the motor's locked position. However, when the batteries 152 start to weaken, the voltage dip can be so great that the level will fall below the reset level of the controller and could result in a system reset. To assist in avoiding this condition, FIG. 46A shows the creation of two power supplies separated by the diode 508. The first supply (shown as VCC) is used to power the motor, photo detectors, and other non-critical peripherals of the dispenser 100. The second supply (shown as VCC_1) is used to power the controller of the dispenser 100. When the battery voltage dips, the value of VCC may fall but the value of VCC_1 will remain higher because the power supplied by capacitor 506 cannot feed back through the diode 508 and is only used to supply energy to the controller. Accordingly, the capacitor 506 needs to be sufficiently large to supply power to the controller during the motor drive period, so that even if the battery supply and motor voltage dip, the controller voltage (VCC_1) will remain sufficiently high to keep the controller out of a reset condition.

Figure 46B:
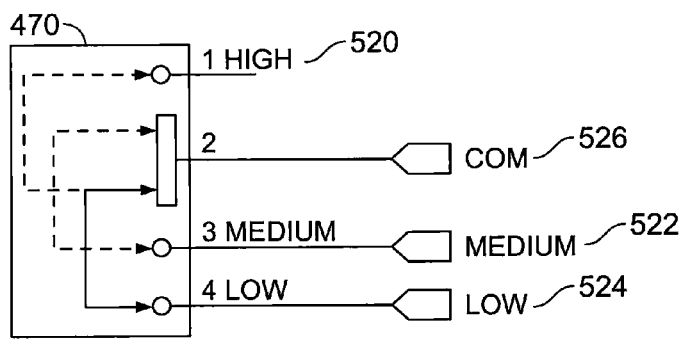
FIG. 46B is a schematic illustrating an example construction of a mode selector switch of the dispenser.

FIG. 46B is a schematic illustrating an example construction of the mode selector switch 470. The switch 470 receives as input three reference voltage values 520, 522, and 544 which may represent high (for example, Vcc), medium (for example, Vcc/2), and low (for example, ground) reference values. Depending upon the position of the selector switch 470 the selected reference value is outputted to output 526 (COM) for transmission to the controller 600 shown in FIG. 46E. The reference value at output 526 can then be converted to a digital value and used to determine a position of the switch 470. In other implementations, the switch 470 may be arranged differently as described in reference to FIGS. 45A-45C.

Figure 46C:
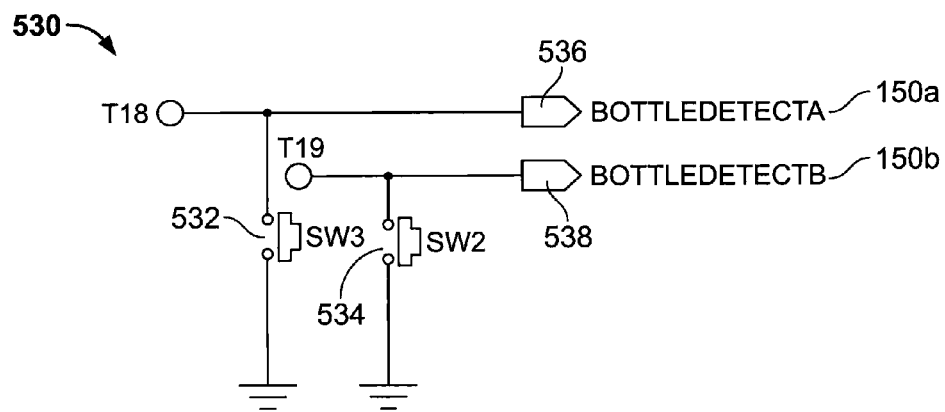
FIG. 46C is a schematic illustrating an example construction of a container detection circuit of the dispenser.

FIG. 46C is a schematic illustrating an example construction of a container detection circuit 530. Container detection circuit 530 includes pressure-sensitive switches 532 and 534. Each pressure-sensitive switch is positioned proximate one of the container detection arms 306 described above. If a container 150 presses against one of the container detection arms 306 (indicating the presence of a container 150), that container detection arm 306 deforms accordingly and presses against its respective pressure-sensitive switch 532 or 534. With sufficient pressure, the pressure-sensitive switch closes, causing the output of container detection circuit 530 to be pulled to ground for that particular container. Accordingly, with respect to FIG. 46C, if container 150a is present, switch 532 is closed and the relevant output 538 goes to ground. If container 150a is not present, the output 536 adopts a different value. Similarly, if container 150b is present, output 538 goes to ground. Accordingly, the outputs 536 and 538 can be passed to the controller of the dispenser 100 and utilized to determine a number of containers 150 that are present within the dispenser 100. The controller can then adopt a particular operating mode based upon the number of present containers, as described above. In another implementation, the switches 532 or 534 may instead be connected to Vcc rather than ground.

Figure 46D:
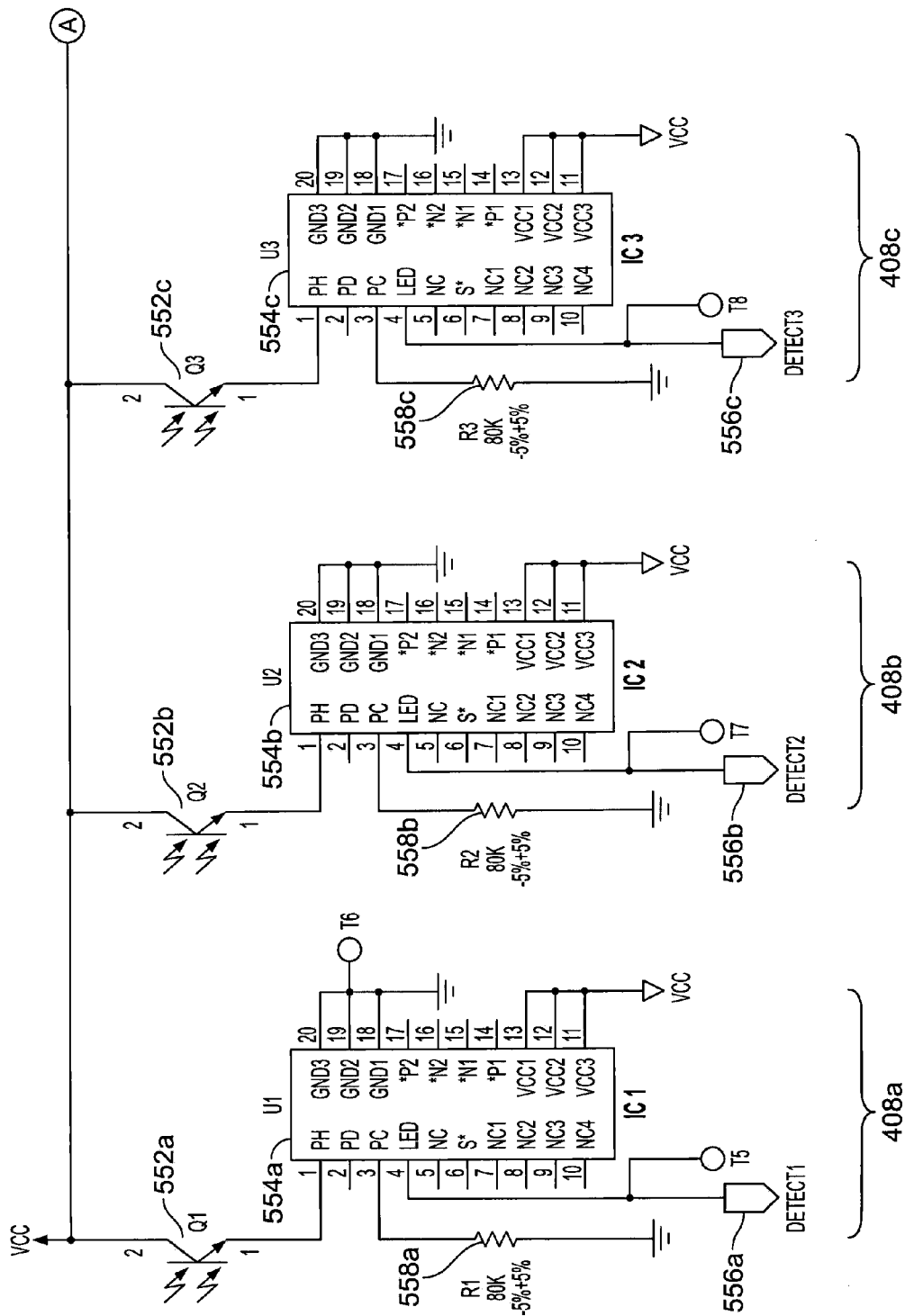
FIG. 46D is a schematic illustrating an example construction of a circuit for implementing the motion detectors and a motor control circuit of the dispenser.
Figure 46D:
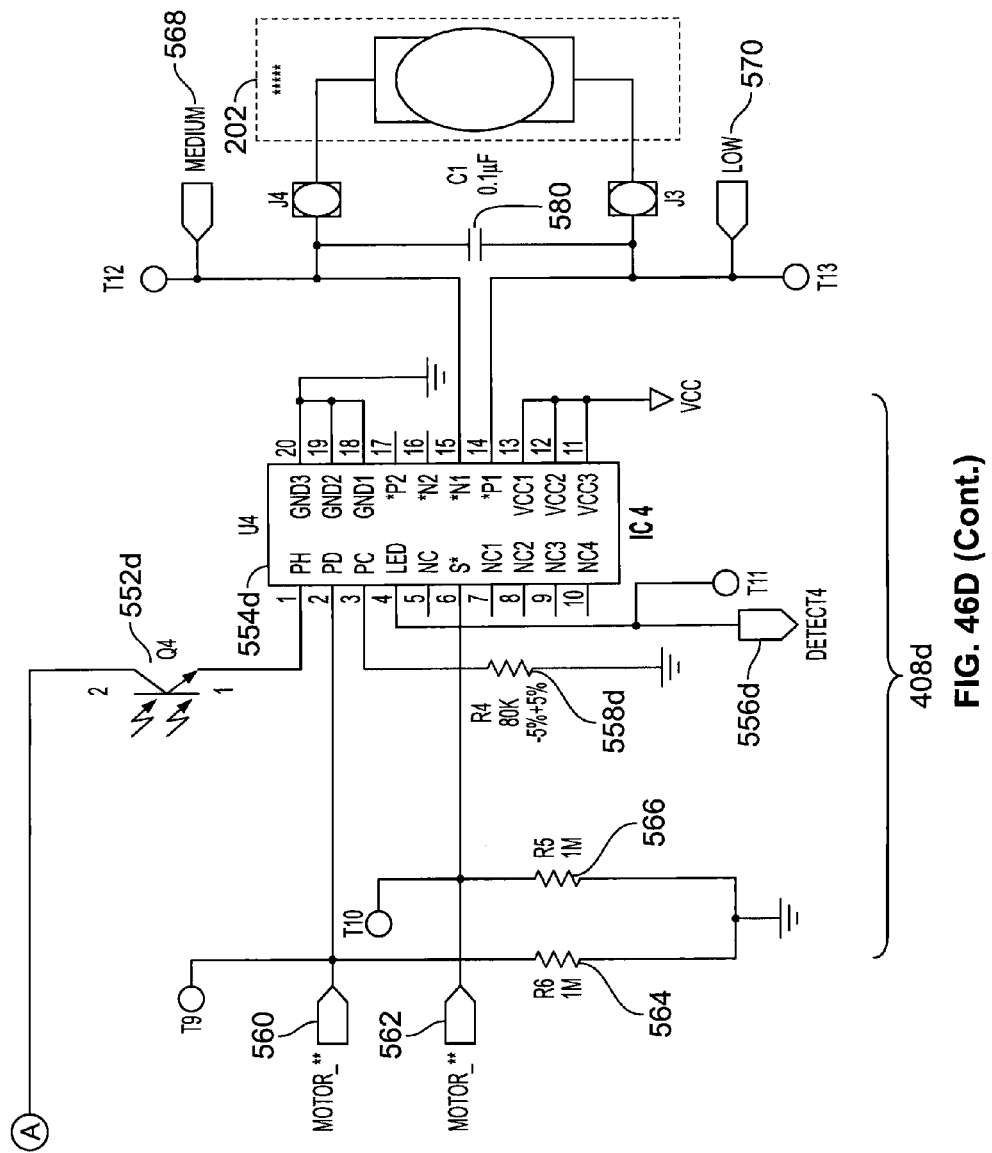

FIG. 46D is a schematic illustrating an example construction of a circuit for implementing the motion detectors 408 as well as a control circuit for the motor 202. As shown in FIG. 46D the circuit includes 4 motion detectors 408a, 408b, 408c, 408d. In different implementations, though, different number of motions detectors 408 may be implemented. The construction of each motion detector circuit is generally the same, although motion detector 408d incorporates a number of additional components that make-up the control circuit for the motor 202.

Each motion detector includes a light sensor 552 that may comprise any suitable component for detecting variations in light energy entering the light sensor. Although in FIG. 46D each light sensor 552 is depicted as comprising the same component, different light sensing elements may be incorporated into each of motion detectors 408a, 408b, 408c, 408d.

Output from each light sensor 552 is inputted into pin1 (PH) of integrated circuits (IC) or application-specific integrated circuits (ASICs) 554. As the light energy entering each light sensor 552 varies (either due to movement or other changes in ambient light), an analog voltage value delivered to pin 1 of IC 554 varies.

Each IC 554 analyzes the input received from its respective light sensor 552 to determine whether changes in light energy (indicative of movement) are detected. The ICs may be programmed to implement any suitable data analysis algorithm for detecting movement. For example, the ICs may analyze data received from light sensors 552 to identify changes in light levels that occur within pre-determined time frames that are consistent with the movement of an individual walking past the dispenser 100. Alternatively, where sensor 552 is sensitive to a particular frequency spectrum of infrared light emitted by humans and/or other animals, ICs 554 may simply analyze the signal received from light sensors 552 to identify a sufficiently-long period of time during which that particular frequency of light is detected.

If one or more of ICs 554 determines that movement is detected, the output of pin 4 (LED) of those ICs 554 is set to a particular voltage level indicative that movement has been detected. That output is then communicated through output nodes 556 of motion detectors 408a, 408b, 408c, or 408d for use by the controller of dispenser 100.

In each IC 554 motion detector 408, pins 18-20 (GND1, GND2, GND3) are tied to ground, while pins 11-13 (VCC1, VCC2, VCC3) are tied to Vcc. Additionally, pin 3 (PC) of each IC 554 is tied to ground through resistor 558. In one implementation, resistor 558 has a resistance value of approximately 80K ohms.

As shown in FIG. 46D, the fourth motion detector 408d includes additional components for operating the motor 202. Inputs 560 (motor_bw) and 562 (motor_fw) are received from the controller and are used to control the backward and forward rotation of the motor 202, respectively. Input 560 is connected to pin 2 (PD) of IC 554d and input 562 is connected to pin 6 (SW) of ICC 554d. Additionally, input 560 is connected to ground via pull-down resistor 564. In one implementation, pull-down resistor 564 has a resistance value of approximately 1 mega ohm. Input 562 is connected to ground via pull-down resistor 566. In one implementation, pull-down resistor 566 has a resistance value of approximately 1 mega ohm.

As the output of the motor control, pin 15 (MN1) of IC 554d is connected to input 568 (medium) as well as a first terminal of motor 202. Pin 14 (MP1) of IC 554d is connected to input 570 (low) as well as a second terminal of the motor 202. These low and medium connection points 570, 568, respectively, correspond to the positions 472, 474, respectively, of the selector switch arrangement illustrated in FIG. 45B. The first and second terminals of the motor 202 are also connected across high-frequency filter capacitor 580 to remove high-frequency noise signals delivered to the motor 202. In one implementation, capacitor 580 has a capacitance of approximately 0.1 micro farads.

In the implementation shown in FIG. 46D, the motor 202 is driven using an H-Bridge arrangement. To stop the motor 202, both MOTOR_FW 562 and MOTOR_BW 560 are set to low values. To drive the motor 202 backward, MOTOR_FW 562 is set to a low value, while MOTOR_BW 560 is set to a high value. To drive the motor 202 forward, MOTOR_FW 562 is set to a high value, while MOTOR_BW 560 is set to a low value. MOTOR_FW 562 and MOTOR_BW 560 both having high values would represent an error condition that could cause damage to the motor 202 and dispenser 100.

Figure 46E:
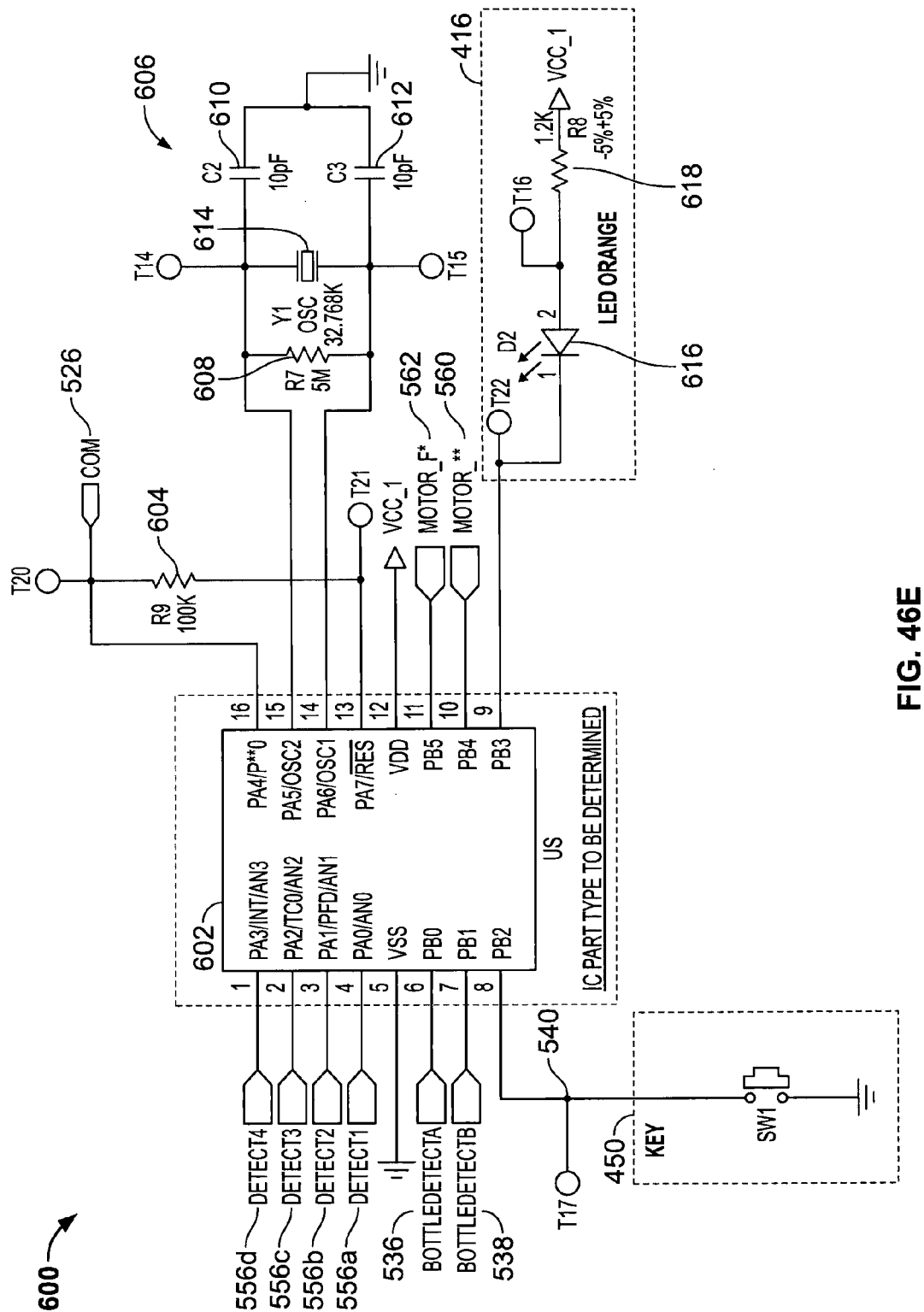
FIG. 46E is a schematic illustrating an example construction of a circuit for controlling the operation of the dispenser.

FIG. 46E is a schematic illustrating an example construction of a circuit for controller 600 of the dispenser 100 showing controller 600 in communication with the LED 416 and the switch 450 of the top plate 108. The functionality of controller 600 is implemented by IC 602 that is programmed to implement an operational methodology of the dispenser 100 as described above. Pins 1-4 of IC 602 receive inputs 556a-d from motion detectors 408a-d. Pin 5 (Vss) of IC 602 is connected to ground and pins 6 (PB0) and 7 (PB1) receive as inputs container detection signals 536 and 538, respectively, received from container detection circuit 530. Pin 8 (PB2) of IC 602 is connected to a first terminal of switch 450 to receive input 540 via the top plate 108, as described above. The second terminal of the switch 450 is connected to ground. As such, when the top plate 108 is depressed by a user, the input to pin 8 of IC 602 goes to ground.

Pin 16 (PA4/PWM0) of IC 602 receives input 526 indicative of a current position of the selector switch 470. Pin 16 is also tied to pin 13 (PA7/!RES) via resistor 604. In one implementation resistor 604 has a resistance value of approximately 100K ohm.

Pins 15 (PA5/OSC2) and 14 (PA6/OSC1) of IC 602 are connected to clock network 606. Clock network 606 provides a clock signal to IC 602 allowing IC 602 to execute a program stored therein for implementing the operational methodology of the dispenser 100. Pin 15 of IC 602 is connected to a first terminal of resistor 608, a first terminal of capacitor 610, and a first terminal of oscillator 614. The second terminal of capacitor 610 is connected to ground. Pin 14 is connected to a second terminal of resistor 608 and a first terminal of capacitor 612. The second terminal of capacitor 612 is connected to ground. Pin 14 is also connected to a second terminal of oscillator 614. In one implementation, resistor 608 has a resistance of approximately 5 mega ohms and each of capacitors 610 and 612 have capacitances of approximately 10 pico farads. In one implementation, oscillator 614 comprises a crystal oscillator configured to operate at approximately 32.768 kHz.

IC 602 is also in communication with LED 416. Pin 9 (PB3) of IC 602 is connected to a first terminal of LED 616. The second terminal of LED 616 is connected to a first terminal of current-limiting resistor 618. A second terminal resistor 618 is connected to ground. In one implementation resistor 618 has a resistance of approximately 1.2 k ohm. To illuminate LED 416, therefore, IC 602 is programmed to set pin 9 of IC 602 a high level (for example, Vcc) causing diode 616 to be illuminated.

During operation, IC 602 of controller 600 analyzes inputs 556a-d, 536, 538, 540 and 526 to determine whether an action needs to be taken. The analysis is determined by dispenser 100's current operational methodology, for example in accordance with the timing diagrams illustrated in FIGS. 40-43, the state flow diagram shown in FIG. 47, or other operational algorithms described above.

In one example, IC 602 may determine that motion has been detected via one of inputs 556a-d. If so, IC 602 may first verify that there is no currently active lockout period. If not, IC 602 verifies that a container 150 is present by analyzing at least one of inputs 536 and 538. If an appropriate container 150 is present, IC 602 uses outputs 562 or 560 to control an operation of the motor 202 to cause product to be dispensed from the dispenser 100. If the primary container 150 is not available, IC 602 can use the other of inputs 536 and 538 to determine whether the secondary container 150 is available for use. IC 602 may also, upon determining that motion has been detected via at least one of inputs 556a-d, cause LED 416 to illuminate according to a particular algorithm. Additionally, IC 602 can monitor a status of the switch 450 via input 540 to determine whether a user has manually requested that product be dispensed. When implementing a lockout timer, IC 602 uses input 526 to determine the lockout period currently selected by a user via selector switch 470.

Figure 47:
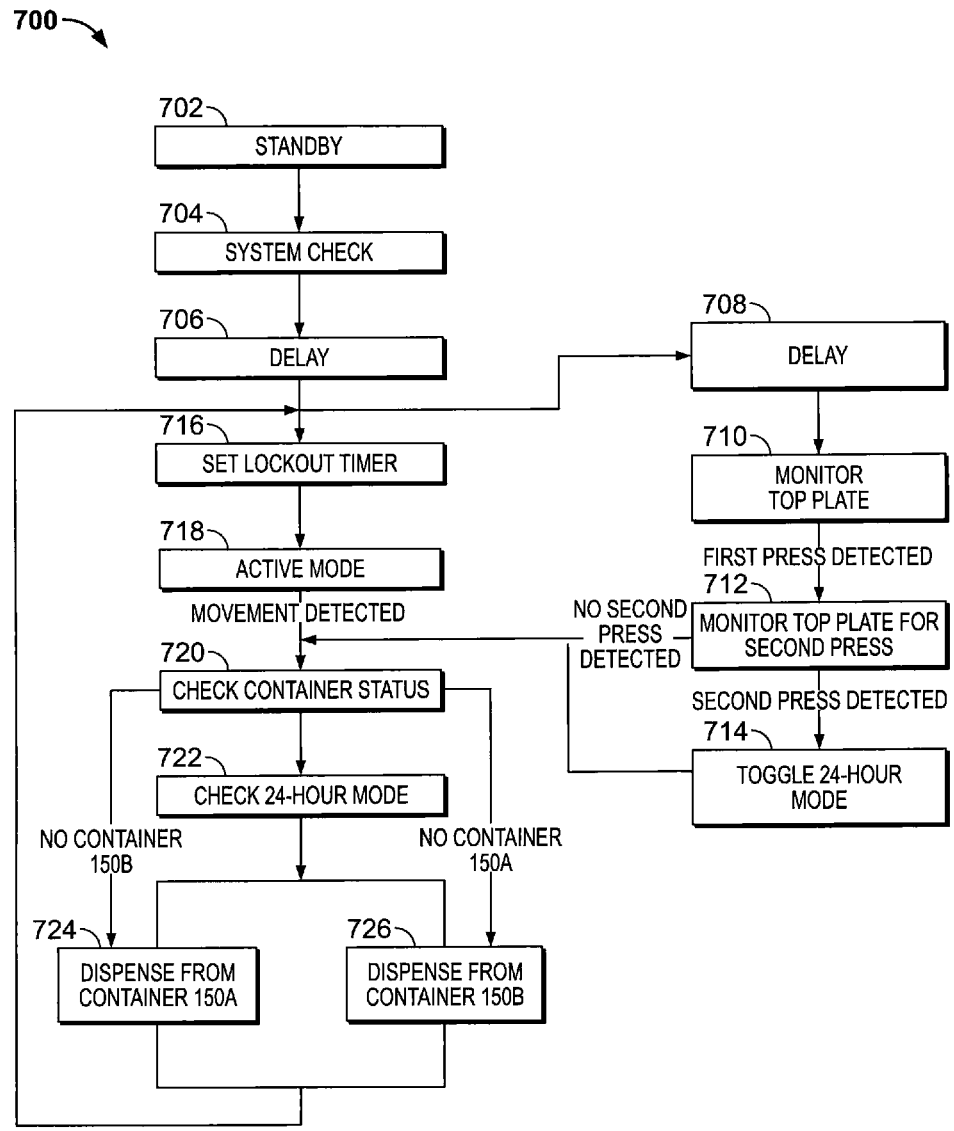
FIG. 47 is a state diagram illustrating a state flow of the dispenser in accordance with the present disclosure.

FIG. 47 is a state diagram illustrating state flow 700 of the dispenser 100 in accordance with the present disclosure. In initial state 702 the dispenser 100 enters a standby mode. The dispenser 100 may enter this state after the top section 104 of the housing 102 is connected to the bottom section 106 causing power supplied by batteries 152 to be delivered to the controller of the dispenser 100. Alternatively, the dispenser 100 may enter state 702 after, for example, experiencing an error condition that causes the device to reset.

After entering standby state 702, the dispenser 100 may enter a test mode or system check 704, wherein the dispenser 100 determines whether the device has been placed into a test mode—for example to assist in testing the device to verify that it is operating correctly. At this time the dispenser 100 may also perform a low battery check. If the voltage measured across batteries 152 (Vref) is less than a particular threshold (Vlowbat), the dispenser 100 sets a state value indicating that the battery level is low. This may cause the dispenser 100 to illuminate an LED indicating to a user that the batteries of the dispenser 100 should be replaced. After performing the battery level check, the dispenser 100 may be configured to implement a start-up delay (for example, a delay of 0.1 ms) in state 706.

After implementing the delay, the dispenser 100 enters into three separate control loops that are executed by the controller (e.g., controller 600). The first control loop (states 708-714) involves the dispenser 100 monitoring the manual user interface of the dispenser 100. The second control loop (states 716-724/726) involves the dispenser managing lock-out periods and monitoring input received from the motion detectors 408. The third control loop is not illustrated in FIG. 47 but involves the dispenser 100 implementing a 24-hour counter in order to implement the algorithm illustrated in FIG. 43.

In the first control loop, the dispenser 100 first implements a 0.4 second delay in state 708. Depending upon the implementation, though, the delay of state 708 may only be implemented the first time that the dispenser 100 is powered up. After implementing the delay of state 708, the dispenser 100 determines whether the top plate 108 of the dispenser has been pressed in state 710. The dispenser 100 remains in state 710 until it detects a successful press of the top plate 108. In one implementation, a successful press of the top plate 108 is one that persists for a longer duration and a predetermined minimum press threshold.

After detecting an initial press in state 710, the dispenser 100 starts a button press timer a monitors the top plate 108 for a second press in state 712. If a second button press is detected before a button press timer expires, the dispenser moves to state 714 in order to reset or toggle the 24-hour timer and to toggle the primacy of the first and second containers. See, for example, the timing diagram shown in FIG. 43 that illustrates this operation. After resetting the 24-hour timer and toggling the primacy of containers 150, dispenser 100 moves onto state 720, which is discussed further, below. Alternatively, if no second press of the top plate 108 is detected, the dispenser moves directly to state 712 without modifying the 24-hour timer.

In the second control loop, the dispenser 100 first sets a lockout timer in state 716. The lockout timer is set to a value dictated by the user's positioning of the selector switch 470, as described above. After setting the lockout timer, the dispenser implements a lockout timer to count down the duration of the lockout period. During the lockout period, the dispenser 100 may monitor motion detectors 408 in order to illuminate an LED, as described above, but will not trigger the dispersal of product.

After the lockout timer expires, the dispenser 100 transition into an active mode state 718. In the active mode the dispenser 100 monitors motion detectors 408 for movement. If movement is detected the dispenser 100 will dispense product.

After detecting movement, the dispenser moves to state 720 in order to identify which containers 150 are present within the dispenser 100. As discussed above, in each 24 hour period, a different one of containers 150 is selected as the primary container to be used when dispenser 100 is to dispense product. Accordingly, before dispersing product after detecting movement (or receiving detecting a button press (from the first control loop) the dispenser 100 must identify which containers are available.

If no containers 150 are available (containers 150*a* and 150*b* are both absent), the dispenser 100 indicates to the user that a container must be installed into the device and moves to a halt state (not shown). If only a single container 150 is available (that is, either container 150*a* or container 150*b* is present, but not both) dispenser 100 dispenses product from the available container 150 in either state 724 or 726. If, however, both containers 150*a* and 150*b* are available, dispenser 100 identifies the current 24-hour state in state 722 to determine which of containers 150*a* and 150*b* are allocated the role of primary container. Depending upon which container 150 is primary, the dispenser 100 moves to either state 724 or 726 to dispense product therefrom.

After dispensing product in either of states 724 or 726, the dispenser 100 may be configured to check a spray count for the container 150 from which product was just dispensed. If the spray count exceeds a particular threshold, the dispenser may indicate to a user of dispenser 100 that the container 150 for which the spray count threshold was exceeded requires replacement. After verifying the spray count, the dispenser returns to the beginning of both the first and second control loops by entering states 716 and 708.

Any of the embodiments described herein may be modified to include any of the structures or methodologies disclosed in connection with different embodiments. Further, the present disclosure is not limited to the use of aerosol containers of the type specifically shown. Still further, a dispenser configured in accordance with any of the embodiments disclosed herein may be modified to work with any type of aerosol or non-aerosol container of product.

More specifically, any of the advantages previously noted with respect to the utilization of a plurality of sensors could be incorporated into other known prior art dispensers to provide users similar benefits. Previously known dispensers were typically provided as standalone devices that automatically sprayed a fluid in response to a timed interval, e.g., spraying an air freshener within a room or a pest control device within a barn. These dispensers are kept "out of sight" of users by placing them in areas of a room or space that are utilized less frequently by users or that provide the ability to "hide" or otherwise diminish the impact of the dispenser on the aesthetics of the room or space. In these circumstances, the dispensers are often less effectual and often cause users to place such devices in sub-optimal areas of a room or space in terms of their ability to effectively disperse an active, volatile, or any other manner of material or product.

Further, some prior art dispensers utilize sensors to initiate various pre-programmed or user initiated operational sequences, as well as to provide instant dispensing upon the detection of sensory input. In these prior art dispensers, designers utilized single sensor systems in light of users predisposition to "hide" or otherwise place such devices in unobtrusive areas of a room or space. Indeed, a limited scope of sensory detection was preferable in these prior art systems in view of the manner in which such systems were utilized.

Presently, the disclosure of the various embodiments herein identifies a dispensing system that is intended to be left in "plain view" of a user and otherwise positioned prominently within a room or space, i.e., not hidden or otherwise intentionally obstructed. Therefore, the various disclosed embodiments utilize a plurality of sensors to enhance the field of view of the dispensing system to be more responsive to external sensory input, thereby providing a truly responsive dispensing system to the activity in a particular room or space. Further, in situations where an obstruction is placed in a portion of a dispensers field of view, the remaining field of view of the other sensor(s) still affords the ability to respond to sensory input. Such advantages are contemplated to be made in connection with other types of devices, of which several non-exhaustive examples are provided below.

Figure 49:
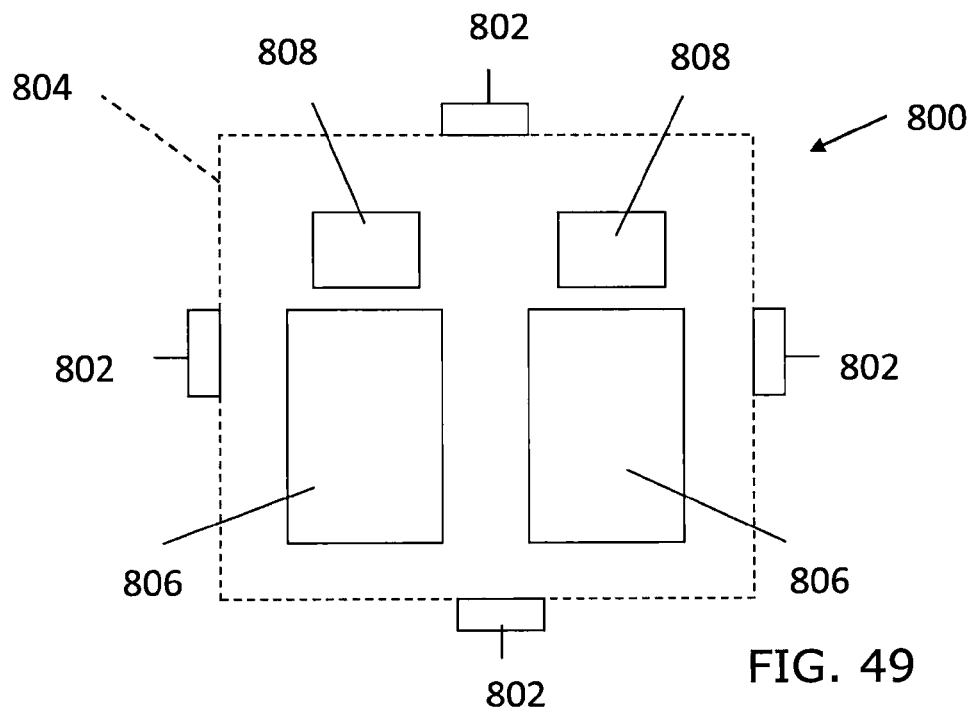
FIG. 49 is a schematic representation of an alternative embodiment of a diffuser utilizing a plurality of sensors.

In one embodiment, a conventional oil or product diffuser 800 may be modified to include a plurality of sensors 802 to detect sensory input within a room or space. Such diffusers may be wall mounted, could include plugs for insertion into conventional electrical outlets, could include corded plugs, or may have an internal power source, such as batteries. As illustrated in FIG. 49, a diffuser 800 may be provided with a plurality of sensors 802 about a perimeter of a housing 804 thereof to provide a sensory field of view or an enhanced sensory field of view. In one embodiment, two sensors are provided, in a different embodiment 3 sensors are provided, in yet a different embodiment 4 sensors are provided, in still a further embodiment 5 sensors are provided. While any number of sensors may be utilized, the depicted embodiment shows a sensor 802 on four sides of a diffuser housing 804. It is anticipated that utilization of a plurality of sensors will allow for the detection of sensory input, which may be utilized to provide one or more of the powering on or off of the diffuser, the initiation of a pre-programmed timed sequence of diffusion, the initiation of a sequence that comprises one or more diffusion periods between one or more non-diffusion periods, the initiation of a sequence that includes a continual diffusion sequence, the initiation of an immediate diffusion of a product, the initiation of the diffusion of a product after a specified or non-specified delay, the initiation of a diffusion sequence characterized by diffusing a product in response to one or more of a time interval, sensory input, or manual actuation after the initial detection of sensory input, and the initiation of one or more previously noted actions in connection with a diffuser having a single container, two containers, three containers, or any other number of additional containers 806. Further, it is contemplated that diffusion may be realized by one or more activation means 808 that include heating a container, heating a wick extending from or into a container, heating an area adjacent a wick and/or container, running a fan adjacent an aperture of a container or a wick extending from a container, running a fan within a housing to assist in dispersal of a product, activating a piezo-electric plate adjacent a wick to volatize a fluid thereon, opening a window or otherwise removing an obstruction from an aperture or opening to assist in the dispersal of product from the housing, or any other known means for diffusing.

Figure 50:
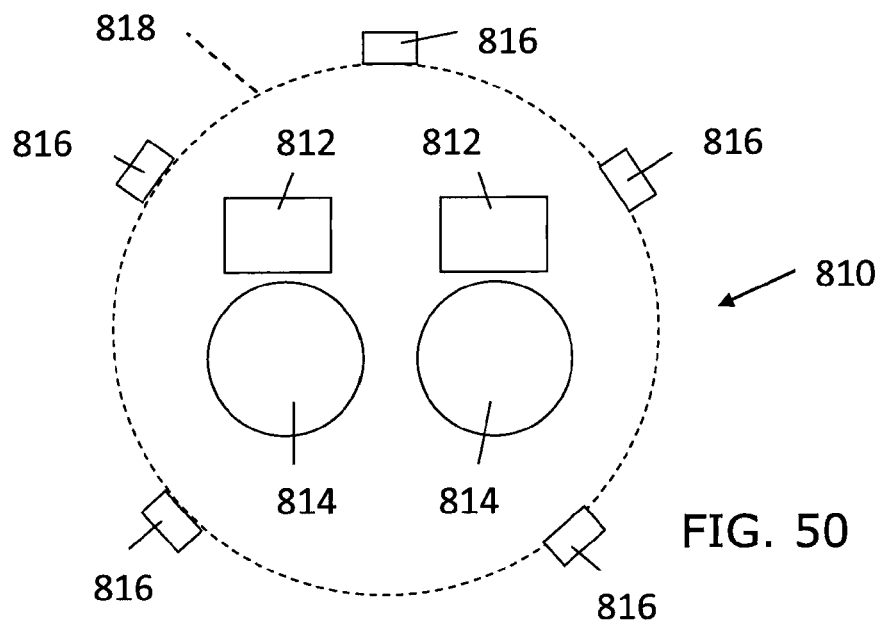
FIG. 50 is a schematic representation of an alternative embodiment of an electronic dispensing system utilizing a plurality of sensors.

In a different embodiment, other conventional electronic dispensing systems 810 that utilize actuation mechanisms 812 to spray fluid from an aerosol container, whether metered or non-metered, and pump-type sprayers, whether pre-compression or non pre-compression pump-type sprayers, may be modified to include a plurality of sensors to detect sensory input within a room or space. Conventional actuation mechanisms may include, but are not limited to, mechanically driven means, such as armatures, levers, linkages, cams, etc., that depress, tilt, or otherwise activate a valve stem or pump of a container by direct interaction with the valve stem or pump, through indirect communication with the valve stem or pump, and/or through physical interaction with the container, i.e., lifting, pushing, tilting, lowering, or otherwise deflecting the container to effect the depression or tilting of the valve stem or pump. It is also contemplated that solenoid actuators, bi-metallic actuators, muscle wire actuators, piezo actuators, or any other means may be utilized to effect spraying of an aerosol or pump type container. Further, it is also contemplated that other dispensing and actuation mechanisms 812 may be utilized, such as those used in connection with nebulizers or venturi sprayers. Still further, any of these systems 810 may utilize a product or fluid provided within a container or reservoir 814 that is pressurized or non-pressurized. Such dispensing systems 810 may be wall mounted, could include plugs for insertion into conventional electrical outlets, could include corded plugs, or may have an internal power source, such as batteries. As illustrated in FIG. 50, a dispensing system 810 may be provided with a plurality of sensors 816 about a perimeter of a housing 818 thereof to provide a sensory field of view or an enhanced sensory field of view. In one embodiment, two sensors are provided, in a different embodiment 3 sensors are provided, in yet a different embodiment 4 sensors are provided, in still a further embodiment 5 sensors are provided. While any number of sensors may be utilized, the depicted embodiment shows a sensor on five sides of a housing 818. It is anticipated that utilization of a plurality of sensors 816 will allow for the detection of sensory input, which may be utilized to provide one or more of the powering on or off of the system, the initiation of a pre-programmed timed sequence of spraying, the initiation of a sequence that comprises one or more spraying periods between one or more non-spraying periods, the initiation of a sequence that includes a continual spraying sequence, the initiation of an immediate spraying of a product, the initiation of the spraying of a product after a specified or non-specified delay, the initiation of a spraying sequence characterized by spraying a product in response to one or more of a time interval, sensory input, or manual actuation after the initial detection of sensory input, and the initiation of one or more previously noted actions in connection with a system having a single container, two containers, three containers, or any other number of additional containers 814. It is also contemplated that such modifications could be utilized with existing dispensing systems 810 that utilize aerosol containers or pump-type sprayers in conjunction with solenoids that provide for the release of product into the environment.

Figure 51:
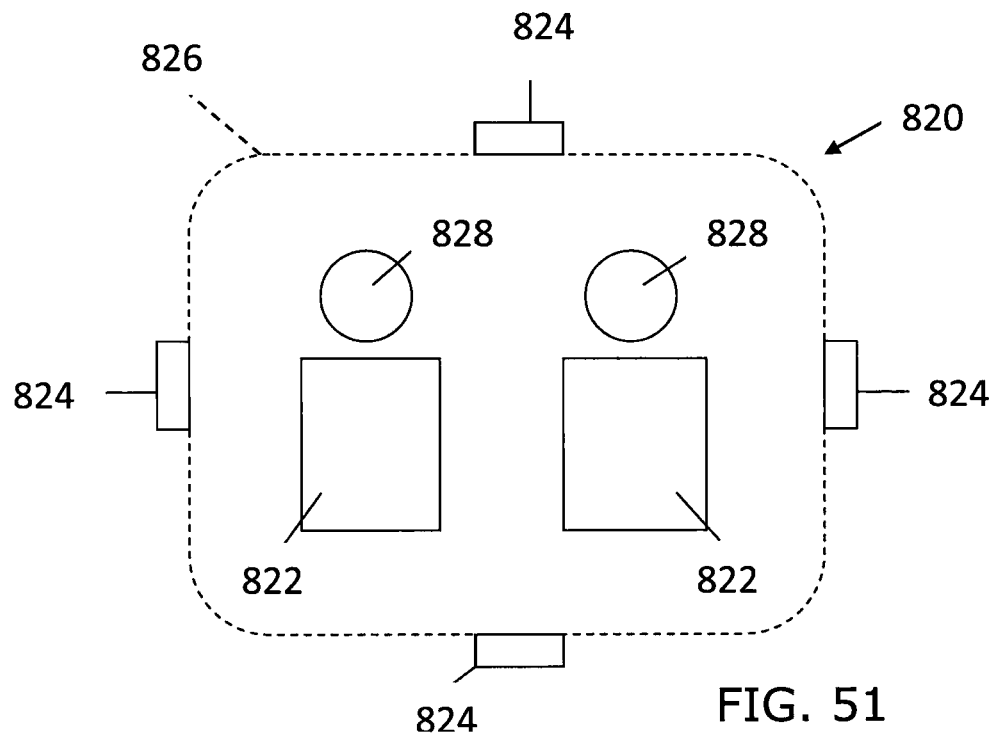
FIG. 51 is a schematic representation of another alternative embodiment of a diffuser utilizing a plurality of sensors.

In yet another embodiment, a conventional diffuser 820 that utilizes a cartridge or reservoir 822 that holds one or more of a product, volatile or active laden gel or liquid may be modified to include a plurality of sensors 824 to detect sensory input within a room or space. Such diffusers 820 may be wall mounted, could include plugs for insertion into conventional electrical outlets, could include corded plugs, or may have an internal power source, such as batteries. As illustrated in FIG. 51, a diffuser 820 may be provided with a plurality of sensors 824 about a perimeter of a housing 826 thereof to provide a sensory field of view or an enhanced sensory field of view. In one embodiment, two sensors are provided, in a different embodiment 3 sensors are provided, in yet a different embodiment 4 sensors are provided, in still a further embodiment 5 sensors are provided. While any number of sensors may be utilized, the depicted embodiment shows a sensor 824 on four sides of the diffuser housing 826. It is anticipated that utilization of a plurality of sensors 824 will allow for the detection of sensory input, which may be utilized to provide one or more of the powering on or off of the diffuser, the initiation of a pre-programmed timed sequence of diffusion, the initiation of a sequence that comprises one or more diffusion periods between one or more non-diffusion periods, the initiation of a sequence that includes a continual diffusion sequence, the initiation of an immediate diffusion of a product, the initiation of the diffusion of a product after a specified or non-specified delay, the initiation of a diffusion sequence characterized by diffusing a product in response to one or more of a time interval, sensory input, or manual actuation after the initial detection of sensory input, and the initiation of one or more previously noted actions in connection with a diffuser having a single cartridge or reservoir, two cartridges or reservoirs, three cartridges or reservoirs, or any other number of additional cartridges or reservoirs 822. Further, it is contemplated that diffusion may be realized by one or more activation means 828 that may include one or more of heating a cartridge or reservoir, heating an area adjacent a cartridge or reservoir, running a fan adjacent an aperture or vapor permeable membrane of a cartridge or reservoir, running a fan within a housing to assist in dispersal of a product, rotating or otherwise moving a cartridge or reservoir, opening a window or otherwise removing an obstruction from an aperture or opening to assist in the dispersal of product from the housing, or any other known means for diffusing.

Figure 52:
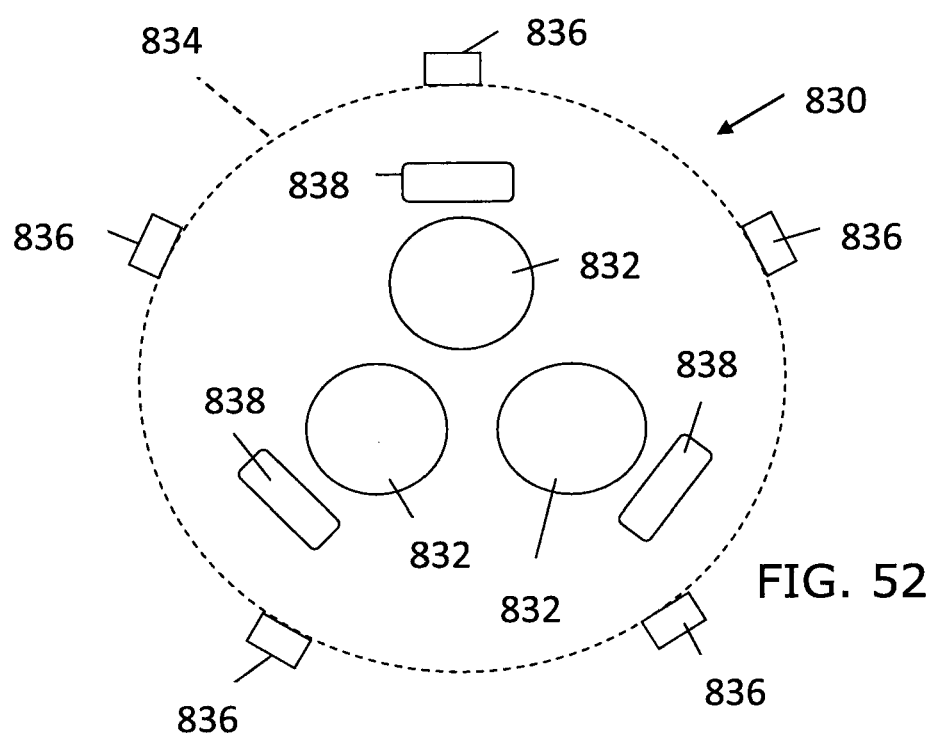
FIG. 52 is a schematic representation of an alternative embodiment of a candle system utilizing a plurality of sensors.

In still another embodiment, a system 830 including one or more candles, fragrance blocks, wax melts, or products 832, whether solid or gel, that allow for the diffusion of an active or volatile through the melting thereof (hereinafter referred to collectively as "candles"), are provided within a housing or on a base 834 that may be modified to include a plurality of sensors 836 on the housing or base to detect sensory input within a room or space. The housing or base 834 includes one or more heaters and or heating means 838 powered by a wall mounted plug, a corded plug, or an internal power source, such as batteries. As illustrated in FIG. 52, the candle system 830 may be provided with a plurality of sensors 836 about a perimeter of the base 834 and the base may include one or more candles, e.g., 2 candles, 3 candles, 4 candles, 5 candles, or any additional number of candles. Further, the candles could instead be provided in a housing 834. Still further, one or more of the aforementioned candles could be provided on one or more housings or bases 834, wherein the plurality of sensors are distributed among the plurality of housings and/or bases. In one embodiment, two sensors are provided, in a different embodiment 3 sensors are provided, in yet a different embodiment 4 sensors are provided, in still a further embodiment 5 sensors are provided. While any number of sensors 836 may be utilized, the depicted embodiment shows three equidistantly spaced sensors 836 about a circular base 834. It is anticipated that utilization of a plurality of sensors 836 will allow for the detection of sensory input, which may be utilized to provide one or more of the powering on or off of the heater(s), the initiation of a pre-programmed timed sequence of heating, the initiation of a sequence that comprises one or more heating periods between one or more non-heating periods, the initiation of a sequence that includes a continual heating sequence, the initiation of an immediate heating of a candle, the initiation of the heating of a candle after a specified or non-specified delay, and the initiation of a heating sequence characterized by heating a candle in response to one or more of a time interval, sensory input, or manual actuation after the initial detection of sensory input.

Indeed, any prior art dispenser may be modified in a similar manner as discussed in connection with the above-noted embodiments. As has been previously described, any known prior art dispenser may be adapted to include 3, 4, 5, . . . , n sensors around a perimeter thereof, such that the dispenser can be placed anywhere within a space and still be able to detect sensory input.

Example Use Case of Dispenser

In one example use of the dispenser 100, a user first installs the containers 150a, and 150b and batteries 152a, and 152b into dispenser 100. To perform the installation, the user orients the dispenser 100 correctly before separating the top section 104 from the bottom section 106. As described above, the weight-bias of the dispenser 100 due to the position of the actuator drive system 200 in the bottom section 106 provides tactile feedback to the user allowing the user to orient the dispenser 100 with the top section 104 being positioned above the bottom section 106.

After orienting the dispenser 100 correctly, the user separates the top section 104 from the bottom section 106 by rotating the top section 104 counter-clockwise (when viewed from above) with respect to the bottom section 106. The rotation causes the locking members 166 of the top section 104 to be withdrawn from the locking tabs 124 of the bottom section, thereby unlocking the two sections of the housing 102 of dispenser 100. After unlocking the two sections, the top section 104 of the housing 102 can be separated from the bottom section 106.

After separating the top section 104 from the bottom section 106, the apertures 120 and 122 of the bottom section 106 are exposed, thereby allowing the user to insert the containers 150 and batteries 152 into their respective apertures. Because the containers 150 and the batteries 152 are sized differently, the user cannot incorrectly position the containers 150 by accidently inserting them into the apertures 122. Similarly, the size of batteries 152 provides clear feedback to the user allowing the user to correctly select the apertures 122 for the batteries 152.

After inserting the containers 150 and the batteries 152 into the bottom section 106 of the housing 102, the top section 104 is positioned over the bottom section 106 so that the two sections can be locked to one another. As described above, the containers 150 and the batteries 152, when disposed within bottom section 106, act as guides to facilitate the correct positioning of the top section 104 over the bottom section 106. After positioning, the top section 104 can be locked to the bottom section 106 by twisting the top section 104 with respect to the bottom section 106 in a clock-wise direction to cause the locking members 166 of the top section 104 to engage with the locking tabs 124 of the bottom section 106.

With the top section 104 mounted to the bottom section 106, electrical interconnects are formed with batteries 152 allowing electrical energy to be supplied to the various electronic components of the dispenser 100.

The user can then manipulate the switch 470 to select a lockout period of the dispenser 100. The lockout period controls the maximum frequency at which the dispenser 100 will dispense product upon detecting movement in proximity to the dispenser 100.

After connecting the top section 104 and the bottom section 106 of the housing 102, the user selects an appropriate location for the dispenser 100. Because the housing 102 of the dispenser 100 is relatively featureless, dispenser 100 has a clean, appealing appearance. As such, the user is likely to position the dispenser 100 in the middle of a living space or in another prominent position within the living space. Because the dispenser 100 is likely to be placed prominently within a living space, the dispenser 100 will have a relatively effective view of the living space, thereby ensuring that the product contained within the containers 150 is dispensed effectively within that living space. Often, for example, the user positions the dispenser 100 on a coffee table or other surface near the middle of the room.

Because the appearance of the housing 102 is clean and featureless, the user is generally not cognizant of the orientation of the dispenser 100 when it is positioned in the living space. Accordingly, unlike other dispensers that require particular and careful positioning and orientation in order for their motion detection systems to operate correctly, the present dispenser 100 can be positioned by a user in a location for solely aesthetic reasons, rather than functional ones. As discussed above, because the motion sensing system of the dispenser 100 is configured to detect movement around the dispenser 100, irrespective of the user's positioning of the dispenser 100, the dispenser 100 will be able to observe movement within the living space and dispenser product accordingly.

After placing the dispenser 100 into the living space, the dispenser 100 may be left to operate automatically by dispensing product from one of the containers 150 upon detecting movement. In that case, the dispenser 100 selects the appropriate container 150 from which to dispense product based upon a predetermined container 150-selection algorithm, as described above. Alternatively, the user can interact with the dispenser 100 to manually cause the dispenser 100 to dispense product, for example, by depressing the top plate 108. Additionally, the user can manually select the primary container 150 for the dispensing of product by the dispenser 100 by manipulating an appropriate user interface, such as the top plate 108.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method of operating a dispensing system, comprising the steps of:
    alternating between active and lockout modes within a first timing sequence, wherein during the active mode at least one sensor is active to detect sensory input, and whereupon detection of the sensory input results in product being released from a first container, and wherein during a lockout mode product is not released from the first container; and
    alternating between active and lockout modes within a second timing sequence, wherein during the active period at least one sensor is active to detect sensory input, and whereupon detection of the sensory input results in product being released from a second container, and wherein during a lockout mode product is not released from the second container,
    wherein the expiration of the first timing sequence, and the initiation of the second timing sequence, occurs from at least one of the lapsing of a time interval, sensory input, and manual input from a user.

2. The method of operating a dispensing system according to claim 1, including the step of initiating a lockout mode upon the detection of sensory input during the active mode.

3. The method of operating a dispensing system according to claim 2, wherein the lockout mode has a duration of between about 1 minute to about 180 minutes, more preferably between about 10 minutes to about 60 minutes, and most preferably between about 15 minutes to about 40 minutes.

4. The method of operating a dispensing system according to claim 2, wherein the lockout mode has a duration dependent on at least one of a pre-programmed specified time interval, upon a user selected time interval, and upon sensory input from one or more of the at least one sensor and an additional sensor.

5. The method of operating a dispensing system according to claim 1, wherein two or more sensors are provided.

6. The method of operating a dispensing system according to claim 5, wherein the two or more sensors include one or more of a light sensing element, such as a photodetector, photodiode light detector, photoresistor, photodiode, or phototransistor; a passive infrared sensor; a motion sensor; an acoustic sensor; a humidity sensor; a temperature sensor; a pressure sensor; a vibration sensor; an accelerometer; and a chemical sensor.

7. The method of operating a dispensing system according to claim 1, wherein during the lockout mode of the first and second timing sequences, input from the at least one sensor does not activate the dispensing system.

8. The method of operating a dispensing system according to claim 1, wherein during the lockout modes of the first and second timing sequences, the at least one sensor is active to detect sensory input and performs one or more of the steps of not initiating the dispensing of product from the first and second containers and initiating a lighting sequence comprising one or more pulses of one or more lights.

9. The method of operating a dispensing system according to claim 1, wherein the alternating first and second timing sequences include a duration of between 1 hour and 1 month, or more preferably between 12 hours and 2 weeks, or most preferably 24 hours.

10. A method of operating a dispensing system, comprising the steps of:
activating at least one sensor during a first time period to detect sensory input, whereupon detection of the sensory input results in the release of product from a first container; and
activating a button, wherein actuation of the button for a duration of <a time period T results in no release of product, and wherein the depression of the button for a duration ≥T results in the release of product.

11. The method of operating a dispensing system according to claim 10, further including the step of activating the at least one sensor during a second timing sequence to detect sensory input, whereupon detection of the sensory input results in the release of product from a second container.

12. The method of operating a dispensing system according to claim 11, wherein actuation of the button at least twice within a specified interval of time SI results in the alternation between the first and second timing sequences.

13. The method of operating a dispensing system according to claim 12, further including the step of alternating between active and lockout modes within the first and second timing sequences, wherein during the active mode the at least one sensor is active to detect sensory input, and whereupon detection of the sensory input results in the release of product from the first or second container, respectively, and wherein during the lockout mode product is not released from the first container based on the detection of sensory input.

14. The method of operating a dispensing system according to claim 13, wherein the alternation between the first timing sequence and the second timing sequence occurs from at least one of the lapsing of a timing sequence, sensory input and manual actuation of the button twice within the SI.

15. The method of operating a dispensing system according to claim 14, further including the step of actuating the button for a time period during one of the lockout modes or active modes to cause the release of product from one of the first and second containers.

16. A dispenser, comprising:
a housing adapted to receive a first and second container therein; and
at least one sensor associated with the housing,
wherein the dispenser provides for alternating between active and lockout modes within first and second timing sequences, wherein during the active mode sensory input from the at least one sensor results in product being released from the first or second container, respectively, and wherein during a lockout mode product is not released from the first or second container, respectively.

17. The dispenser of claim 16, wherein the expiration of the first timing sequence, and the initiation of the second timing sequence, occurs from at least one of the lapsing of a time interval, sensory input, and manual input from a user.

18. The dispenser of claim 16, wherein 3 or more sensors are provided.

19. The dispenser of claim 16 further including an actuator drive system for selectively releasing product from the first and second containers, wherein the actuator drive system includes first and second armatures.

20. The dispenser of claim 19, wherein during the first timing sequence the first armature is driven upwardly to raise the first container to release product therefrom.

* * * * *